US010022117B2

(12) United States Patent
Poucher et al.

(10) Patent No.: US 10,022,117 B2
(45) Date of Patent: *Jul. 17, 2018

(54) METHOD OF TREATING URINARY INCONTINENCE

(71) Applicant: Coloplast A/S, Humlebaek (DK)

(72) Inventors: Neal Poucher, North Oaks, MN (US); Sarah J. Deitch, Minneapolis, MN (US); Allen Gaynor, Coon Rapids, MN (US); Michael M. Witzmann, Shoreview, MN (US)

(73) Assignee: Coloplast A/S, Humlebaek (DE)

( * ) Notice: Subject to any disclaimer, the term of this patent is extended or adjusted under 35 U.S.C. 154(b) by 306 days.

This patent is subject to a terminal disclaimer.

(21) Appl. No.: 14/706,985

(22) Filed: May 8, 2015

(65) Prior Publication Data

US 2016/0157980 A1 Jun. 9, 2016

Related U.S. Application Data

(60) Provisional application No. 62/087,252, filed on Dec. 4, 2014.

(51) Int. Cl.
*A61F 2/04* (2013.01)
*A61B 17/04* (2006.01)
(Continued)

(52) U.S. Cl.
CPC .... *A61B 17/0401* (2013.01); *A61B 17/00234* (2013.01); *A61B 17/06109* (2013.01);
(Continued)

(58) Field of Classification Search
CPC .............. A61F 2/0004–2/0077; A61F 2220/0008–2220/0016; A61B 17/0401–17/0466; A61B 2017/00805
See application file for complete search history.

(56) References Cited

U.S. PATENT DOCUMENTS 6,502,578 B2 1/2003 Raz et al.
6,506,197 B1 1/2003 Rollero et al.
(Continued)

FOREIGN PATENT DOCUMENTS

EP 1484022 A2 12/2004
EP 2277456 A1 1/2011
(Continued)

OTHER PUBLICATIONS

Office Action dated May 9, 2017 in U.S. Appl. No. 14/706,981.
Office Action dated Feb. 28, 2018 in U.S. Appl. No. 15/594,658.

*Primary Examiner* — Thaddeus Cox
(74) *Attorney, Agent, or Firm* — Coloplay Corp., Coloplast A/S; Nick Baumann

(57) ABSTRACT

A method of treating urinary incontinence in a patient includes forming one and only one incision in the patient and implanting a base of a support by placing an anchor into tissue of an obturator foramen. The anchor is attached to the base of the support by a continuous suture loop that is looped through an eyelet of the anchor and engaged through the base of the support. The method includes breaking the continuous suture loop, tying a knot in the suture, and fixating the base of the support in the patient. An arm of the support is implanted by placing a second anchor into periosteum tissue lateral to a pubic symphysis with a second continuous suture loop looped through an eyelet of the second anchor and engaged through the arm of the support.

9 Claims, 72 Drawing Sheets

(51) Int. Cl.
   *A61F 2/00* (2006.01)
   *A61B 17/00* (2006.01)
   *A61B 17/06* (2006.01)
   *A61B 17/3209* (2006.01)
   *A61B 17/34* (2006.01)
   *A61B 50/20* (2016.01)
   *A61B 90/00* (2016.01)

(52) U.S. Cl.
   CPC .... *A61B 17/06166* (2013.01); *A61B 17/3209* (2013.01); *A61B 17/3468* (2013.01); *A61B 50/20* (2016.02); *A61F 2/0031* (2013.01); *A61F 2/0045* (2013.01); *A61F 2/0063* (2013.01); *A61B 2017/0046* (2013.01); *A61B 2017/0053* (2013.01); *A61B 2017/00455* (2013.01); *A61B 2017/00805* (2013.01); *A61B 2017/0404* (2013.01); *A61B 2017/0409* (2013.01); *A61B 2017/0412* (2013.01); *A61B 2017/0414* (2013.01); *A61B 2017/0417* (2013.01); *A61B 2017/0427* (2013.01); *A61B 2017/0445* (2013.01); *A61B 2017/0464* (2013.01); *A61B 2017/061* (2013.01); *A61B 2017/0609* (2013.01); *A61B 2090/037* (2016.02); *A61B 2090/0801* (2016.02); *A61F 2002/0072* (2013.01); *A61F 2220/0008* (2013.01); *A61F 2220/0016* (2013.01)

(56) References Cited

U.S. PATENT DOCUMENTS

| | | | |
|---|---|---|---|
| 6,595,911 B2 | 7/2003 | Lovuolo | |
| 6,641,524 B2 | 11/2003 | Kovac | |
| 6,695,855 B1 | 2/2004 | Gaston | |
| 7,320,701 B2 | 1/2008 | Haut et al. | |
| D572,546 S | 7/2008 | Stahm | |
| 7,914,437 B2 | 3/2011 | Gozzi et al. | |
| 8,409,075 B2 | 4/2013 | Chu | |
| 8,579,797 B2 | 11/2013 | Arnal et al. | |
| 8,771,314 B2 | 7/2014 | Crombie et al. | |
| 9,198,747 B2 | 12/2015 | De Leval | |
| 2002/0019649 A1 | 2/2002 | Sikora et al. | |
| 2004/0002734 A1 | 1/2004 | Fallin et al. | |
| 2004/0243178 A1 | 12/2004 | Haut et al. | |
| 2005/0019368 A1 | 1/2005 | Cook et al. | |
| 2006/0030884 A1 | 2/2006 | Yeung et al. | |
| 2009/0041548 A1 | 2/2009 | Stahm | |
| 2009/0137862 A1 | 5/2009 | Evans et al. | |
| 2009/0171143 A1 | 7/2009 | Chu et al. | |
| 2010/0105979 A1 | 4/2010 | Hamel et al. | |
| 2010/0191045 A1 | 7/2010 | Gobron et al. | |
| 2010/0197999 A1 | 8/2010 | Deegan et al. | |
| 2010/0269422 A1 | 10/2010 | Stahm | |
| 2011/0022061 A1 | 1/2011 | Orphanos et al. | |
| 2011/0218387 A1 | 9/2011 | Lamson et al. | |
| 2011/0297161 A1 | 12/2011 | Deitch | |
| 2013/0006045 A1 | 1/2013 | Deitch et al. | |
| 2013/0012765 A1 | 1/2013 | Vemuri et al. | |
| 2013/0023724 A1 | 1/2013 | Allen et al. | |
| 2013/0238023 A1 | 9/2013 | Wales et al. | |
| 2013/0245700 A1 | 9/2013 | Choinski | |
| 2013/0253260 A1 | 9/2013 | Lund et al. | |
| 2013/0325063 A1 | 12/2013 | Norton et al. | |
| 2014/0128914 A1 | 5/2014 | Deitch et al. | |
| 2015/0297333 A1 | 10/2015 | Poucher et al. | |

FOREIGN PATENT DOCUMENTS

| | | |
|---|---|---|
| EP | 2543341 A2 | 1/2013 |
| EP | 2727539 A2 | 5/2014 |
| EP | 2740415 A1 | 6/2014 |
| WO | 2007097994 A2 | 8/2007 |
| WO | 2008107026 A2 | 9/2008 |
| WO | 2010062851 A1 | 6/2010 |
| WO | 2013044228 A1 | 3/2013 |

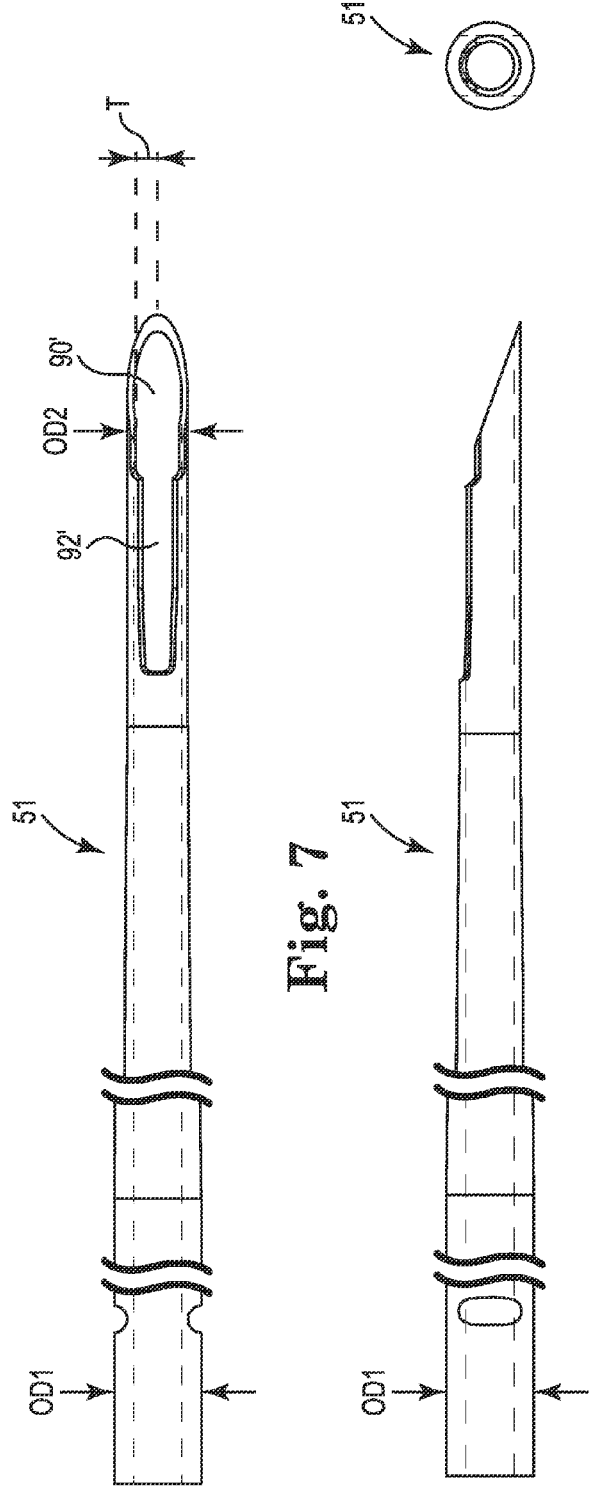

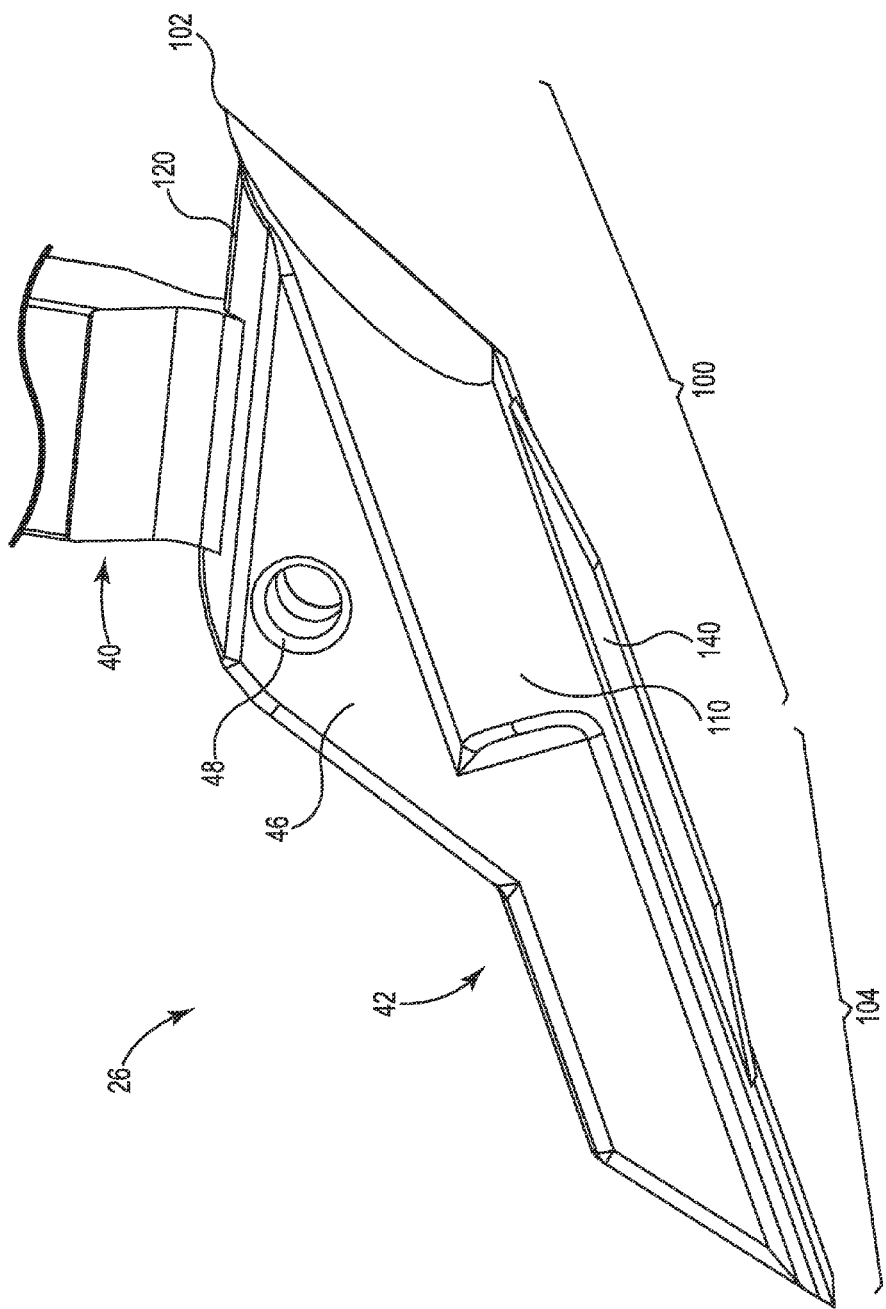

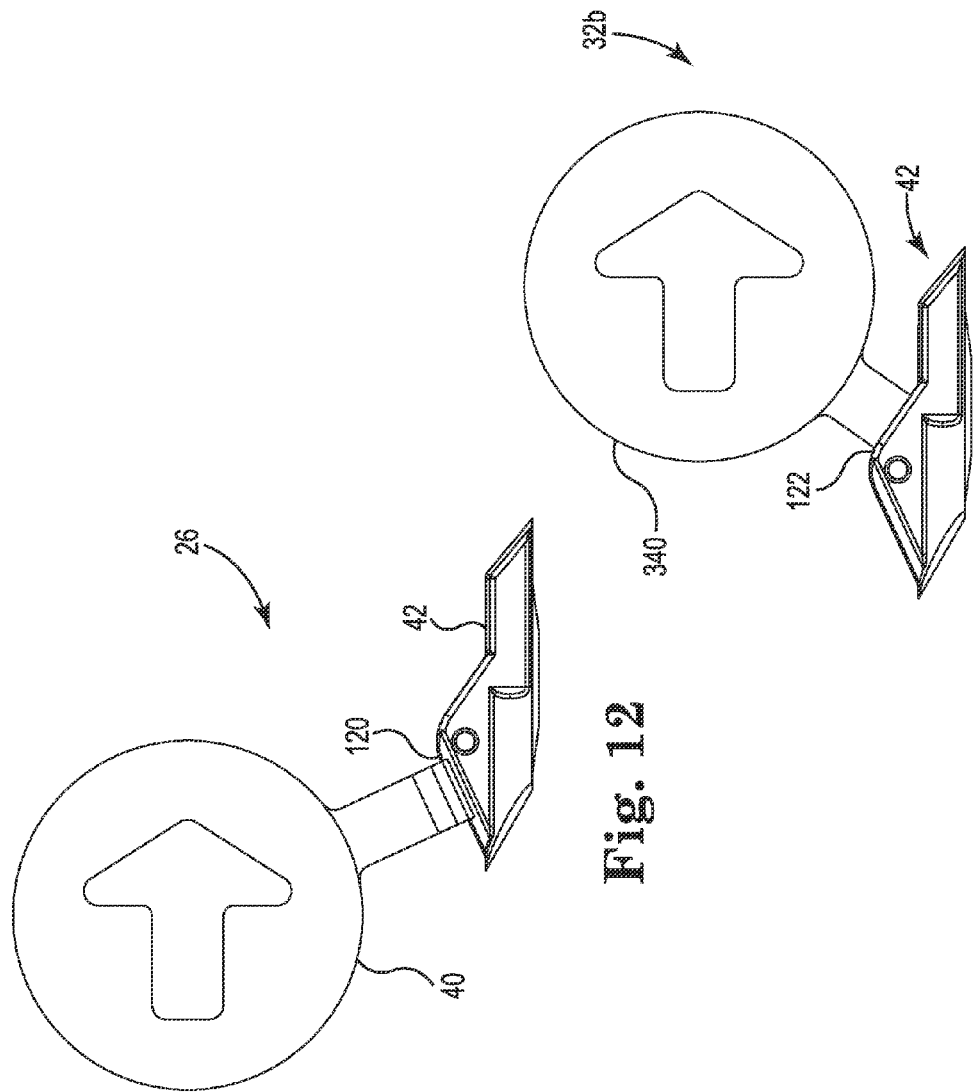

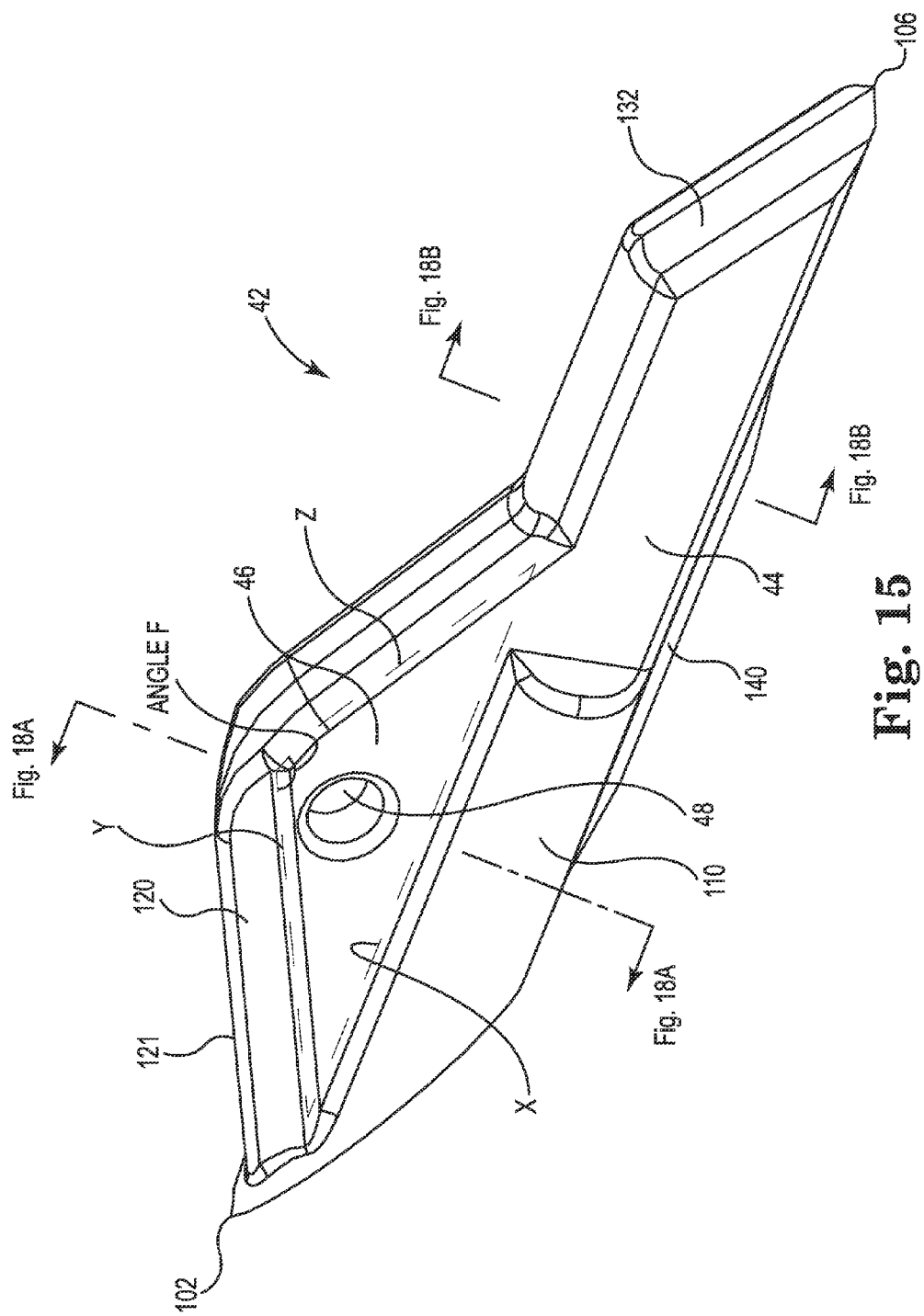

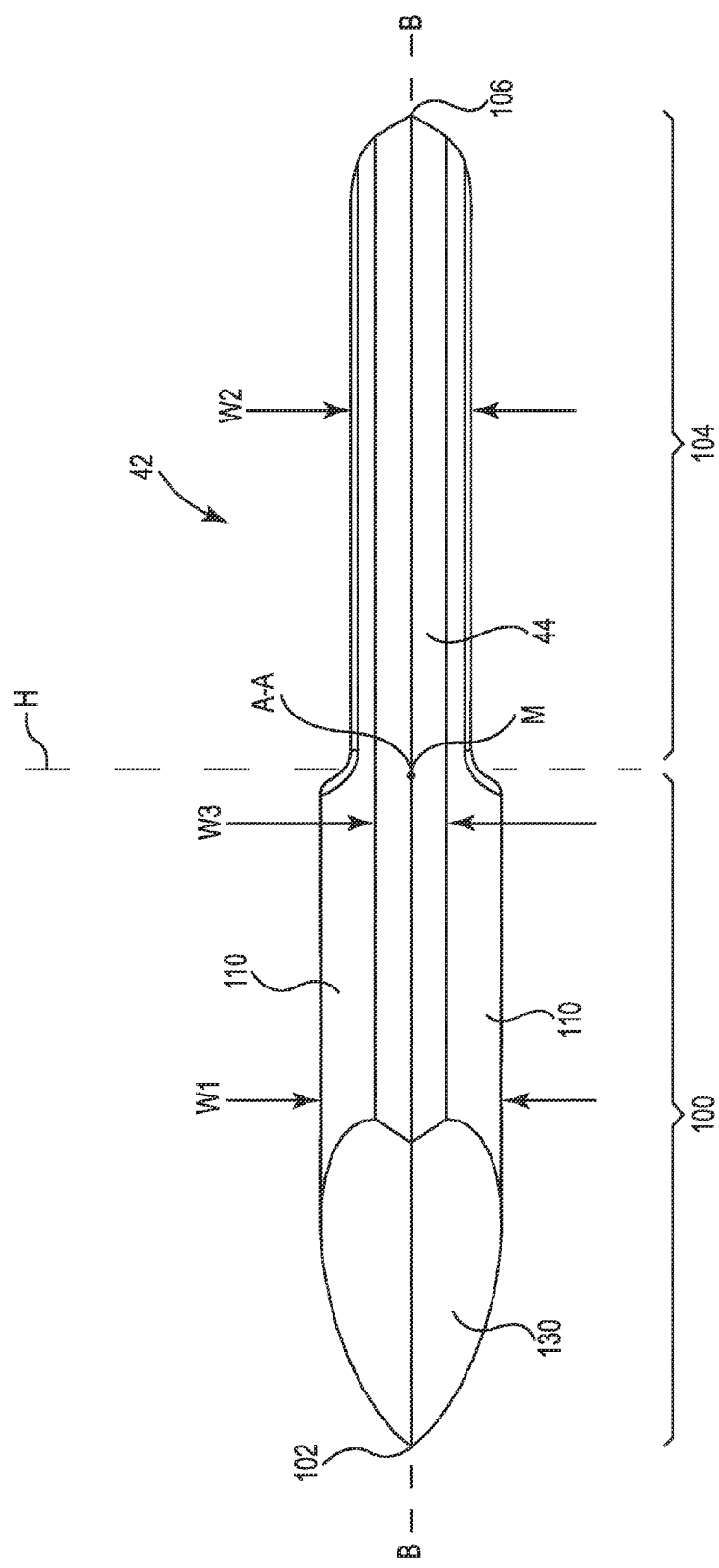

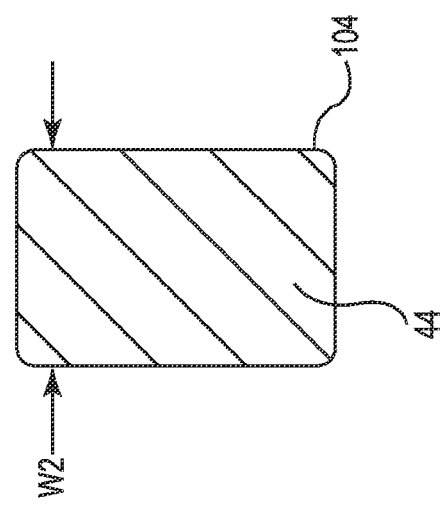
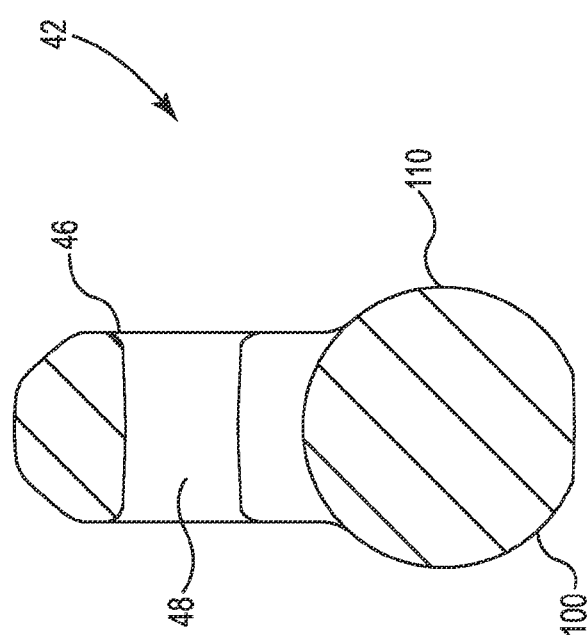
Fig. 18B
Fig. 18A

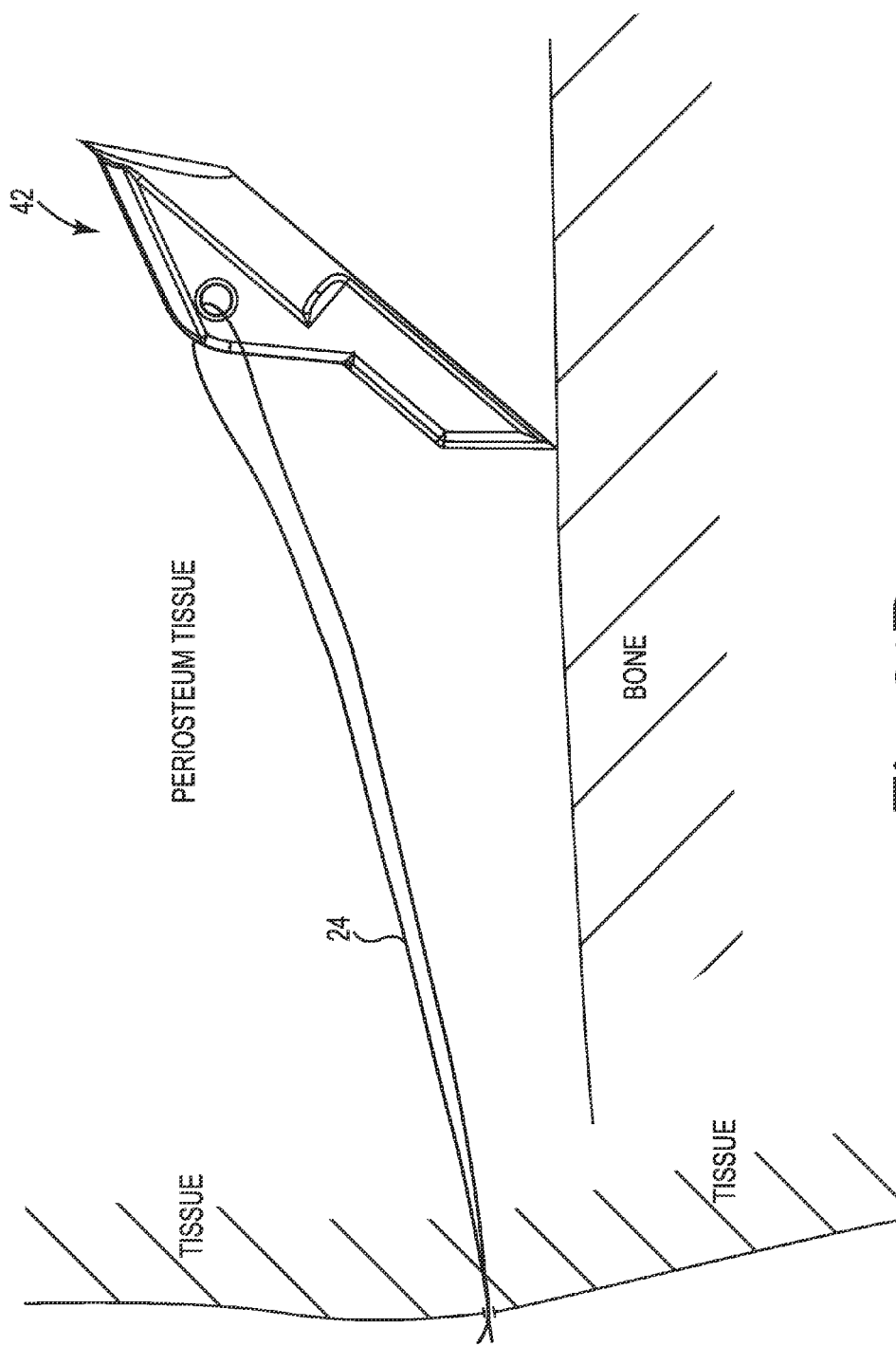

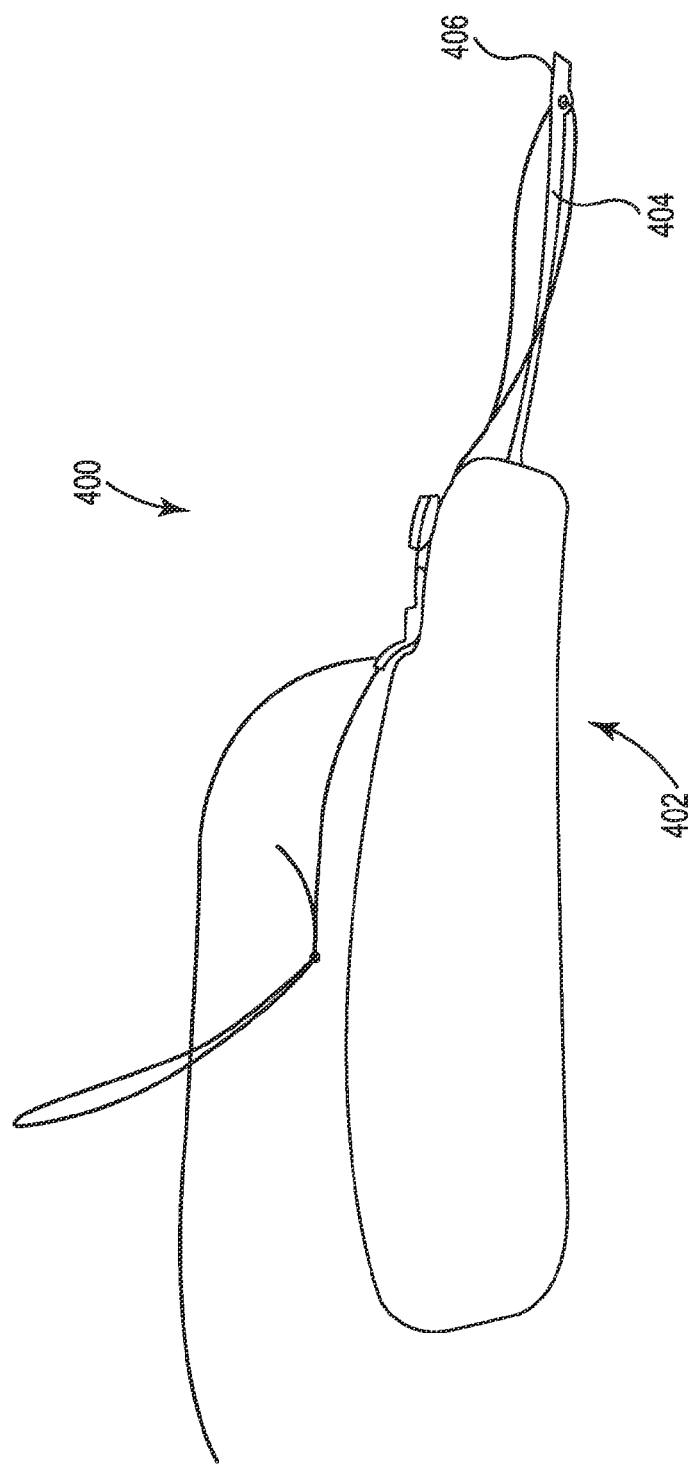

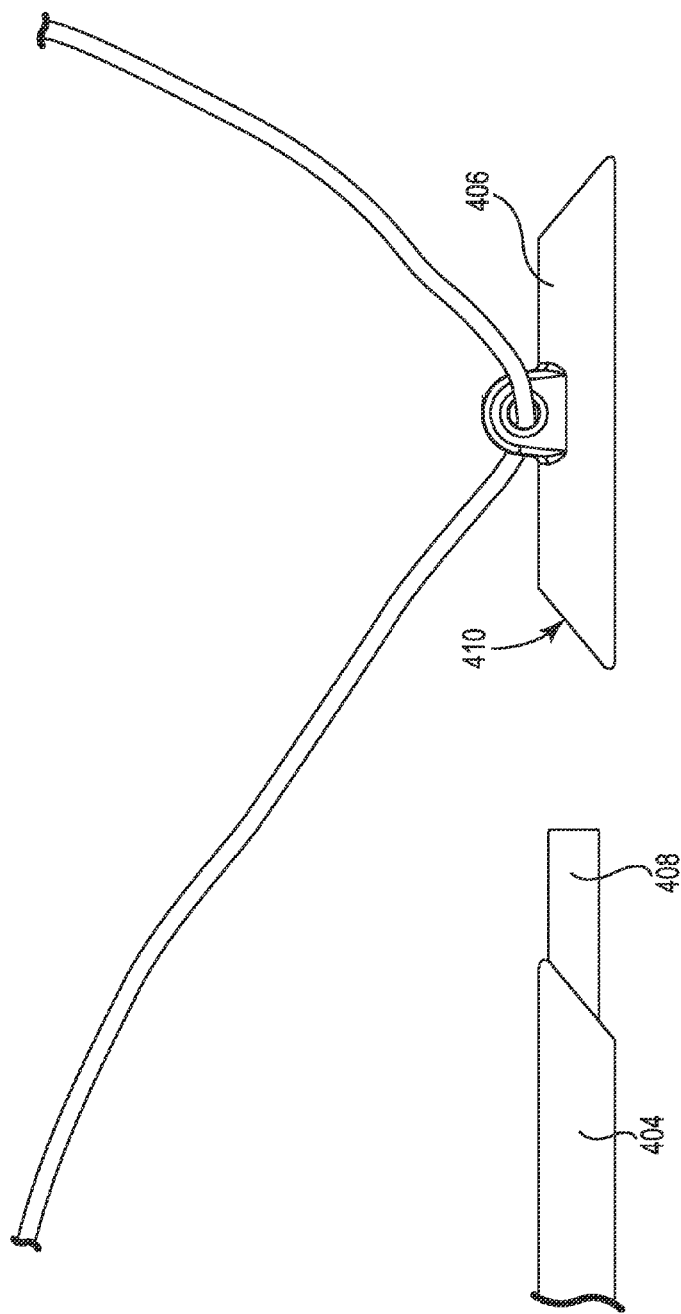

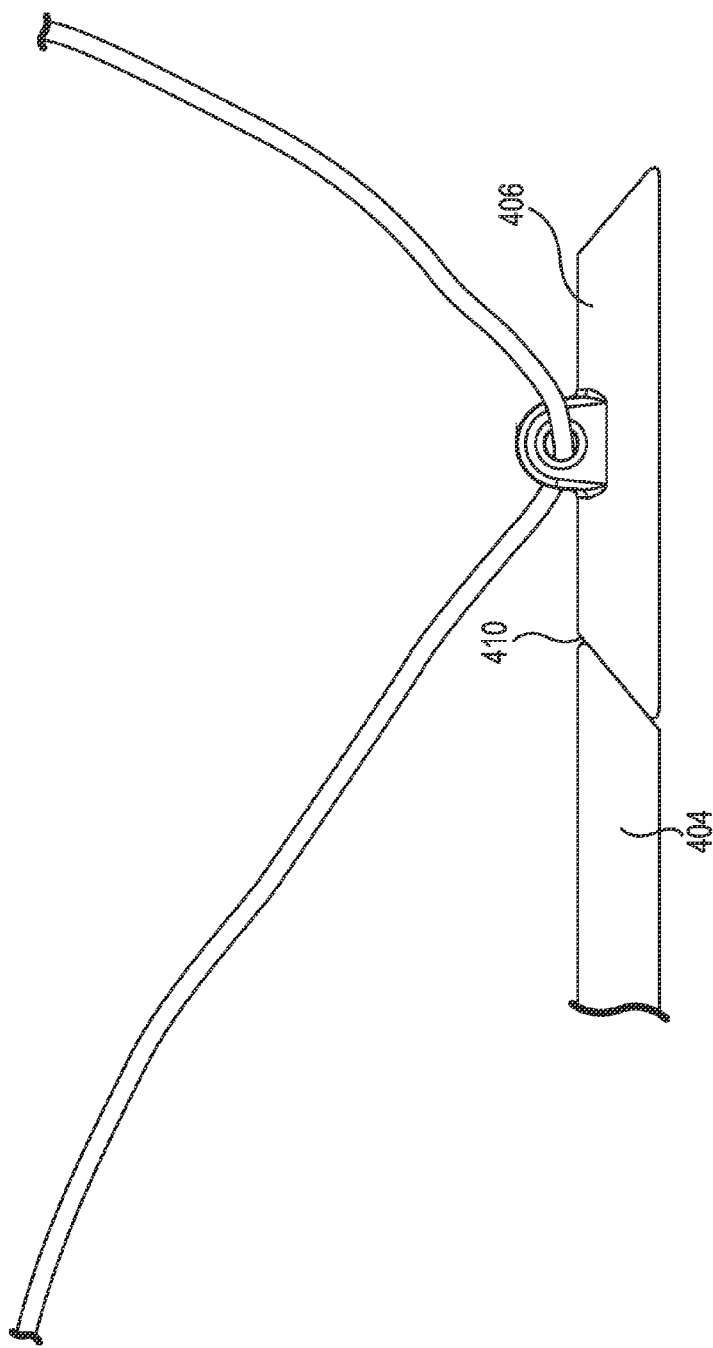

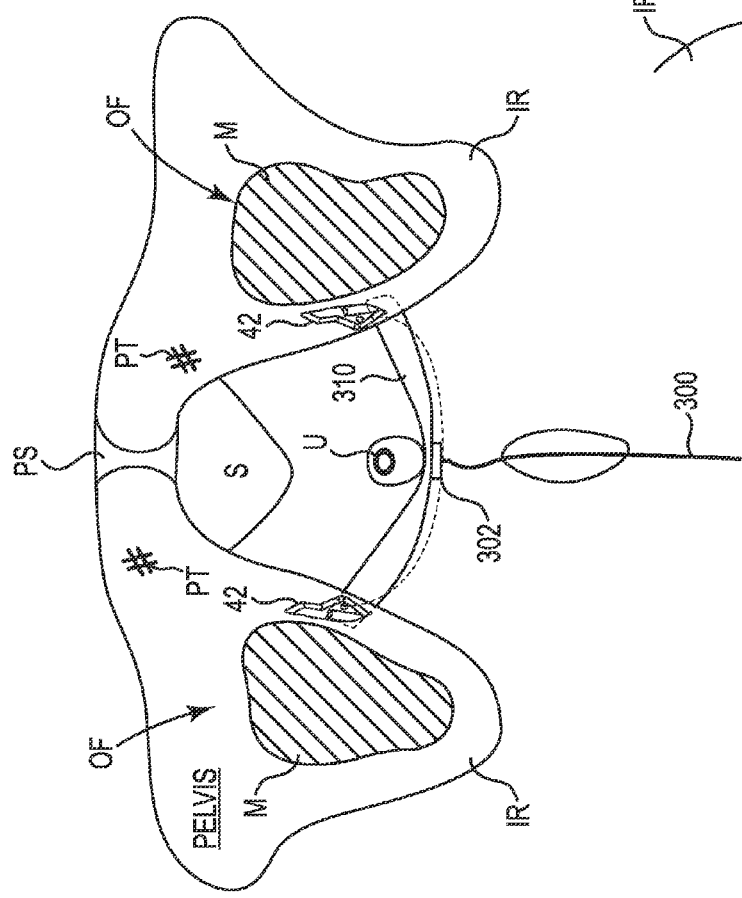
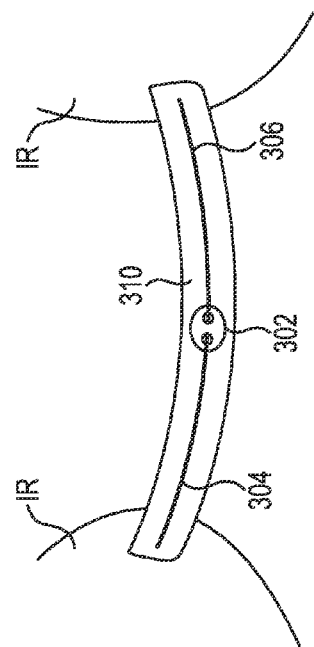
Fig. 68A
Fig. 68B

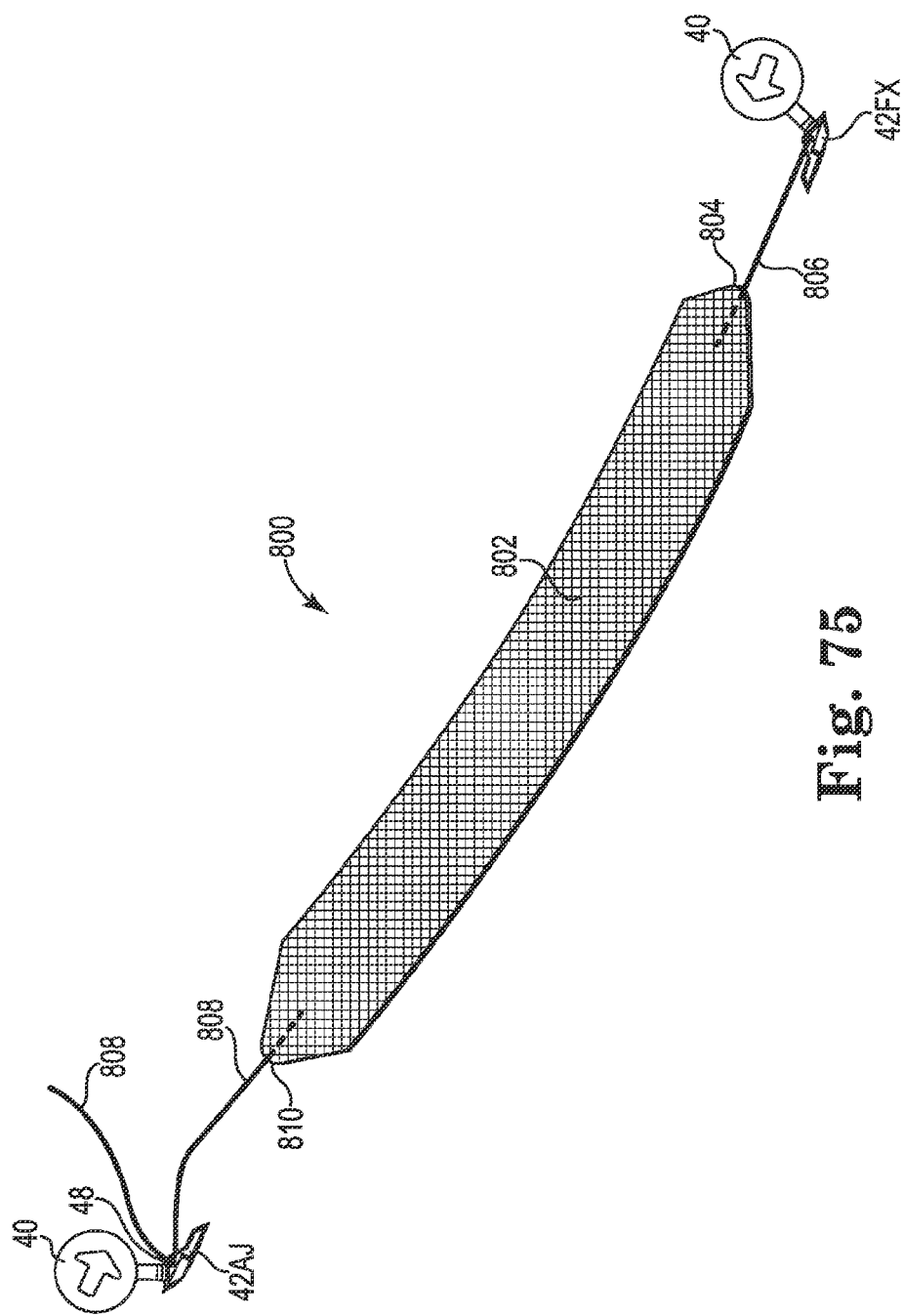

METHOD OF TREATING URINARY INCONTINENCE

BACKGROUND

Some surgical implants are fixed in place with one or more suture knots. Other surgical implants, for example fabric or mesh supports, are fixed in place with an anchor attached to a suture, where the suture is tied against the support. These surgical implants are usefully employed to treat male or female incontinence, pelvic organ prolapse, and in reconstructing areas of tissue.

Improved devices and methods of fixating surgical implants would be welcomed by patients and healthcare workers.

SUMMARY

One aspect provides a tissue anchor system including a support material, a suture engaged with the support material, an anchor assembly, and an introducer. The anchor assembly includes an insertion tab removably secured to an anchor. The anchor includes a body having a mid-point located between a leading end and a trailing end, with a tissue engagement fin forming an upper edge of the body, and an eyelet formed in the tissue engagement pod. The tissue engagement fin is asymmetric relative to the mid-point. The introducer has a cannula defining a slot sized to receive the body of the anchor and an ejection mechanism provided to eject the anchor out of the cannula.

One aspect provides a tissue anchor having a body, protrusions from the body, and a tissue engaging fin. The body is oriented on a longitudinal axis and has a leading tip, a leading end portion extending from the leading tip, a trailing end portion connected to the leading end portion, with the trailing end portion terminating in a trailing tip that is located opposite of the leading tip. First and second protrusions are formed on the leading end portion of the body, with each of the first and second protrusions extending outward in a radial direction perpendicular to the longitudinal axis. A first anchor width measured between the first and second protrusions is greater than a second anchor width measured at the trailing end portion of the body. The tissue engaging fin is integrated with the leading end portion of the body and oriented in a direction perpendicular to the radial direction of the first and second protrusions. The tissue engaging fin has a fin width and is provided with an eyelet formed through the fin width. A gripping tab is removably attached to the tissue engaging fin.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other.

FIG. 7 is a top view, FIG. 8 is a side view, and FIG. 9 is a cross-sectional view of the cannula of the introducer illustrated in FIG. 4.

FIG. 11 is a perspective view of one embodiment of the anchor assembly illustrated in FIG. 1.

FIG. 12 is a side view of one embodiment of the anchor assembly illustrated in FIG. 1.

FIG. 13 is a top view of one embodiment and FIG. 14 is a side view of one embodiment of anchor assemblies suitable for use with the tissue anchor system illustrated in FIG. 1.

FIG. 15 is a perspective view of one embodiment of an anchor suitable for use with the tissue anchor system illustrated in FIG. 1.

FIG. 16 is a top view and FIG. 17 is a bottom view of the anchor illustrated in FIG. 15.

FIG. 18A is cross-sectional view of the leading end portion of the anchor and FIG. 18B is cross-sectional view of the trailing end portion of the anchor.

FIGS. 21A-21C are schematic views of the anchor illustrated in FIG. 15 rotated into engagement with tissue.

FIG. 23 is a perspective view of one embodiment of an anchor assembly coupled to an introducer and suitable for use in the tissue anchor system illustrated in FIG. 1.

FIG. 24 is a side view of an anchor assembly attachable to a pin extending from an introducer.

FIG. 25 is a side view of the anchor assembly attached to the pin illustrated in FIG. 24.

FIGS. 63-68B are schematic views of embodiments of a method of anchoring a support material to tissue.

FIG. 75 is a perspective view of one embodiment of an adjustable incontinence treatment device.

DETAILED DESCRIPTION

Figure 1:
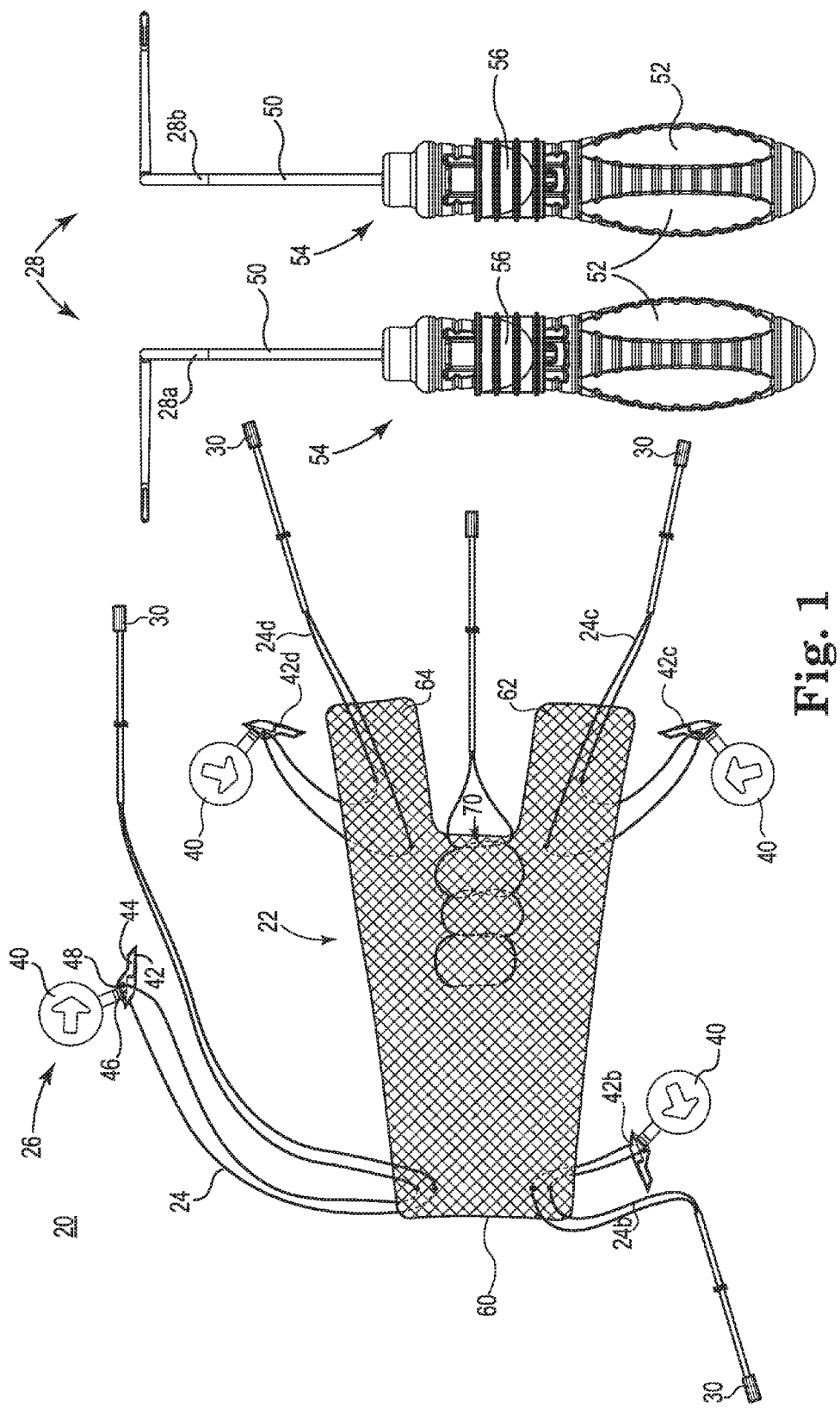
FIG. 1 is a top view of one embodiment of a tissue anchor system including a support material, and anchor assembly, and an introducer.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

The features of the various exemplary embodiments described in this application are suitable and intended to be combined with each other, unless specifically noted otherwise.

Anterior means "forward" or "front," and posterior means "rearward" or "back." Relative to surfaces of an organ in the human body, an anterior surface of an instrument inserted into the organ will be oriented forward toward the belly and a posterior surface will be oriented rearward toward the spine.

End means an end-most location and end portion means that segment adjacent to and near the end of an object. For example, two opposing ends of an object are each equidistant from a mid-point of the object and between the mid-point and each end of the object is an end portion of the object.

Soft tissue is tissue other than bone. Soft tissue is not bone.

Embodiments provide a tissue anchor having a geometric asymmetry and asymmetric mass distribution along a length of the anchor which encourages the anchor to be rotated into a stable configuration in the tissue.

Embodiments provide a tissue anchor system having an anchor that will durably anchor into periosteum tissue covering a bony surface, or durably anchor into dense fibrous tissue where muscle inserts into the bone. An anchor so anchored is suitable for suspending support material or is useful in implanting devices in the human body.

Embodiments provide a tissue anchor system including an introducer that is configured to deliver an anchor to an intracorporeal tissue site. The introducer includes a cannula that allows placement of an anchor at a landmark in tissue deep within an incision site, which may be out of the field of vision of the surgeon. The anchor is configured to be secured within the cannula so that it does not rotate or fall out of the cannula during insertion into the tissue. A length of suture is provided that is attached to the anchor, where the suture may be tied or otherwise terminated to itself outside of the incision site and then subsequently directed to the intracorporeal landmark.

Embodiments provide a tissue anchor system provided to treat male urinary incontinence that is advantageously implanted through a single incision formed in the patient. A first anchor is anchored to the tissue of a first obturator foramen of the patient, and a second anchor is anchored to the tissue of a second obturator foramen of the patient to secure in inferior portion of the support material to the patient. A third anchor is provided to anchor a first pre-pubic arm to the periosteum tissue on one side of the pubic symphysis, and a fourth anchor is provided to anchor a second pre-pubic arm of the support material to the periosteum tissue on the other side of the pubic symphysis. Each of the anchor assemblies includes a suture extending from an anchor, and the surgeon is instructed to suitably terminate or tighten the suture to capture the support material between a knot formed in the suture and the anchor implanted in the tissue. The surgeon, guided by experience and instruction provided with the tissue anchor system, follows a routine of first centering and fixating the inferior portion of the support material relative to the obturator foramen by suitably tensioning and tying knots in the suture. Subsequently, the surgeon centers and fixates the superior portion of the support material near an upper portion of the pelvis on either side of the pubic symphysis. Some aspects of the tissue anchoring system include a separate plication mechanism provided to take up the slack in tension the support material over the tissue of the urethra.

Some incontinence treatment devices have several arms, including some form of arms that traverse the obturator foramen (called transobturator arms) and other arms that are implanted anterior to the pubic bone (called pre-pubic arms). A first set of tools is used to place the transobturator arms and a second, different set of tools is used to place the pre-pubic arms. The pre-pubic arms are inserted into a first incision and tunnelled anterior to the pelvis to exit the skin of the abdomen through a second incision and respective third incision.

In contrast, embodiments of the system described in this specification provide a support material that is implantable into the patient through a single incision with anchor assemblies that do not create a second or other incisions/openings in the skin. The system obviates the use of transobturator arms and additional tools that tunnel the pre-pubic arms under the skin. The system is easier to implant compared to a four arm or six arm support, and reduces the amount of time that the patient is in the operating room.

One approach to treating urinary incontinence places a support inferior to the urethra and directs arms upward from the support alongside the bladder along a U-shaped pathway. A significant advance over the U-shaped pathway was provided by Dr. Emmanuel Delorme as described in his U.S. Pat. No. 6,638,211 and included placing arms of a support through the obturator foramen along a V-shaped pathway. This application provides another advance in supporting the pelvic anatomy by recognizing that support material can be robustly attached to the periosteum tissue through the use of an anchoring system. The anchoring system allows the surgeon to place the support inside of the patient and directly fixate the support to periosteum tissue that is present over the exterior of the pelvis bone. This approach does away with needles and other tools that tunnel the arms of a support through tissue. The anchoring system described in this application is compatible with a true single (only one) incision formed in the patient.

FIG. 1 is a top view of one embodiment of a tissue anchor system 20 (the system 20). The system 20 is illustrated in one useful form for delivery to an end-user healthcare facility and includes a support material 22, sutures 24 engaged with the support material 22, an anchor assembly 26 engaged with each of the sutures 24, and a set of introducers 28.

The support material 22 is provided to support the urethra when implanted in the patient. Suitable materials for the support material 22 include autograft material (the patient's own tissue), allograft material (tissue from a cadaver), xenograft material (tissue from another species), or synthetic materials such as woven fabrics, knitted fabrics, meshes, nonwoven fabrics, meshes, fibrillated fibers, or spun and fibrillated fibers. In some embodiments, the support material 22 is fabricated to include voids (pores) configured to allow tissue ingrowth into the support material 22. The pores are generally larger, on average, than 75 μm. One suitable support material 22 is a knitted polypropylene mesh, where each strand of the mesh is knitted from a polypropylene filament.

The sutures 24 are threaded through or otherwise engaged with the support material 22. Each suture 24 is threaded through or otherwise engaged with one anchor assembly 26. One suitable suture 24 is fabricated from a single monofilament of polypropylene that is threaded through both the anchor assembly 26 and the support material 22 to form a continuous closed loop of suture. In one embodiment, the trailing end portions of each suture 24 are brought together and maintained within a conduit 29, and at least the ends of the suture 24 are welded (heat welded or sonically welded) together to maintain the ends of the continuous closed loop of suture in an organized fashion until the surgeon desires to break the suture 24 at the point of the weld. In one embodiment, the weld is a break pad 30 that is formed by crushing the ends of the suture 24 into a flat structure that is more brittle than and easier to break than the suture 24 is itself. The break pad 30 maintains the suture 24 in an organized fashion until the surgeon desires to access the free ends of the suture 24 and tie a knot. In one embodiment, the welded break pad 30 is formed through the ends of the suture 24 and through the conduit 29. The conduit 29 advantageously allows the surgeon to identify which suture strand is associated with each portion of the support 22 and also manages the sutures into an organized bundle for ease of handling during implantation of the support 22.

The anchor assembly 26 includes an insertion tab 40 that is removably secured to an anchor 42. The anchor 42 includes a body 44, a tissue engagement fin 46 attached to the body 44, and an eyelet 48 formed in the tissue engagement fin 46. The suture 24 is threaded through the eyelet 48 and gathered/secured at the break pad 30. The insertion tab 40 provides a convenient handle for the surgeon or the surgical staff to handle the anchor 42. The length of the anchor 42 is in a range from about 4-20 mm, which can present a small area for grasping when a person is wearing surgical gloves. The insertion tab 40 allows the surgeon or the surgical staff to handle the anchor 42 comfortably when loading the anchor 42 into the introducer 28.

The set of introducers 28 includes a first tool 28a for passing one anchor 26 to the patient's right side obturator membrane and a second tool 28b for passing a second anchor 26 to the patient's left side obturator membrane. Each of the introducers 28a, 28b includes a cannula 50 extending from a handle 52, and an ejection mechanism 54 including a button 56 that communicates with a rod/wire disposed within the cannula 50. Movement of the button 56 in a distal direction (forward) moves the rod/wire in a distal direction, which acts upon the anchor 42 to eject the anchor out of the cannula 50. The introducers 28a, 28b have a "handedness" depending on whether the anchor 42 is into a left or a right obturator foramen. However, each introducer 28a or 28b is equally well suited for inserting one of the anchors 42 into periosteum tissue.

An optional a plication mechanism 70 is engaged with the support material 22. The plication mechanism 70 operates to gather up any slack that might be present in the support 22 after implantation.

Figure 2:
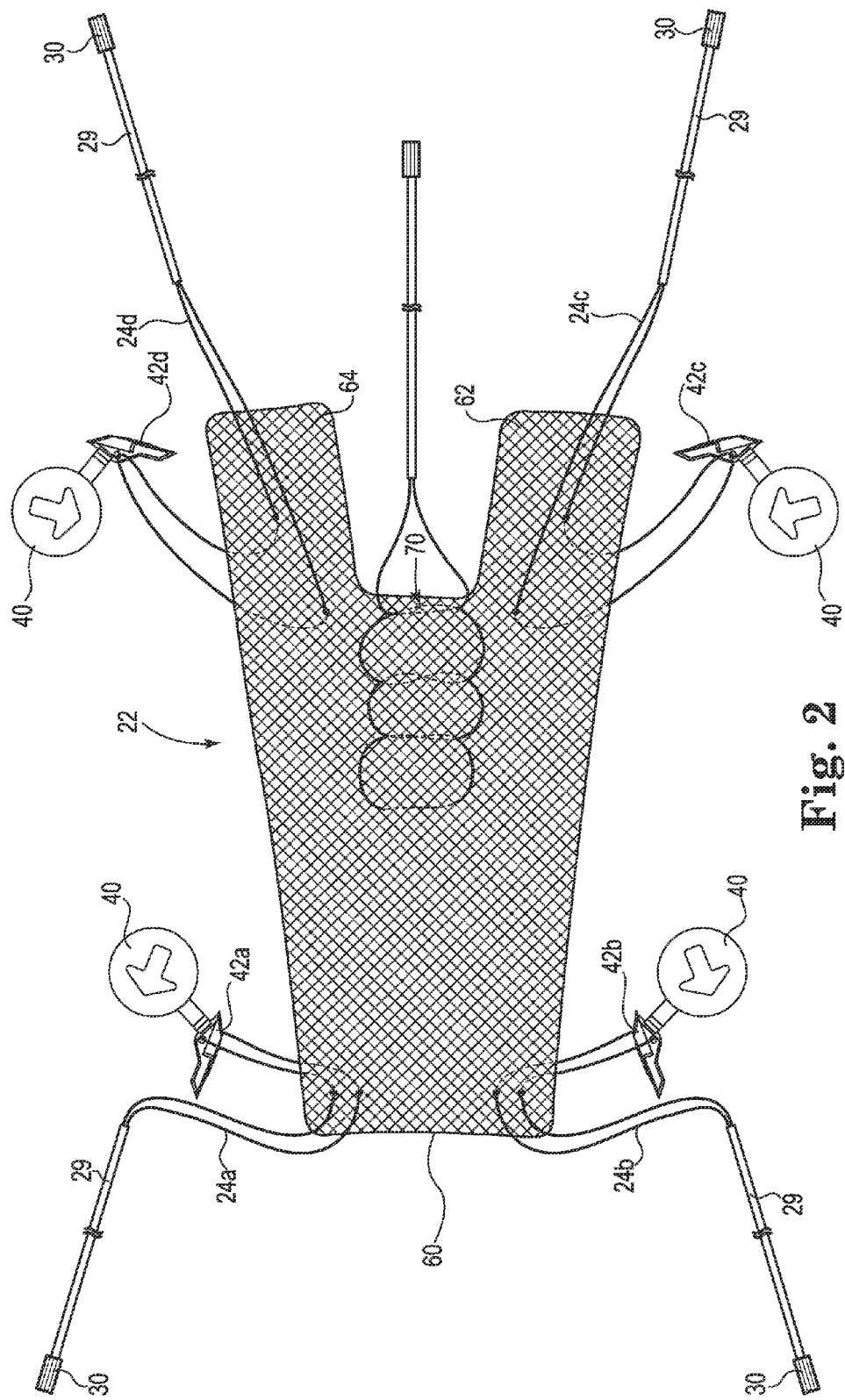
FIG. 2 is a top view of one embodiment of the support material illustrated in FIG. 1.

FIG. 2 is a top view of four anchor assemblies 42a, 42b, 42c, 42d including an insertion tab 40 and engaged with the support material 22. The anchors 42 are located between the support 22 and the patient's body, and the conduits 29 and the break pads 30 are located between the support 22 and the surgeon. Thus, relative to the support 22, the anchors 42 are located posterior (distal the surgeon) and the conduits 29/break pads 30 are located anterior (proximal the surgeon).

Each of the four anchor assemblies 42a, 42b, 42c, 42d is engaged with the support material 22 by a respective suture 24a, 24b, 24c, 24d, where each suture 24a, 24b, 24c, 24d penetrates the support 22 at more than one location. In the embodiment illustrated, each suture 24a, 24b, 24c, 24d penetrates the support 22 at two locations. We studied the effectiveness of the compression provided by the support 22 in elevating and compressing the urethra and have determined that the multiplicity of penetrations of the support 22 by the suture 24 as illustrated in FIG. 2 provides optimal support to the urethra. For example, two penetration points for the sutures 24a, 24b on each side of the base 60 (four penetrations total for two sutures 24a, 24b) provides excellent suspension of the base 60 between the obturator foramen when the support 22 is implanted. Two penetration points oriented on a diagonal line from an interior location of an arm 62, 64 to an outside corner of each arm 62, 64 for each suture 24c, 24d has been determined to provide excellent tension to the support 22 when implanted.

The support material 22 includes a base 60 associated with a first anchor 42a that is provided to be anchored into a first obturator membrane and a second anchor 42b that is provided to be anchored into a second obturator membrane of the patient. The support material 22 additionally includes a first pre-pubic arms 62 associated with a third anchor 42c that is provided to be anchored into the periosteum tissue on one side of the pubic symphysis, and a second pre-pubic arms 64 associated with a fourth anchor 42d that is provided to be anchored into the periosteum tissue on the other side of the pubic symphysis. The support material 22 is provided to hospital or the surgeon in a package with instructions for use and includes each of the four anchors 42a-42d engaged with the support material 22 by one of the respective sutures 24a-24d.

In one embodiment, a plication mechanism 70 is engaged with the support material 22. The plication mechanism 70 is provided to allow the surgeon to remove slack from a central region of the support material 22 after the base 60 and the pre-pubic arms 62, 64 have been secured to tissue. In one embodiment, the plication mechanism 70 is a single strand of polypropylene suture that is looped into a three-circle configuration (a snowman configuration). When force is applied to the free ends 72, 74 of the plication mechanism 70, each of the circles in the three-circle configuration is contracted to remove the slack from the central portion of the support material 22. The ends 72, 74 for plication mechanism can be welded into a break pad, or are tied into a suitable knot to tension the support material 22 against the tissue of the urethra. The plication mechanism 70 may be removed from the support 22 by the surgeon after implantation if it is determined that the support material 22 is lying as desired over the tissue. In one embodiment, the plication mechanism 70 includes a conduit 71 provided to manage the loose ends of the plication suture.

Single Incision Male Sling—SIMS

One approach to attaching a support 22 in treating male urinary incontinence is made with reference to FIGS. 1 and 2. The patient is placed in gentle lithotomy position with buttock at the edge of the table. Insert a 14 French Foley catheter. A single (one and only one) incision (about 4-6 cm) is made vertically in the perineal tissue 1 cm anterior to the anus. The surgeon is instructed to dissect down to and isolate the ventral bulbous urethra keeping the bulbospongiosus muscle intact. The surgeon is instructed to expose the bulbospongiosus muscle and take down the central tendon 2 cm to provide urethral mobility and allow for sling re-approximation. The surgeon is instructed to dissect sufficiently to accommodate the entire support 22 and for incorporation of a wound retractor.

The system 20 is appropriate both for use in procedures where the surgeon dissects the bulbous spongiosis muscle and in procedures where the surgeon does not dissect the bulbous spongiosis muscle, as depends upon surgeon preference.

One of the anchors 42 is loaded into a bore of one of the introducers 28a, 28b by following the arrow provided on the tab 40. The tab 40 is removed and discarded after the anchor 42 is inserted into the bore of the introducer 28. The anchors 42 are placed in the obturator foramen following a trans-obturator (TO) path that is referred to as a TO approach. The introducer 28 is directed through the incision using an inside-out technique to guide the anchor 42 through the membrane over one of the left or right obturator foramen. Start the introducer 28 passage about 2 finger breadths (approximately 4 cm) below the pubic arch. The shaft of the introducer 28 should be parallel with the ipsilateral ischial pubic ramus. Using the thumb, push the introducer 28 posterior past the ischial pubic ramus, advancing through the obturator membrane until a pop is felt. Once the "pop" is felt, rotate an additional ¼ turn (thumb slide should be facing up). The introducer 28 and the anchor 42 in the introducer 28 may be repositioned as desired by the surgeon until the anchor 42 is physically expelled from the introducer 28. The surgeon is instructed to deploy anchor using thumb advance 56. The anchor 42 is inserted into the obturator externus muscle. The surgeon is instructed to withdraw the introducer 28, pull on the suture 24 to seat the anchor 42 in the tissue, and ensure integrity of the anchoring.

In a similar manner on the contralateral side, a second of the anchors 42 is loaded into the introducer 28, and introducer 28 is directed through the incision to guide the anchor 42 through the membrane over the other left or right obturator foramen for insertion into that obturator externus muscle.

The surgeon is instructed to center the support 22 on the bulbospongiosus muscle, using a stay suture if desired. The surgeon is instructed to retract the catheter from the glans penis. The surgeon is instructed to remove the conduit 29 from the suture 24 and to separate suture ends by pulling apart the break pad 30. The surgeon is instructed to tie a double overhand knot on both TO sutures to secure the support 22 down onto tissue, taking care to keep the support 22 centered. The surgeon is instructed to drive the knot down towards the anchor 42, keeping the support 22 centered, to firmly secure the posterior portion of implant for optimum urethral re-approximation. The surgeon is instructed to tie additional overhand knots to lock the support 22 in place, followed by trimming and discarding the removed excess suture. In this configuration, the base 60 of the support 22 is suspended by the suture 24, with each suture 24 connected to an anchor 42 that is engaged in the muscle of one of the opposing obturator foramen. The surgeon selects the amount of tension desired in the lateral suspension supporting the base 60, for example by tying a suitable knot in the suture 24 to fixate the base 60.

The arms 62, 64 are lifted to tension the support 22 against the bulbous spongiosis muscle. While holding the arms 62, 64 in tension, a third anchor is loaded into the introducer 28, and the introducer 28 is directed through the incision to guide the anchor 42 under the periosteum tissue but above the bone. Specifically, the surgeon is instructed to place the tip of the introducer 28 perpendicular to the tissue and gently press down to contact the pubic bone, skive along bone aiming toward the patient's ipsilateral shoulder maintaining contact for approximately 1.5 cm, then allow the needle to rotate away from the bone, followed by pushing the anchor 42 approximately 1 cm farther. The introducer 28 and the anchor 42 in the introducer 28 may be repositioned as desired by the surgeon. The surgeon is instructed to deploy the anchor 42 from introducer 28 using the thumb advance 56 and counter rotate to withdraw the introducer 28 leaving the anchor 42 in the dense fibrous tissue of the periosteum. The surgeon is instructed to pull on the suture 24 to seat anchor 42 in the tissue to ensure integrity of the anchoring. The suture 24 attached to the anchor 42 is pulled and the anchor 42 turns or toggles to fully engage the anchor 42 in a sideways orientation relative to the line of entry of the introducer 28 in the periosteum tissue. The anchor 42 is engaged with the periosteum tissue to hold the support in tension against the urethral complex. The fourth anchor is loaded into the introducer 28, and introducer 28 is directed through the incision to guide the anchor 42 through into and under the periosteum tissue on the contralateral side of the pubic symphysis of the patient. The surgeon is instructed to remove the conduit(s) from the suture 24 followed by tying of a double overhand knot in the sutures 24 to hold the support 22 in compression against the urethra. The knots are tightened to secure and stretch anterior portion of the support 22 over the urethra to provide optimum compression. Tie additional knots to lock in place, trim and discard excess suture. The surgeon may perform flexible cystoscopy to ensure appropriate coaptation of the urethra is achieved.

In this approach, the support 22 is secured and suspended by the sutures 24 between the opposing obturator foramen and held in tension against the bulbous spongiosis muscle of the urethra by anchoring two anchors 42 in the periosteum tissue on opposed lateral sides of the pubic symphysis. If the surgeon decides that additional gathering of the support 22 over the urethra is desired, the surgeon will use the plication mechanism 70 to take up any slack in the mid-region of the support 22 to ensure appropriate elevation and support of the urethra.

Figure 3:
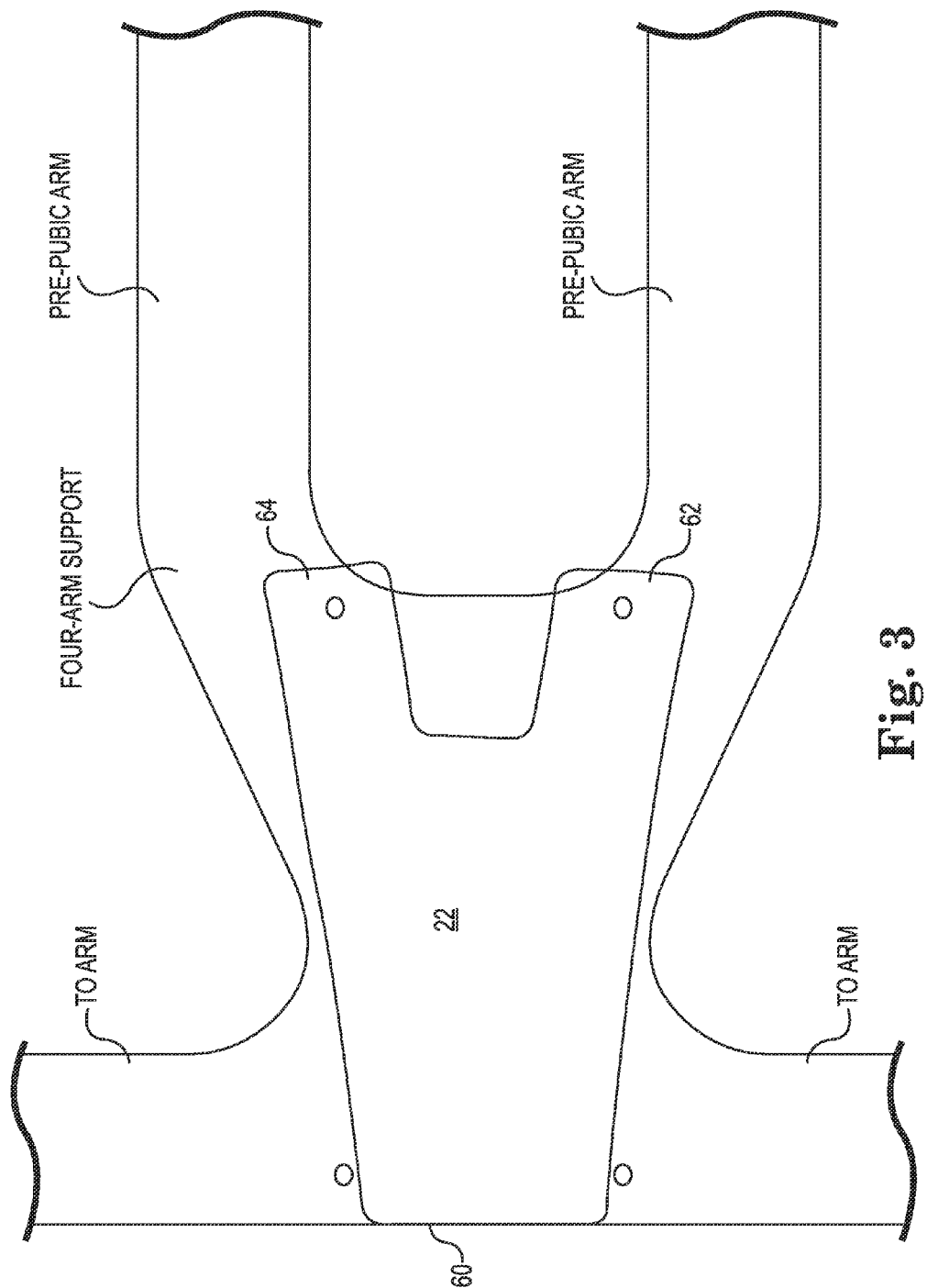
FIG. 3 is a top schematic view of the support material illustrated in FIG. 2 superimposed over a different support material.

FIG. 3 is a top view of the support material 22 superimposed over a four-arm support. In this example, the four-arm support has the shape of the Coloplast Virtue® Male Sling available from Coloplast Corp., Minneapolis, Minn. known to be useful in treating male urinary incontinence. The support material 22 has less material than this and other four-arm supports. The four-arm support includes a first transobturator arm (TO arm), a second TO arm, and a first pre-pubic arm opposite a second pre-pubic arm. The four-arm support has a lateral dimension extending along the TO arms of about 18 inches and a longitudinal dimension extending between the pre-pubic arms of about 12 inches. In contrast, the support material 22 has a base 60 with a width or base dimension of between 0.5 inches to 1.25 inches, which is much smaller (about 17 inches smaller) than the material between the first and second TO arms of the four-arm support. The first and second pre-pubic arms 62, 64 of the support material 22 extend between 2-3 inches, which is much shorter than the 12 inch extent of the pre-pubic arms provided by the four-arm support. It has been found that the relatively smaller support material 22 supports the male urethra as well as the larger four-arm support when implanted through a single incision and when secured by the anchors 26 and the system 20 described in this disclosure.

Figure 4:
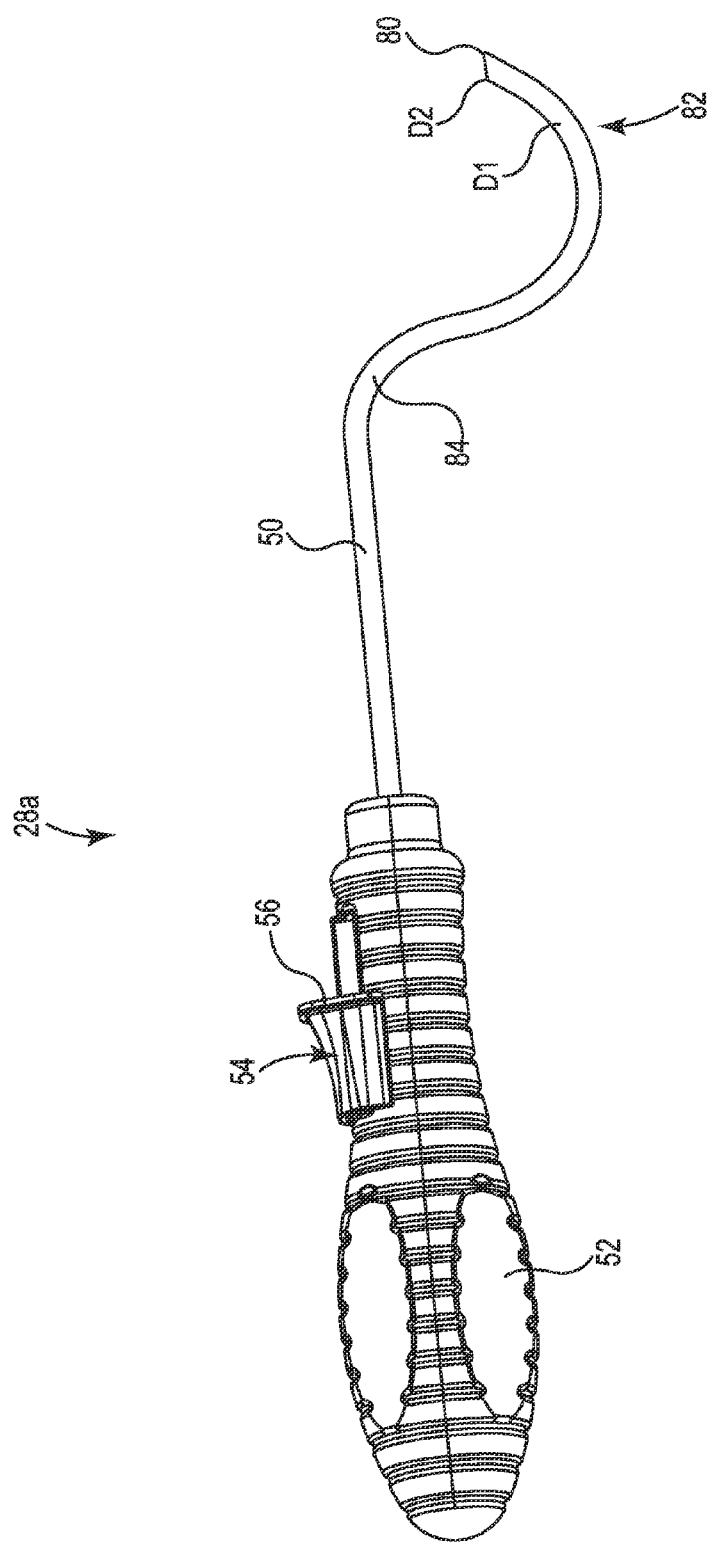
FIG. 4 is a perspective view of one embodiment of the introducer illustrated in FIG. 1.

FIG. 4 is a perspective view of the introducer 28a. The cannula 50 extends from the handle 52 and terminates in an end 80. The button 56 of the ejection mechanism 54 is located on the handle. In one embodiment, the button 56 is curved in an arc that extends over an exterior portion of the handle 52, which allows the surgeon to manipulate the button 56 when using the introducer 28 for placement of the anchor 42 in either a transobturator pass (deploying the anchor in TO tissue) or a pre-pubic pass (deploying the anchor in periosteum tissue). That is to say, when the introducer 28 is employed in a transobturator pass (e.g., either the right-hand side or left-hand side of the patient) the button 56 is conveniently located for operation by the thumb of the surgeon. When the introducer 28 is then employed in a pre-pubic pass for placing pre-pubic arms, the extended and sculpted button 56 is likewise conveniently and ergonomically located for one-handed operation by the surgeon.

The end 80 is formed on an end portion 82 of the cannula 50. In one embodiment, the end portion 82 of the cannula 50 is formed to have a constant outside diameter. In one embodiment, the end portion 82 of the cannula 50 is formed to have a tapering outside diameter that tapers from a first diameter D1 to a second diameter D2, where diameter D2 is less than diameter D1.

In one embodiment, the ejection mechanism 54 includes a wire/rod located inside of the cannula 50 and connected to the button 56. Movement of the button 56 moves the wire/rod within the cannula 50. When the anchor 42 (FIG. 1) is inserted into end 80 of the cannula 50, movement of the button 56 in a distal direction ejects the anchor 42 in a distal direction out of the cannula 50.

The cannula 50 may be straight or curved.

In one embodiment, the end portion 82 is formed as a circular arc all within the same plane such that the end portion 82 is neither helical nor spiral.

In one embodiment, the end portion 82 is formed as a circular arc in a helical spiral. For example, the end portion 82 extends between a first segment 84 and the end 80, and the helical spiral of the end portion 82 is formed such that the end 80 is located a distance distal outward and away from the first segment 84.

Figure 5:
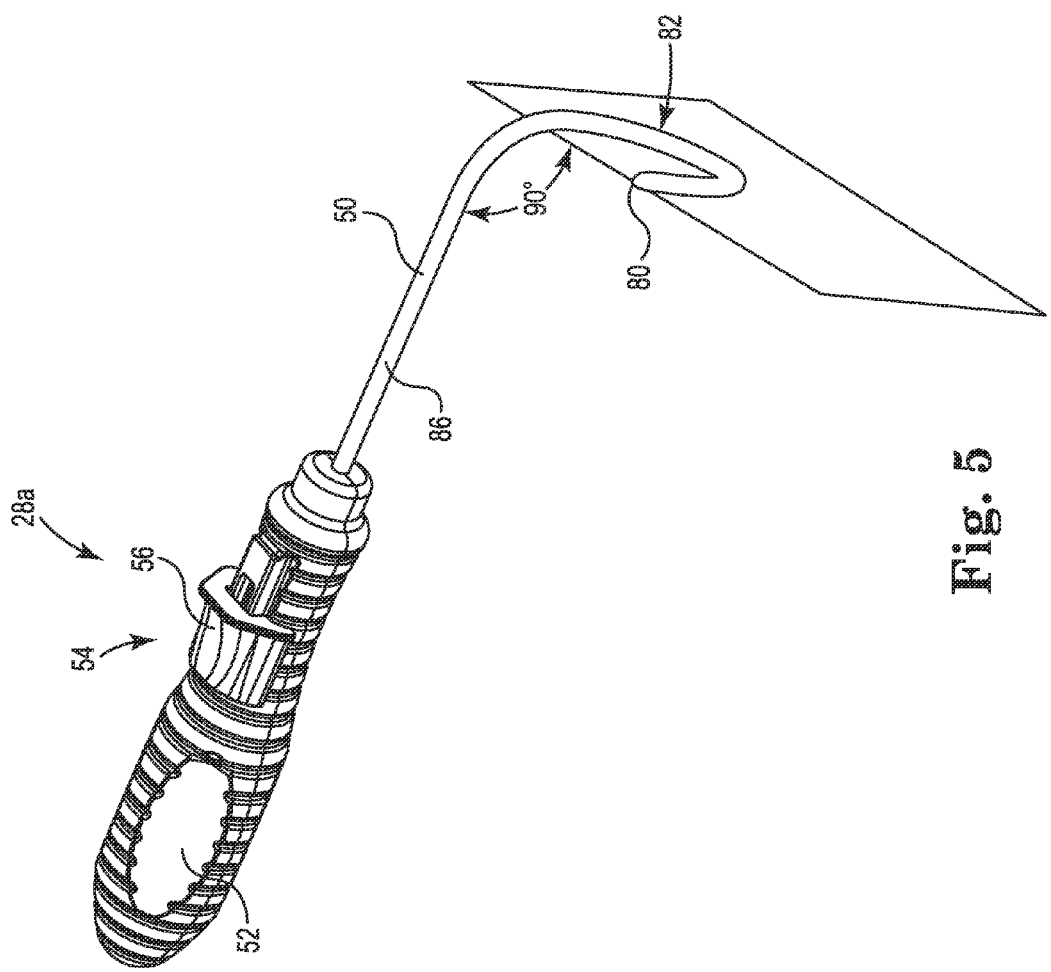
FIG. 5 is a perspective view of the introducer illustrated in FIG. 4.

FIG. 5 is a perspective view of one embodiment of the introducer 28a where the end portion 82 is formed as a circular arc within the same plane P. In one embodiment, the end portion 82 is oriented 90 degrees relative to a straight segment 86 of the cannula 50.

Figure 6:
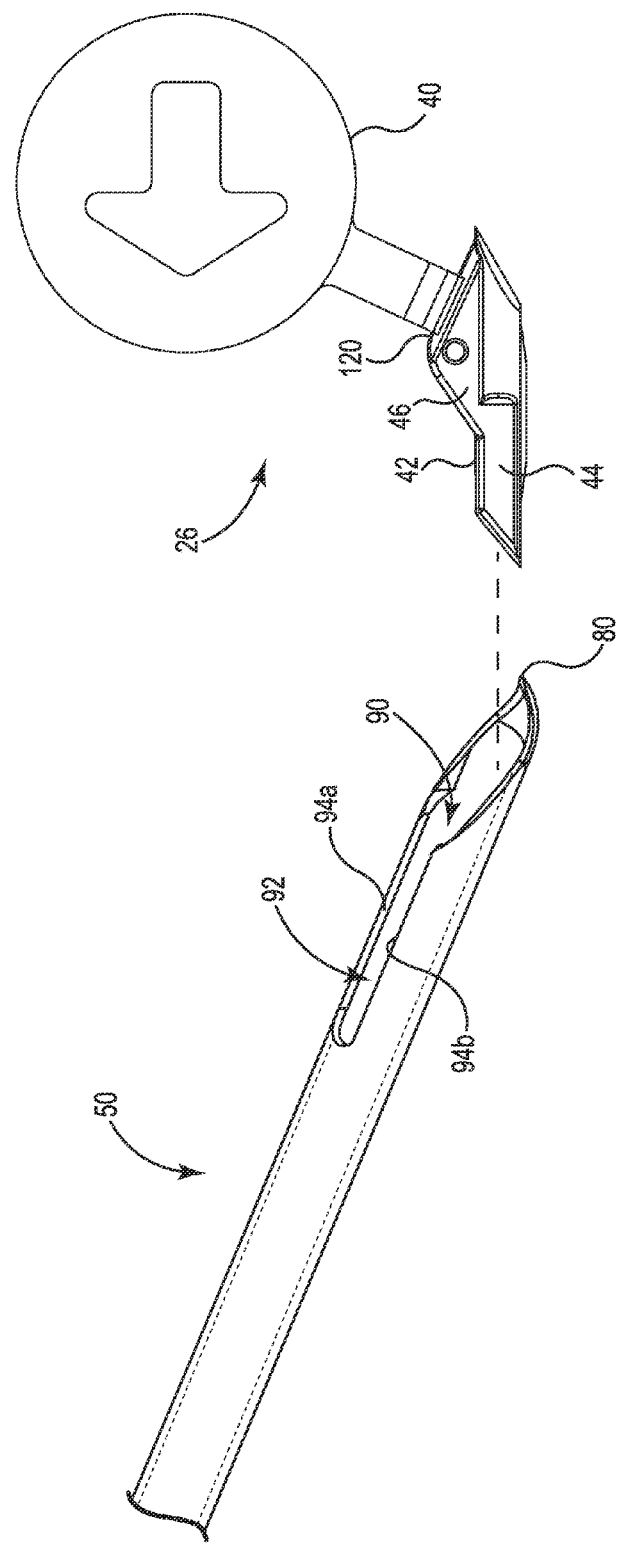
FIG. 6 is a perspective view of an end portion of a cannula of the introducer illustrated in FIG. 4.

FIG. 6 is a perspective view of one embodiment of the cannula 50 prior to inserting the anchor 42. The cannula 50 includes a bore 90 that is sized to receive the body 44 of the anchor 42 and a slot 92 that is sized to receive the tissue engagement fin 46 of the anchor 42. In one embodiment, the end 80 of the cannula 50 is bent inward toward the bore 90 to form an ejection ramp that is akin to a ski ramp on a ski jump. In one embodiment, the end 80 of the cannula 50 forms a point that is bent inward, where the point is on a side of the cannula 50 opposite from a location of the slot 92. The bent end 80 provides several advantages, including preventing the cannula 50 from digging into bone when the cannula 50 is inserted under periosteum tissue and encouraging the anchor 42 to lift and toggle away from the cannula 50 when the anchor 42 is ejected from the cannula 50. In one embodiment, the bore 90 is a circular bore having a substantially constant inside diameter. Other geometries are acceptable for the shape of the bore 90.

In one embodiment, the slot 92 is provided with side walls 94a, 94b that are parallel one relative to the other. The anchor 42 is relatively small compared to the human hand. The tab 40 is provided to allow the healthcare worker to handle the anchor 42 and insert the anchor into the cannula 50. After the body 44 of the anchor is inserted into the cannula 50, the tab 40 is snapped off from the anchor 42. The tab 40 is discarded. The body 44 of the anchor 42 is sized to frictionally engage with the bore 90 and the tissue engagement fin 46 is sized to frictionally engage with the slot 92 such that the anchor 42 does not fall out of the cannula 50 until actively and intentionally ejected by the surgeon operating the ejection mechanism 54 (FIG. 5).

It is desirable to frictionally engage the anchor 42 into the cannula 50 of the introducer 28. The geometry of the bore 90 and the slot 92 can be modified to encourage the frictional engagement between the cannula 50 and the anchor 42.

FIG. 7 is a top view, FIG. 8 is a side view, and FIG. 9 is an end view of one embodiment of a cannula 51 having a tapered outside diameter and a tapered slot 92'.

FIG. 7 is a top view of the cannula 51 having a slot 92' modified to increase frictional engagement with the anchor 42 illustrated in FIG. 1.

FIG. 7 illustrates one embodiment in which the slot 92' is tapered. The slot 92' is tapered by having the side walls of the slot 92' tapered at an angle T. In one embodiment, the angle T is 4 degrees and the side walls converge the width of the slot 92' from 1.1 mm down to 0.890 mm. The tapered slot 92' ensures positive engagement with the anchor 42. In this example, the inside diameter of the bore 90' is 1.6 mm and the outside diameter of the cannula is 2.2 mm.

FIG. 8 is a side view of the cannula 51, and FIG. 9 is an end view into the bore of the cannula 51. In one embodiment, the outside diameter of the cannula 51 is tapered from a first outside diameter OD1 measured at a proximal portion down to a second outside diameter OD2 measured at a distal portion, where the first outside diameter OD1 is larger than the second outside diameter OD2. The pointed end of the cannula 51 is not bent to provide the ski slope that is provided by the cannula 50 (FIG. 6).

Figure 10A:
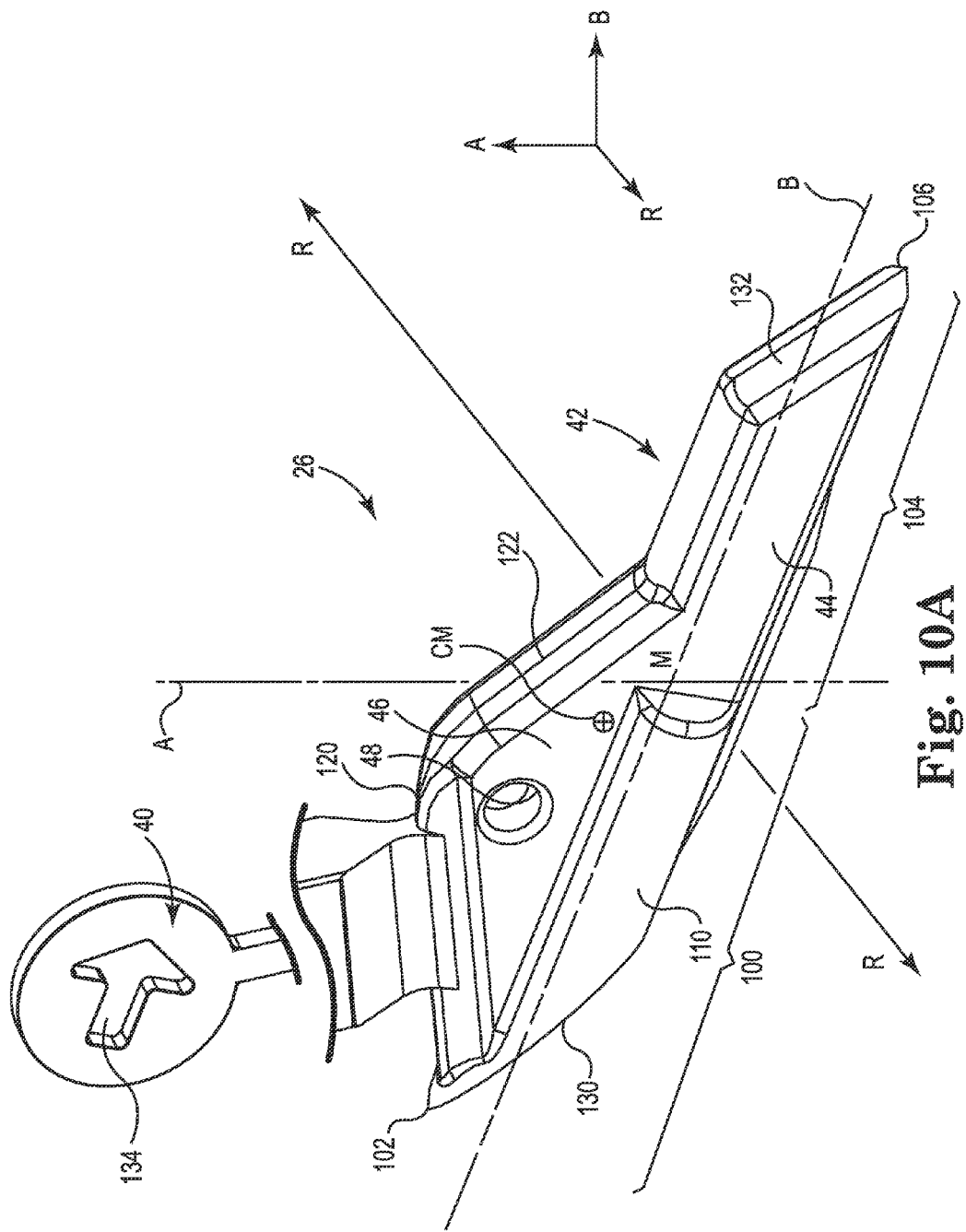
FIG. 10A is a perspective view and FIG. 10B is a side view of one embodiment of the anchor assembly illustrated in FIG. 1.
Figure 10B:
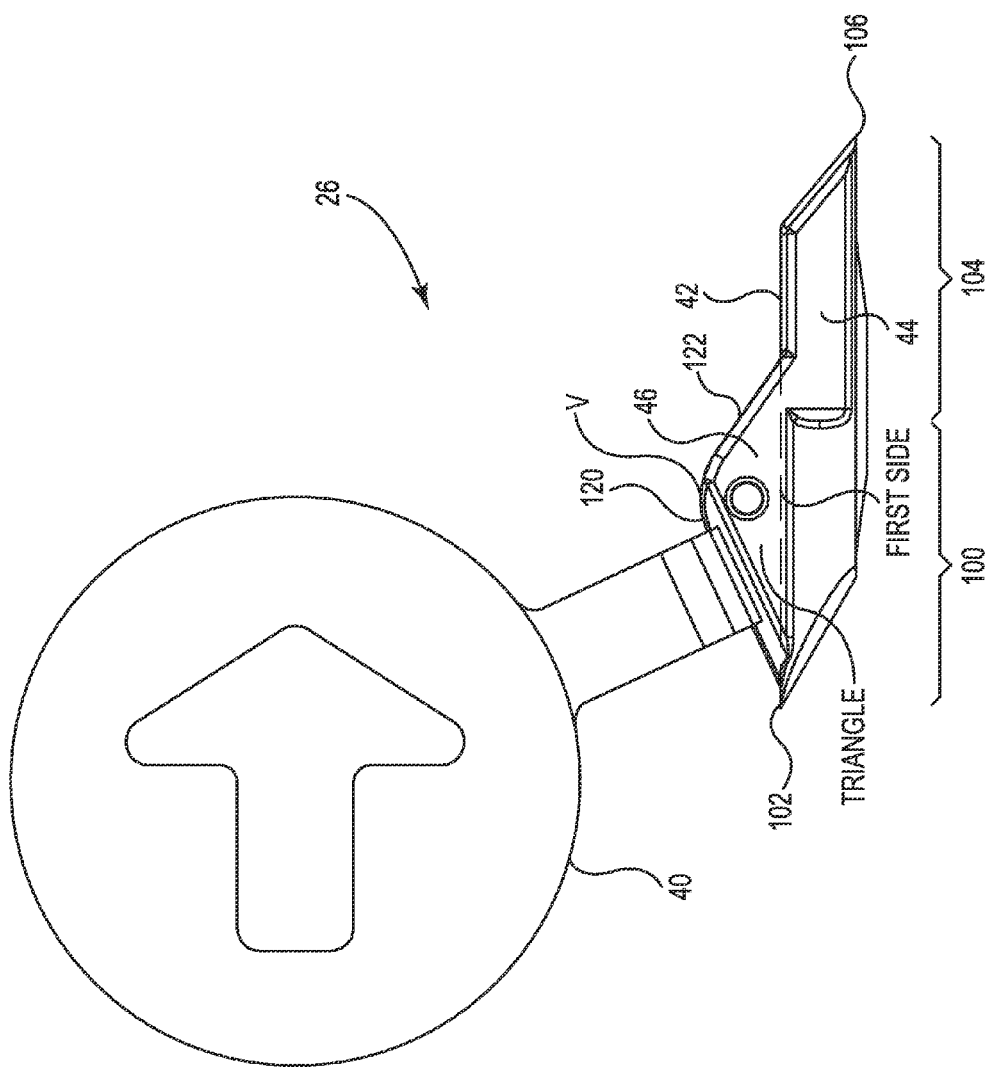

FIG. 10A is a perspective view and FIG. 10B is a side view of the anchor assembly 26. The anchor 42 of the anchor assembly 26 includes a longitudinal midpoint M located in the middle of the length of the anchor 42 as measured on the longitudinal axis B between ends 102, 106. A leading end portion 100 of the anchor 42 extends from the midpoint M to a leading end 102, and a trailing end portion 104 extending from the midpoint M to a trailing end 106. The leading end portion 100 is connected to the trailing end portion 104 at the midpoint M. A vertical axis A bisects the length of the anchor between the leading end 102 and the trailing end 106 and thus intersects the midpoint M.

The anchor 42 has a geometric asymmetry where the anchor 42 has more area on the leading end portion 100 (i.e., the left-hand side of the axis A) then on the trailing end portion 104 (i.e., the right-hand side of the axis A). The anchor 42 also has an asymmetric distribution of mass relative to the axis A. In one embodiment, a longitudinal central axis B is drawn and intersects the vertical axis A. In one embodiment, the mass distribution of the anchor 42 is asymmetric relative to the axis A (i.e., weighted more to the leading end portion 100) and is also asymmetric relative to the axis B (i.e., weighted more above the axis B). In this example, the center of mass CM is forward of the axis A toward the end 102 and above the axis B. The center of mass CM of the anchor 42 is not necessarily located at the geometric midpoint M.

The tissue engagement fin 46 is located asymmetrically on the anchor 42 relative to the midpoint M. In one embodiment, the tissue engagement fin 46 is located along the leading end portion 100 of the anchor 42 to provide the anchor 42 with a geometric asymmetry associated with the leading end portion 100. In one embodiment, the anchor 42 includes a barrel 110 located on the leading end portion of the anchor 42 to provide the anchor 42 with an asymmetric mass distribution relative to the midpoint M. The barrel 110, in combination with the tissue engagement fin 46, contribute to a distribution of mass for the anchor 42 that is predominantly distributed forward in the anchor 42, for example along the leading end portion 100. The barrel 110 and the eyelet 48 provided in the tissue engagement fin 46, in cooperation with the asymmetric forward-biased mass distribution, allow the anchor 42 to toggle, or turn, to move to ensure engagement when inserted into tissue.

The tissue engagement fin 46 includes a leading edge 120 and a trailing edge 122, and the anchor 42 includes a leading surface 130 located on the leading end portion 110 and the trailing surface 132 located on the trailing end portion 104. In one embodiment, the insertion tab 40 is removably secured to the leading edge 120 of the tissue engagement fin 46. The insertion tab 40 includes a marker or other indicia 134 to provide visual guidance to the surgical staff that is useful when loading the anchor assembly 26 into the cannula 50 of the introducer 28 (FIG. 1). After the body 44 and the barrel 110 of the anchor 42 are inserted into the cannula 50 of the introducer 28, the insertion tab 40 is disconnected from (snapped off) from the anchor 42. The anchor 42 is retained within the cannula 50 and prepared for insertion into tissue.

FIG. 10B illustrates one embodiment in which the tissue engaging fin 46 is triangular with a first side integrated in the leading end portion 100 of the body 44, a leading side (e.g., leading edge 120) connected between the leading tip 102 and a vertex V, and a trailing side (e.g., trailing edge 122) connected between the vertex V and the trailing end portion 104 of the body 44, with the vertex V located off of the longitudinal axis B.

When the anchor 42 is inserted into tissue, the surgeon is instructed to provide a pulling force to the suture 24 (FIG. 1) that is engaged with the eyelet 48, and this pulling force rotates the anchor 42 to engage the leading edge 120, the trailing edge 122, and the trailing surface 132 in a stable position within tissue.

The anchor 42 is both geometrically asymmetric and has an asymmetric mass distribution, both which encourage the anchor 42 to turn by which the leading end 102 is rotated in a clockwise (for example) manner to engage the edges 120, 122, and surface 132 with the tissue. The anchor 42 is configured for insertion into periosteum tissue that covers bone. The bone provides a backstop or a hard surface that prevents the anchor 42 from penetrating into the bone. The bone, however, also provides a surface that might discourage the rotation or toggle in of the anchor 42 since the bone is substantially immovable. It has been discovered that the geometric asymmetry and the asymmetric mass distribution of the anchor 42 is well-suited to allow the anchor 42 to turn and toggle in a short distance as the surgeon applies a pulling force to the suture that is engaged with the eyelet 48. Other anchors having a geometric symmetry and a geometric mass distribution have been found to not turn, or turn less slowly and over a greater distance, which can have the effect of the anchor not fully engaging with the tissue and possibly having the anchor pull out of or exit its insertion point into the tissue. In contrast, the anchor 42 has been discovered to provide rapid turning and toggling that provides excellent tissue engagement over a short engagement distance as the surgeon provides force to the suture 24 that is engage with the eyelet 48.

FIG. 11 is a perspective view of the anchor assembly 26 oriented to illustrate a crush rib 140 located along a lower edge of the anchor 42 on a side opposite from the tissue engagement fin 46. In one embodiment, the crush rib 140 extends from the leading end portion 100 back to the trailing end portion 104. One suitable height of the crush rib 140 is in a range from 0.5-4 mm, preferably from 1-3 mm. The crush rib 140 is provided to ensure a positive frictional engagement of the anchor 42 with the cannula 50 (FIG. 1) of the introducer 28. The crush rib 140 is deformable and configured to be pressed in toward the body of the anchor 42 when the anchor 42 is inserted into a cannula. The crush rib 140 occupies any excess space inside of the cannula, with the excess material of the crush rib 140 compacted to fit inside the cannula in a friction-fit manner. The 1-3 mm height of the crush rib 140 allows the rib to be compacted-to-size as it is inserted into the cannula.

Suitable materials for fabricating the anchor assembly 26 include polymers in general, metal and metal alloys, composites, composites reinforced with fibers, and other materials suitable for molding or extrusion. In one embodiment, the anchor assembly 26 is fabricated from polypropylene. Other polyolefins or polymers are suitable.

The anchor 42 of the anchor simply 26 has a length extending from the leading end 102 to the trailing end 106 in a range from 2-30 mm, preferably 5-25 mm, and more preferably 10-20 mm. One suitable anchor length has been determined to be about 11 mm from the leading end 102 to the trailing end 106.

FIG. 12 is a side view of the anchor assembly 26, FIG. 13 is a bottom view of one embodiment of an anchor assembly 226, and FIG. 14 is a side view of one embodiment of an anchor assembly 326. The anchor assembly 26 provides the insertion tab 40 removably connected to the leading edge 120 of the anchor 42. The anchor assembly 226 includes a perpendicular insertion tab 240 secured to a side surface of the anchor 42. The anchor assembly 326 includes an insertion tab 340 located on the trailing edge 122 of the anchor 42. The exterior surface of the insertion tabs 40, 240, 340 can include a textured gripping surface such as a stippled surface or another suitably structured surface that increases friction when the surgical staff handles the anchor assembly with the gloved hand.

Figure 16:
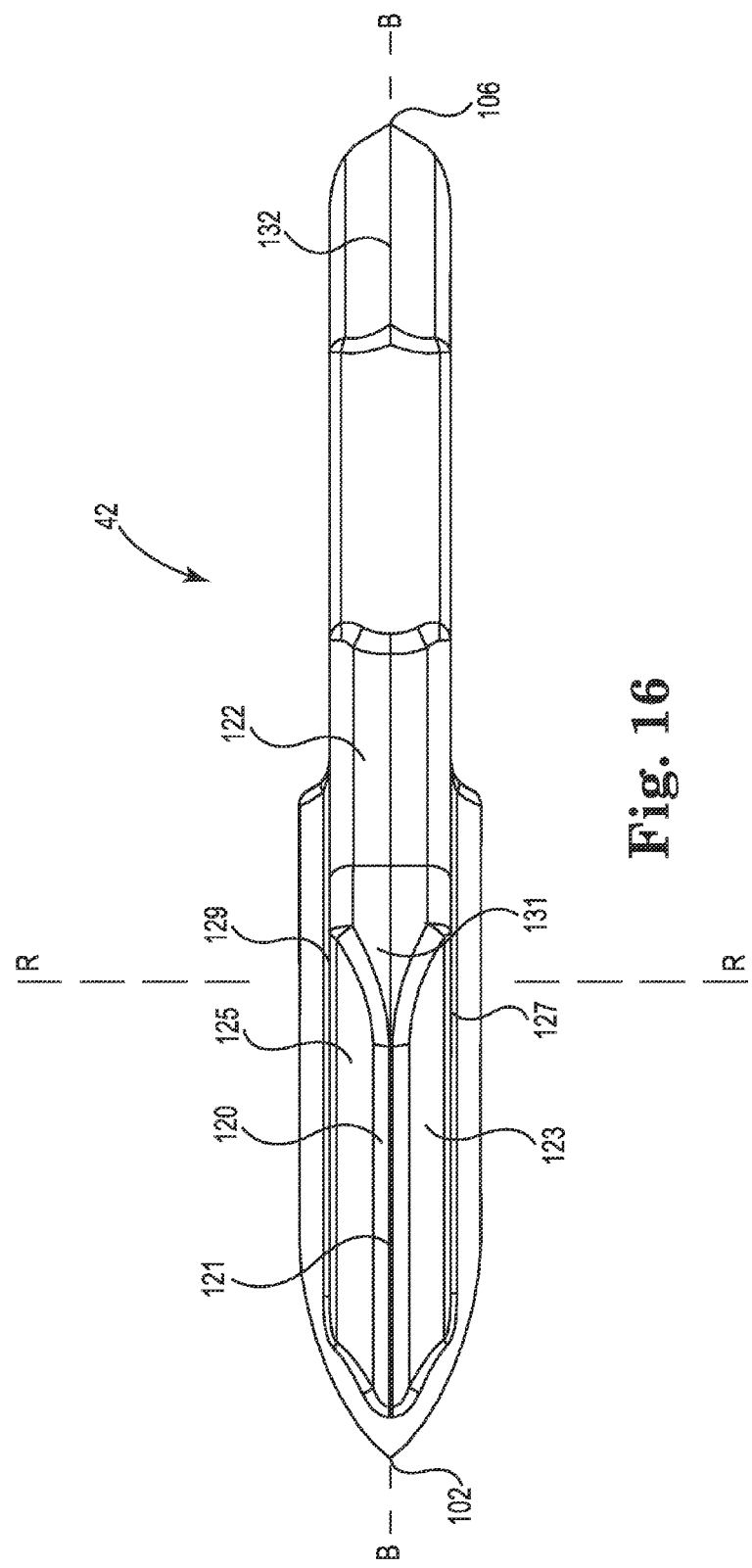

FIG. 15 is a perspective view, FIG. 16 is a top view, and FIG. 17 is a bottom view of the anchor 42 without the insertion tab 40. The leading edge 120 tapers to converge to a line 121 or narrow surface 121 that allows the anchor 42 to more easily penetrate tissue.

The tissue engaging fin 46 extends away from the body 44. In one embodiment, the tissue engaging fin 46 has a triangular shape with a longest side X of the triangle parallel with the longitudinal axis B-B of the anchor 42, and shorter sides Y and Z meeting at an angle F, the three sides X, Y, Z of the triangle defining a geometry of the tissue engaging fin 46.

The tissue engaging fin 46 is configured to grab in tissue and encourage the anchor 42 to rotate for stabile engagement and anchoring within tissue. One embodiment provides the tissue engaging fin 46 with a uniform width or thickness. In one embodiment, the interior portions of the triangle X-Y-Z are scalloped or thinned, such that the perimeter of the triangle X-Y-Z is thicker in width than the area inside of the triangle X-Y-Z.

The crush rib 140 extends longitudinally along a portion of the bottom surface of the anchor 42. The crush rib 140 is provided as a radially extending flange, where the flange has a width ranging between 0.1-0.5 mm and a height in a range from 0.5-4 mm, preferably from 1-3 mm. In one embodiment, the crush rib 140 includes a tapering leading edge and a tapering trailing edge. The crush rib 140 is useful in retaining the anchor 42 in the cannula 50 of the introducer tool 28 (FIG. 1) until deployment of the anchor 42 is initiated. The crush rib 42 is sufficiently deformable when it is engaged with cannula 50 to allow the anchor 42 to be press-fit into the cannula 50 while also allowing the anchor 42 to be ejected from the tool.

FIG. 16 is a top view of the anchor 42. The leading edge 120 tapers to converge to the line 121 or ridge 121.

In one embodiment, the leading edge 120 tapers or slopes from a pinnacle or vertex V of the anchor 42 towards the body 44 and the trailing edge 122 tapers or slopes from the vertex/pinnacle of the anchor 42 towards the body 44. In one embodiment, the leading edge 120 includes sloping surfaces 123, 125 extending from the line 121 toward first and second side surfaces 127, 129 of the tissue engaging fin 46. The line 121 and the sloping surfaces 123, 125 of the leading edge 120 are configured to facilitate easy cutting or piercing through tissue during insertion and rotation of the anchor 42 in the tissue. The configuration of the leading 120 including the 121 and the sloping surfaces 123, 125 provides the leading edge 120 with a reduced thickness (width) relative to a thickness of the fin 46 at the first and second side surfaces 127, 129, which aids the fin 46 in sliding through or piercing tissue.

In one embodiment, a top portion 131 of the tissue engaging fin 46 has a generally cusped configuration with a base of the cusp located towards the trailing edge 122 of the fin 46 and with the two sides of the triangle meeting on the line 121 of the leading face 52. The cusped top portion 131 is configured to help provide a smooth transition of the leading edge 120 between the line 121 and the first and second side surfaces 123, 125.

In one embodiment, the trailing edge 122 of the tissue engaging fin 46 has a blunt configuration and can include a planar surface. The trailing edge 122 is configured to provide increased engagement with tissue such that the anchor 42 has improved resistance against extraction from tissue once it is in implanted in position.

With reference to FIG. 17, the leading surface 120 of the anchor 42 is integrated to and angles away from the barrel 110 to terminate at the leading end 102. The bottom view of the anchor 42 illustrates that the leading surface 130 is heart-shaped as the wider barrel 110 tapers to the leading end 102.

In one embodiment, a width W3 of the tissue engaging fin 46 corresponds to the width W2 of the trailing end portion 104 of the body 44. In one embodiment, the width W3 of the tissue engaging fin 46 is greater along one or more of the sides X, Y, Z of the triangular shape (FIG. 15) than at positions defined within the triangular area. That is to say, in one embodiment a wall thickness of the tissue engaging fin 46 is thinner "inside" the triangle's bounds than at one or more of the edges of the triangular shape.

In one embodiment, the tissue engaging fin 46 is superposed over the leading end portion 100 of the body 44 including the protruding barrels 110. The protruding barrels 110 are formed as a pair of radial barrels 110 extending from the body 44 in a radial direction perpendicular to the direction of the fin 46.

In one embodiment, the tissue engaging fin 46 is offset towards the leading end 102 relative to the mid-point M of the body 30 (located on axis A-A in FIG. 10). In one embodiment, the tissue engaging fin 46 locates asymmetric to the mid-point M. In one embodiment, the tissue engaging fin 46 is offset such that an entirety of the tissue engaging fin 46 is located on leading end portion 100. In one embodiment, a majority but less than an entirety of the tissue engaging fin 46 locates on leading end portion 100. In one embodiment, the mid-point M of the body 44 locates at a transition between the leading end portion 100 and the trailing end portion 104. In one embodiment, the eyelet 36 for receiving a length of suture extends through the entire width W3 of the tissue engaging fin 46.

FIG. 18A is cross-sectional view of the leading end portion 100 of the anchor 42 and FIG. 18B is cross-sectional view of the trailing end portion 104 of the anchor 42.

In one embodiment, the first and second protrusions 110 combine with the leading end portion 100 of the body to provide the tissue anchor 42 with a circular cross-section.

The tissue anchoring system 20 described above is useful for anchoring support material relative to tissue, particularly in treating urinary incontinence. Embodiments provide placing the anchor 42 in tissue, which can include ligaments, fatty tissue, connective tissue and other soft tissue in general. It has been discovered that support material useful in treating male urinary incontinence can be implanted through a single (one and only one) incision by employing the introducer 28 and the anchor 42 described in this specification in placement of the anchor 42 into periosteum tissue over the bone of the pelvis and other anchors in the membrane of the transobturator foramen.

One approach to attaching a support 22 in treating male urinary incontinence is made with reference to FIGS. 1 and 2. The base 60 of the support 22 is secured to the patient by engaging an anchor 42 in the obturator externus muscle of each obturator foramen and having the suture 24 extend from each anchor 42 to the support 22. In this manner, the support 22 is suspended between the opposing obturator foramen. The arms 62, 64 of the support 22 are lifted to tension the support against the bulbous spongiosis muscle, and while holding the arms 62, 64 in tension, two other anchors 42 are secured in the periosteum tissue, one on either side of the pubic symphysis of the patient. In this approach, the support 22 is secured and suspended by the sutures between the opposing obturator foramen and held in tension against the bulbous spongiosis muscle of the urethra by anchoring two anchors 42 between the periosteum tissue and the bone on opposed lateral sides of the pubic symphysis. The anchors 42 anchored between the periosteum tissue and the bone are placed as described below in FIGS. 19-21C.

Figure 19:
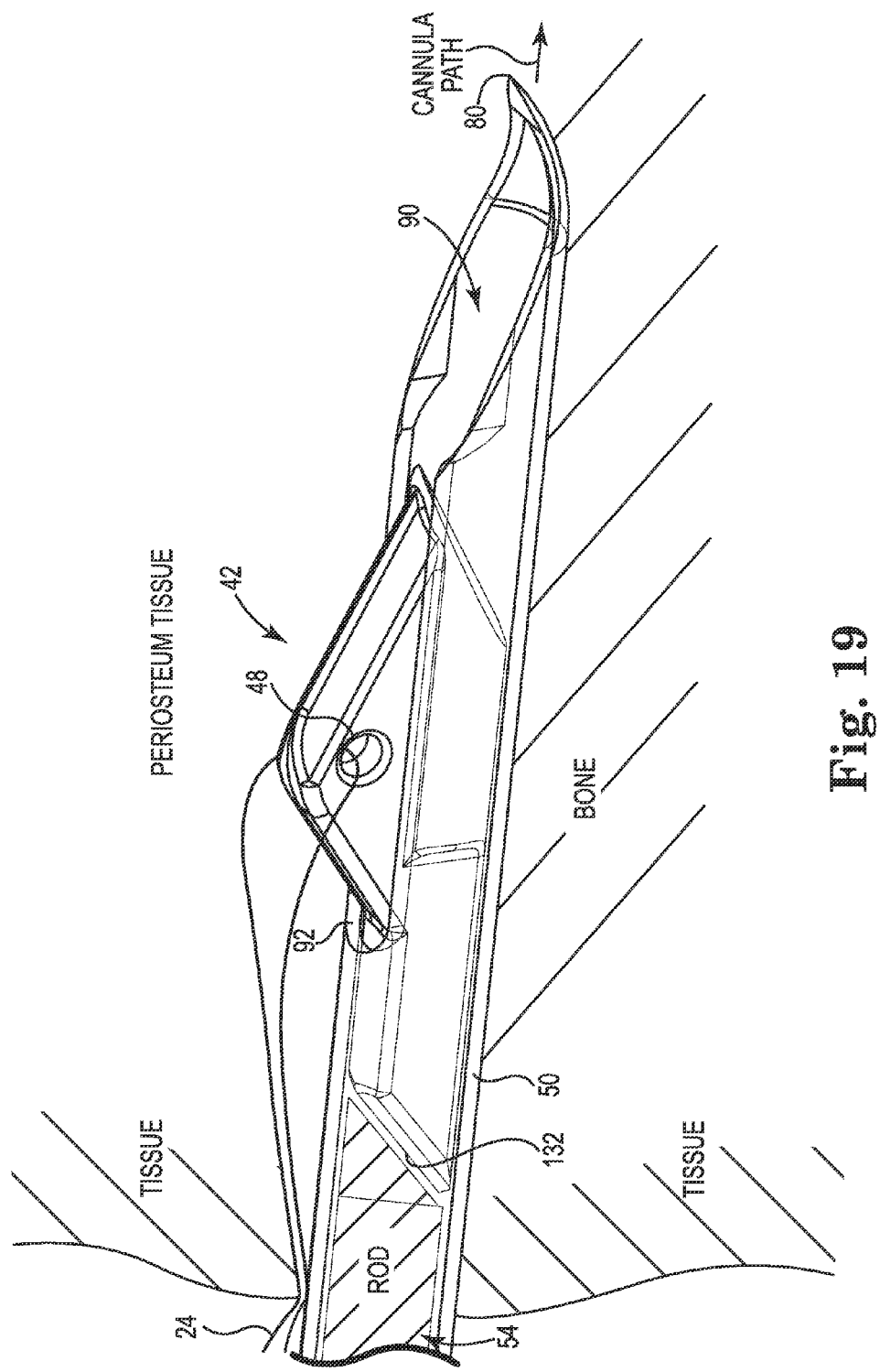
FIGS. 19-20 are perspective views of the anchor illustrated in FIG. 15 ejected into soft tissue from the cannula illustrated in FIG. 6.

FIG. 19 illustrates the cannula 50 of the introducer 28 inserted into soft tissue along a cannula path and guided along the bone of the pelvis and into periosteum tissue. Neither the cannula 50 nor the anchor 42 enter the bone. The anchor 42 has been inserted into the bore 90 and retained in the slot 92 with the insertion tab 40 (FIG. 1) removed. The suture 24 is engaged with the anchor 42 by the eyelet 48 and exits through the incision made in the tissue. In this manner, the surgeon has control of the anchor 42 by placing tension of the suture 24, and also by having the anchor 40 frictionally engaged within the cannula 50. In one embodiment, the end 80 of the cannula 50 is bent upward toward the bore 90 to reduce the possibility of the end 80 digging into or gouging the bone.

Figure 20:
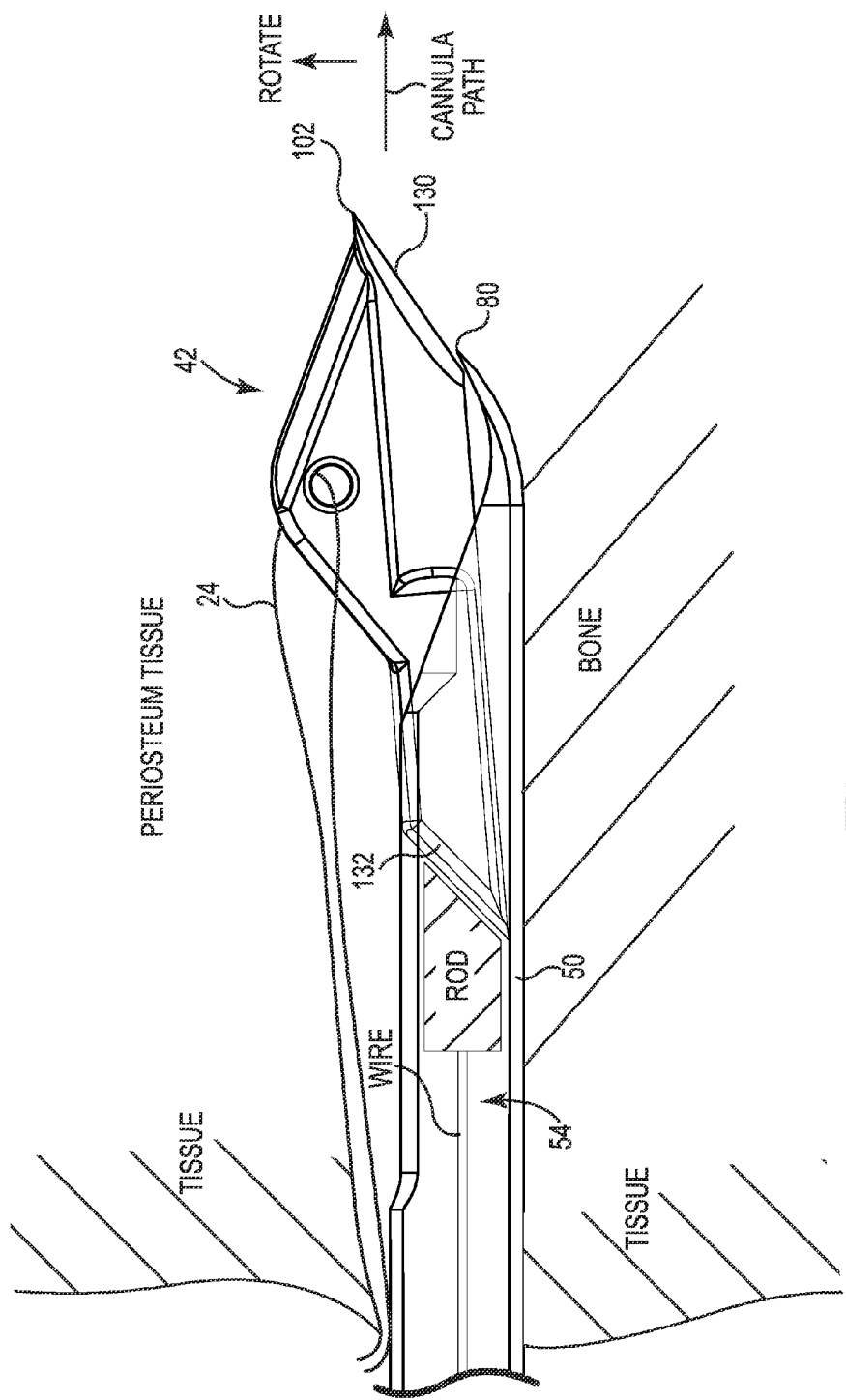

FIG. 20 illustrates the anchor 42 ejected a partial distance out of the bore 90 of the cannula 50 by the ejection mechanism 54. In one embodiment, the ejection mechanism 54 is a piano wire connected to the button 56, where the wire is stiff in axial compression and suited for pushing the anchor 42 out of the cannula 50 and yet flexible in a radial direction to allow the wire to negotiate the curvature of the introducer needle or cannula 50. Suitable ejection mechanisms 54 include piano wire, braided wires, or flexible cables fabricated of metal or plastic.

With additional reference to FIG. 1, the button 56 of the ejection mechanism 54 has been moved forward in a distal direction, which results in the wire pushing the rod forward in a distal direction. A surface of the rod pushes against the trailing edge 132 of the anchor 42 to eject the anchor 42 out of the cannula 50 and into the soft/connective tissue. The suture 24 and the proximal portion of the cannula 50 extend out of the incision toward the surgeon. The leading end 102 and the leading surface 130 of the anchor 42 are sized and configured to glide between the periosteum tissue and over the bone (but not into the bone surface). The bent end 80 of the cannula 50 prevents the cannula 50 from digging into the bone and lifts the anchor 42 away from the bone and begins rotation or toggling of the anchor 42. The bent end 80 of the cannula 50 provides a ramp 80, and movement of the anchor out of the cannula 50 cause the anchor 42 to rotate away from the cannula path.

Figure 21A:
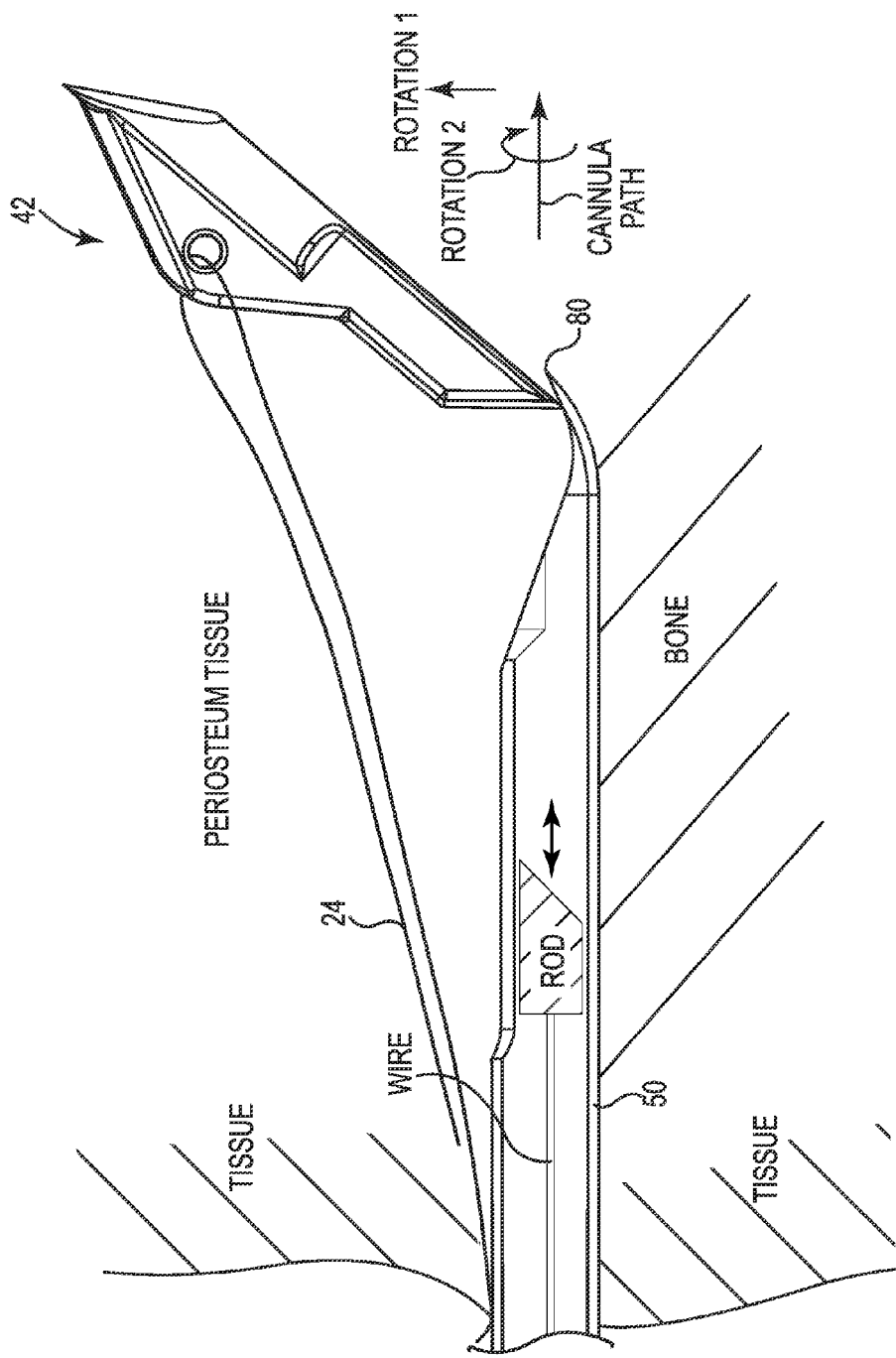

FIG. 21A illustrates the anchor 42 ejected out of the cannula 50. The bent tip 80 directs the anchor 42 in an upward direction into the periosteum tissue. The anchor 42 is rotated off of the cannula path (the anchor 42 is pitched upwards). In one embodiment, the anchor 42 has two rotational movements: one is rotated/pitched upwards off of the cannula path and the second is rotated (or rolled) on the longitudinal axis of the anchor 42. The cannula 50 is removed from the tissue after the anchor 42 has been ejected. The surgeon controls the orientation of the anchor 42 by maintaining control of the suture 24. The additional reference to FIG. 1, the suture 24 is engaged with the support material 22 and includes the flattened break pad 30.

FIG. 21B illustrates the cannula 50 has been removed from the tissue leaving the anchor 42 in the periosteum tissue above the bone. The suture 24 extends away from the anchor 42 out of the incision by the cannula and back toward the surgeon.

Figure 21C:
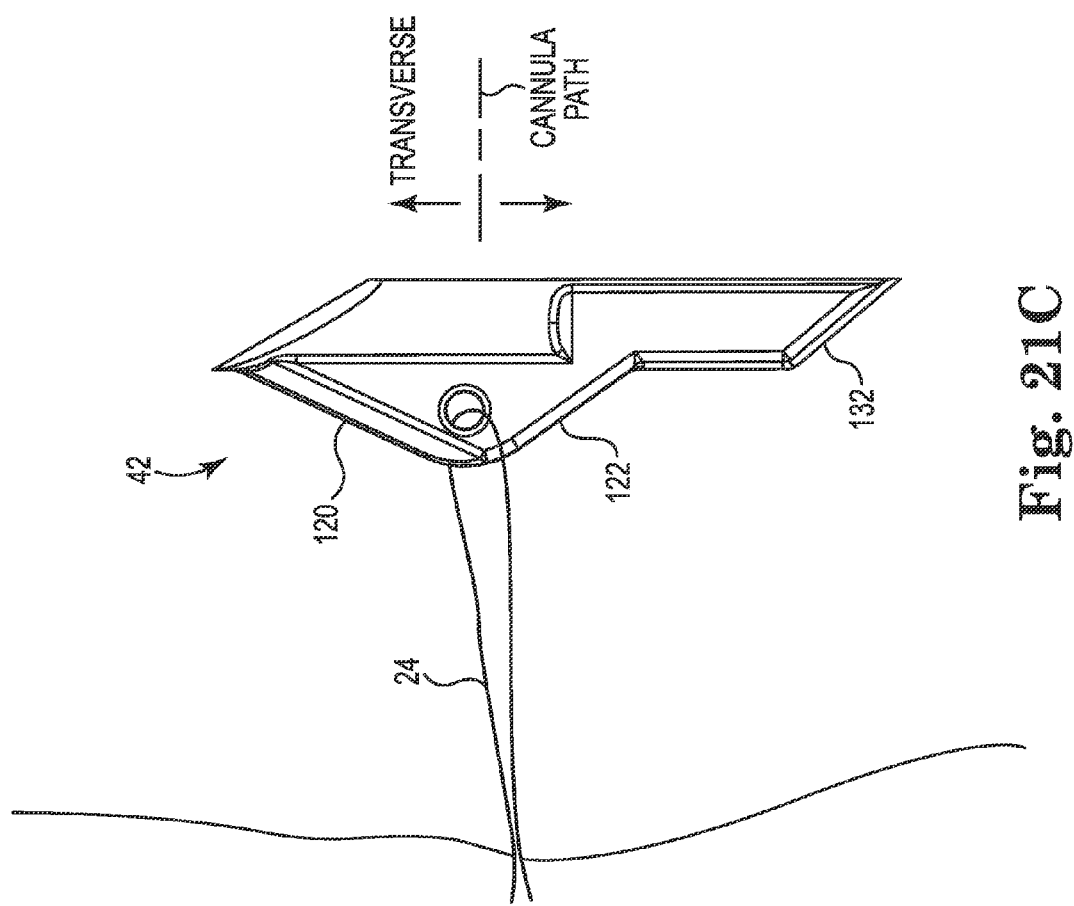

FIG. 21C illustrates a top view of the anchor 42 in an orientation after a pulling force has been applied to the suture 24. Pulling on the suture 24 in a direction away from the patient, rotates the anchor 42 to position a length of the anchor 42 transverse to the cannula path. The anchor 42 is engaged with the periosteum tissue over the surface of the bone; in this sense, the anchor 42 is between the bone and the surface of the skin, thus located in the periosteum tissue.

The surgeon has directed a pulling forced onto the suture 24 to rotate the anchor 42. The geometric asymmetry of the anchor 42 and the asymmetric mass distribution along the length of the anchor 42 encourages the anchor to rotate into a stable configuration in which the leading edge 120, the trailing edge 122, and the training surface 132 are engaged with tissue and resist further movement of the anchor toward the opening formed in the skin by the cannula 50. The surgeon has thus forcefully engage the anchor 42 in the periosteum tissue into an orientation in which the anchor resists displacement or movement. The suture 24 extends the anchor 42 to the support material 22 (FIG. 1). The anchor 42 is thus engaged with tissue and the suture 24 is engaged with the support material 22. The surgeon has control of the anchor 42 with the suture 24, and in preparation for tying a suitable suture knot separates the suture 24 into two free ends by breaking the break pad 30. The suture 24 is tied in a suitable knot to retain the support material 22 in the location desired by the surgeon.

It has been discovered that the anchor 42 engages with the periosteum tissue in such a forceful and durable manner that a polypropylene suture 24, as commonly employed in treating incontinence, will fail and snap before the anchor 42 disengages with the tissue. That is to say, the polypropylene suture 24 has been designed to be the weak link in the system 20 such that the anchor 42 will forcefully engage with periosteum tissue to allow the surgeon to apply as much force as desired and fixating the support material 22. The suture 24 will break before the anchor 42 can be pulled out of the tissue, which contributes to a superior anchoring connection. The surgeon is familiar with the amount of force that can be applied to polypropylene suture.

The procedure described above places the anchor and the periosteum tissue that covers the pelvis. The system 20 is suited for placing the anchor 42 in other locations, for example through the membrane of the obturator foramen. In such a procedure, the cannula is directed through the single incision formed in the patient, around the ischial pubic ramus and into the membrane covering the obturator foramen. One suitable such cannula includes the cannula 50 described in FIG. 5 having the curved section 82. The ejection mechanism 54 is employed to deploy the anchor 42 into the membrane or muscle formed over the obturator foramen. The suture 24 is employed to fully engage the anchor 42 in the tissue prior to the surgeon fixating the support material 22 by tying a knot and the suture 24.

One suitable method for placing an anchor into tissue includes directing the cannula 50 of the introducer 28 into the tissue; pushing the anchor 42 out of the cannula 50; removing the cannula 50 from the tissue and leaving the anchor 42 in the tissue; applying a pulling force to the suture 24 that is connected to the anchor 42 to engage the anchor 42 with the tissue; breaking the bond that is formed in the suture 24 at the break pad 30 to produce two free ends of the suture 24; and tying a knot in the suture 24 to fixate the anchor 42, or the anchor 42 and the support material 22, in position as desired by the surgeon and instructed in the instructions for use of the system 20.

One advantageous embodiment of the system 20 includes providing the surgeon improved control over when and where the anchor 42 is placed. For example, it is sometimes experienced that when an anchor is delivered into tissue by an introducer that the tissue has an insufficient ability to retain the anchor. This phenomenon is experienced when the needle is directed into fatty tissue, after which the surgeon realizes that the fatty tissue will be unable to appropriately retain the anchor for treating male incontinence. The system 20 provides a solution by allowing the surgeon to direct the cannula 50 into the tissue to determine if the tissue is suited for receiving the anchor, and allowing the surgeon to remove both the cannula 50 and the anchor 42 if the surgeon determines the tissue is not ideal for the application. The system 20 allows the surgeon to direct the cannula at another location in the tissue prior to ejecting the anchor 42 out of the cannula 50 with the ejection mechanism 54. The system 20 provides the surgeon improved control in that the anchor 42 does not leave the cannula 50 until the surgeon activates the ejection mechanism 54.

One suitable method of anchoring a support material for treating male urinary incontinence will now be described with reference to FIG. 1 in FIG. 2. A member of the surgical staff grasps the anchor assembly 26 by the insertion tab 40 and inserts the anchor 42 into the cannula 50. The insertion tab 40 is subsequently removed from the anchor 42. The suture 24 is engaged with the eyelet 48 of the anchor 42 and with the support material 22. The surgeon directs the cannula 50 to the tissue location of interest and ejects the anchor 42 by activating the button 56 of the ejection mechanism 54. The surgeon removes the cannula 50 from the tissue and applies a retraction force to the suture 24 that rotates and engages the anchor 42 with the tissue. The support material 22 is placed in the desired location, the break pad 30 is separated to provide the suture 24 with two free ends, and the surgeon fixates a support material 22 at the desired location. It should be noted that the surgeon also has the option to lightly tie a stay stitch to hold the support material 22 in place until the other anchors are deployed.

One application of the above method includes forming one and only one incision in the patient between the scrotum and the anus, and loading the anchor 42a into the cannula 50. The insertion tab 40 is separated from the anchor 42. The cannula 50 is inserted into the one and only one midline incision and directed into the membrane of the obturator foramen. The ejection mechanism 54 is manipulated to eject the anchor 42a into the membrane of the obturator foramen. The cannula 50 is removed, for example by following a pathway around a descending ramus and out of the incision. The base 60 of the support material 22 is located inferior to the bulbar urethra and a stay stitch is placed with the suture 24. A similar approach is employed on the contralateral side of the patient to place the anchor 42b in the opposing obturator foramen membrane. The surgeon ties the suture 24b to fixate the base 60 of the support material 22 at a location inferior to the bulbar urethra. With the support material 22 in its desired position, the surgeon returns to suture 24A, removes the stay stitch, and ties a permanent knot to fixate the base 60 of the support material 22.

The pre-pubic arms 62, 64 are elevated to a location superior to the base 60 and a mark is made on the tissue with a marking pen to identify the location of the pre-pubic arms 62, 64. It is desirable that the support material 22 elevates and compresses the tissue of the urethra, and in one embodiment the surgeon will place additional marks on the tissue at a location approximately 1 cm superior to each of the pre-pubic arms 62, 64 and 1 cm lateral and outside of each pre-pubic arms 62, 64 (i.e., the marks are "up and over" relative to the arms). A suitable cannula is selected, and the anchor 42c is loaded in the cannula. The cannula is directed into the periosteum tissue and the anchor 42c is ejected from the cannula into periosteum tissue above the surface of the bone of the pelvis. The cannula is withdrawn and a force is applied to the suture 24c to toggle and engage the anchor 42c within the tissue. With the pre-pubic arm 62 placed in its desired position the surgeon will lightly tie a stay stitch in the suture 24c. A similar approach will be employed on the contralateral side of the patient in which the anchor 42d is placed in the periosteum tissue by a cannula of the introducer, after which the cannula is removed and the anchor 42d is rotated or moved into engagement with the tissue by applying a force to the suture 24d. The pre-pubic arms 64 will be placed in its desired position according to the instructions for use provided with the system 20, and the surgeon will tie a permanent knot to fixate the pre-pubic arm 64. The surgeon confirms the location of the placement of the pre-pubic arm 62, loosens the stay stitch in suture 24c, and ties a permanent knot in the suture 24c to fixate the pre-pubic arm 62. In this manner, the pre-pubic arms 62, 64 are separated away from the base 60 and fixated to elevate and compress the support material 22 against the urethra. If desired by the surgeon, the plication mechanism 70 is adjusted to remove slack from a central region of the support material 22 after the base 60 and the pre-pubic arms 62, 64 have been secured to tissue. The one and only one incision is closed in a suitable manner desired by the physician and the patient begins recovery.

FIGS. 22A-22K are schematic views of embodiments of a process for implanting the tissue anchor system illustrated in FIG. 1 in a person to treat urinary incontinence.

In preparation for the surgery, the patient is reclined in a lithotomy position, the sterile field is defined with appropriate draping, and the skin of the patient is suitably prepped according to the guidelines of the healthcare facility. The packaging containing the tissue anchor system 20 is opened and the instructions for use are made available, for example on a back table in the surgical suite. The cannula 50 of the introducer 28 is sized to place each of the anchors 42 of the system 20 into tissue of the patient by accessing a single incision 145. The single incision 145 is the one and only one incision formed in the skin of the patient. One useful incision is a midline incision formed between the scrotum and the anus of a male patient to provide axis to the bulbar urethral complex. Some surgeons dissect the bulbous spongiosis muscle to access the urethra and the system 20 is appropriate for this approach. Other surgeons do not dissect the bulbous spongiosis muscle, but rather access the urethra complex and the system 20 is also appropriate for this approach. A dilator of some sort is typically used to force the incision 145 to an expanded position that provides access to the pelvic triangle. The dilator is not illustrated, but the incision is illustrated as an expanded circumferential area.

Figure 22A:
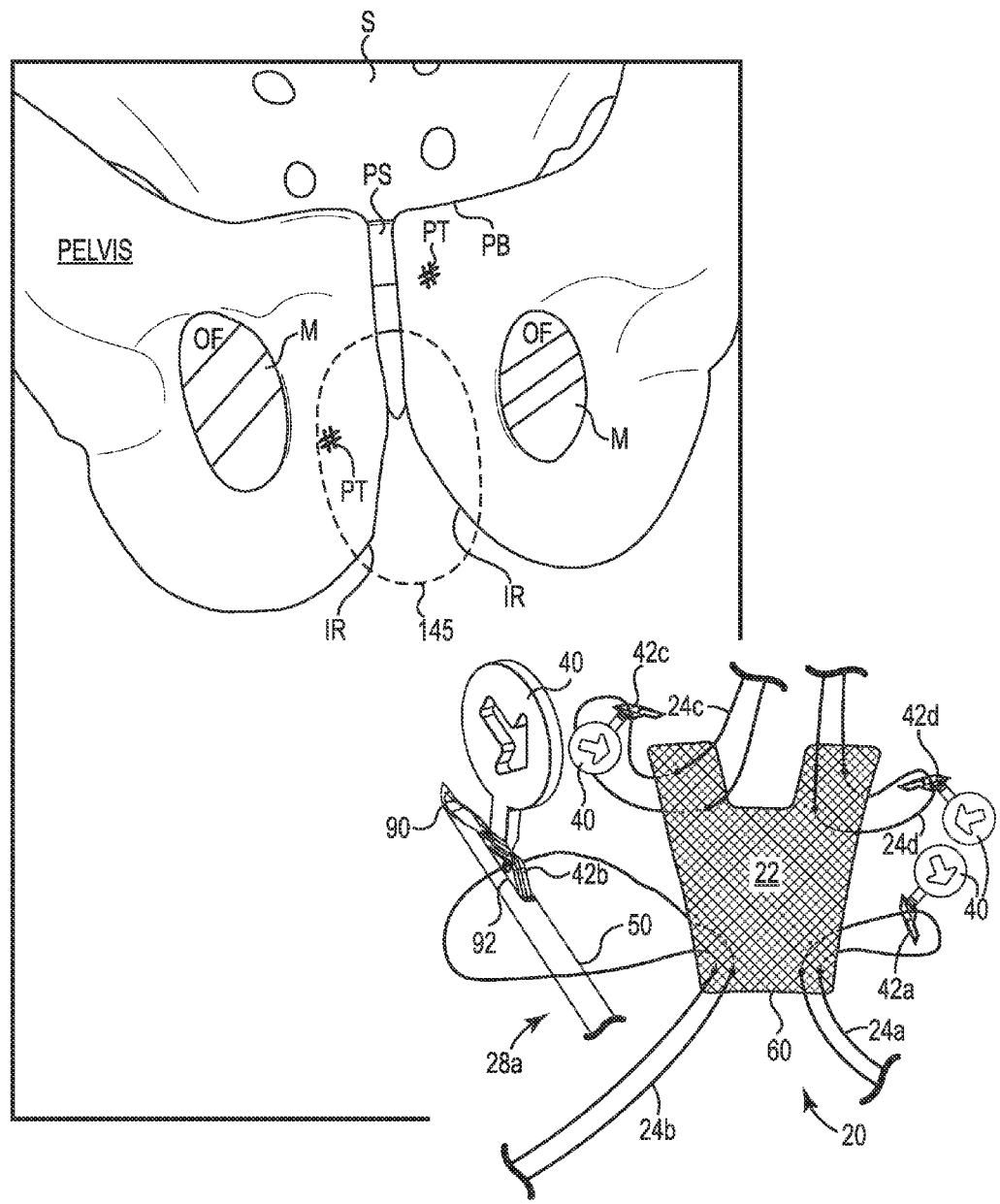
FIGS. 22A-22K are schematic views of embodiments of a process for implanting the tissue anchor system illustrated in FIG. 1 in a person to treat urinary incontinence.

FIG. 22A is a schematic view of the anchor 42b inserted into the slot 92 of the cannula 50. The anchors 42 are located between the support 22 and the patient, which allows the anchors to be fixated in tissue and the support to cover the bulbar urethral complex. The suture 24 is provided as a continuous loop of suture that extends through the eyelet of the anchor 42b, a portion of the base 60 of the support 22, and terminates in the break tab 30 (see FIG. 1). The conduit 29 of FIGS. 1-2 provided around a portion of the suture 24 to manage the suture array is optional.

The anchor 42b is somewhat small and can prove to be difficult to handle by a person wearing surgical gloves. The insertion tab 40 is provided to allow the anchor 42b to be inserted into the slot 92 of the cannula 50. The bore 90 and the slot 92 are sized to engage with and retain the anchor 42 in the cannula 50. The insertion tab 40 is subsequently removed from the anchor 42 and discarded, leaving the anchor 42 secured within the cannula 50.

The following procedure will place the anchors 42b, 42a associated with the base 60 of the support 22 in separate opposing obturator foramen (OF) of the patient. The anchor 42b is inserted in the patient's right side OF and the suture 24b is allowed to trail out of the incision 145. The anchor 42a is inserted in the patient's left side OF and the suture 24a is also allowed to trail out of the incision 145. The support 22 is position and the sutures 24b, 24a are tied off and terminated at the support 22. Thus, the base 60 of the support 22 is suspended by the sutures 24b, 24a implanted in the muscle of the OF. The anchors 42c, 42d attached to the pre-pubic arms of the support 22 are subsequently attached to tissue of the periosteum, and each suture 24c, 24d is secured after both anchors 42c, 42d are implanted, as described below.

Figure 22B:
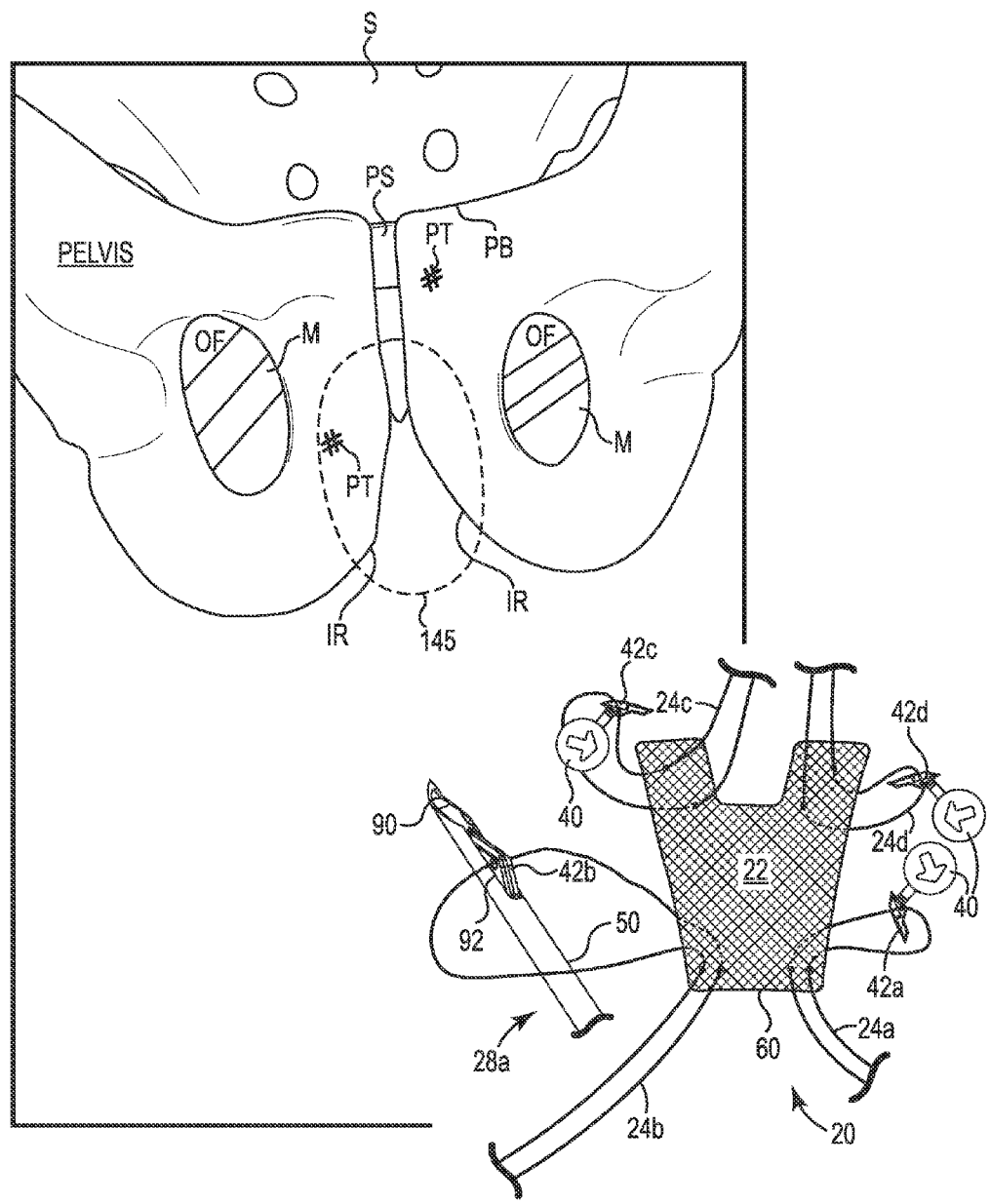

FIG. 22B is a schematic view of the anchor 42b inserted into the cannula 50. The insertion tab 40 has been discarded. In some instances, the anchor(s) are pre-loaded into a cannula and do not have a tab 40 that is discarded. Some embodiments of the cannula 50 include a distal end portion that is curved in the shape of a semicircle and suitably curved for passage around the descending ramus for insertion into the muscle of the obturator foramen OF.

Figure 22C:
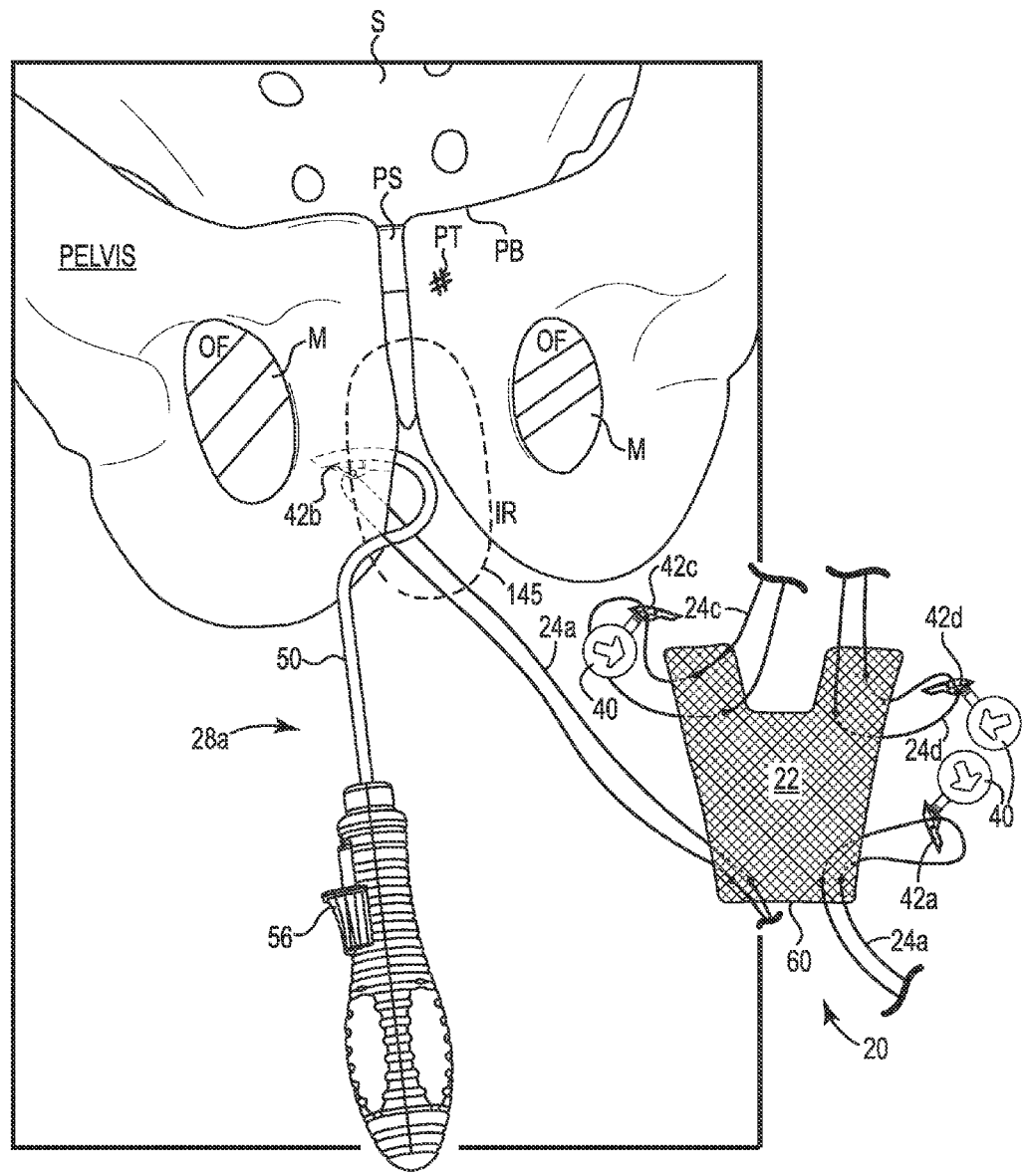

FIG. 22C is a schematic view of the right side introducer 28a (relative to the patient) inserted through the incision 145 and directed on a path around the descending ischial pubic ramus (or, ischial ramus IR). The end 80 of the cannula 50 follows a path from the incision 145, around the IR and penetrates the membrane M of the obturator foramen OF to a location of the obturator internus muscle. The button 56 is activated to push the anchor 42b out of the cannula 50 and into the obturator internus muscle. The introducer 28a is removed from the incision 145. The surgeon applies a force to the suture 24 to toggle the anchor 42b to ensure that the anchor is fully engaged with the obturator internus muscle. The base 60 of the support 22 is directed through the incision 145. The suture 24 is connected to the anchor 42b and passed through the support 22 and hangs freely out of the incision 145. The surgeon might choose to fixate the base 60 using the suture 24 and the anchor 42b, however experience has indicated that fixation of the base 60 is preferable after placing the second anchor 42a.

Figure 22D:
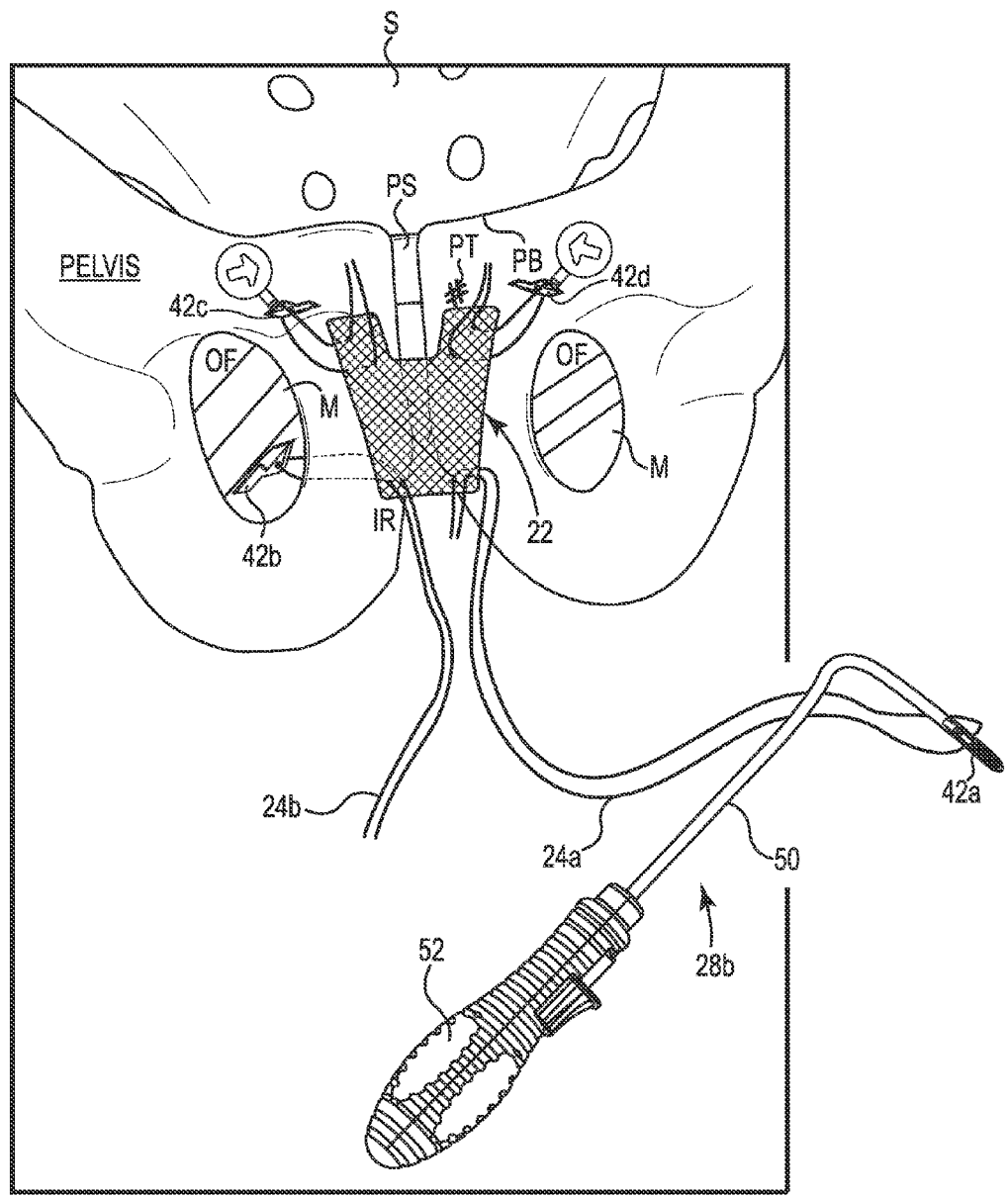

FIG. 22D is a schematic view illustrating the base 60 of the support 22 located in one desirable position with the second anchor 42a inserted into the cannula 50 of the left-hand introducer 28b. Anchor 42a will be inserted on the patient's left hand side using the introducer 28b that is provided with a curvature that is opposite from the curvature of introducer 28a (the right side introducer). Insertion tab 40 has been removed from the anchor 42a.

Figure 22E:
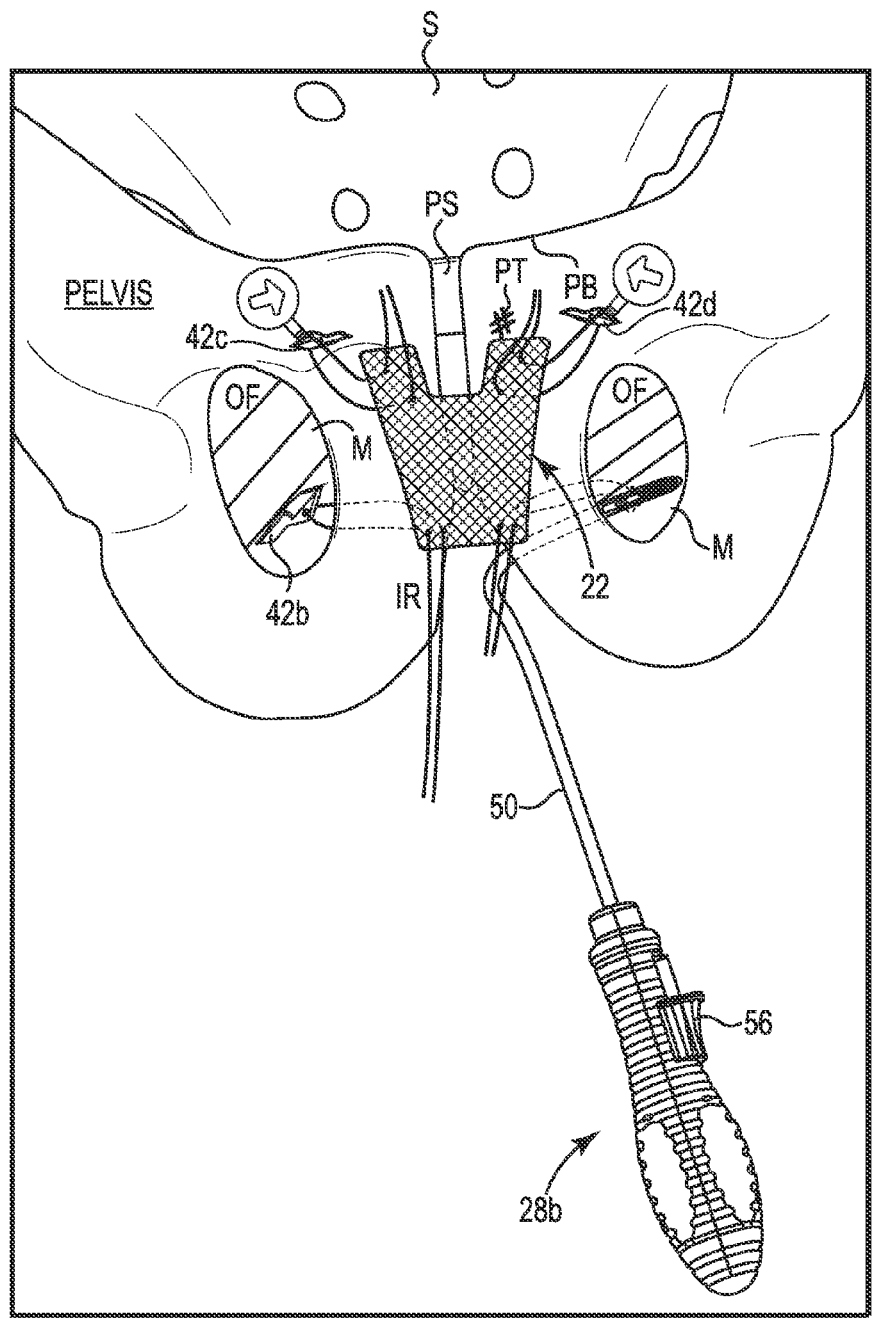

FIG. 22E is a schematic view of the left side introducer 28b inserted through the incision 145, around the descending IR, and through the membrane M covering the obturator foramen OF. The button 56 is moved to eject the anchor 42a out of the cannula 50 and into the obturator internus muscle. The introducer 28b is removed. The surgeon pulls on the suture 24 to toggle the anchor 42a in a sideway orientation within the muscle and to ensure that it is fully engaged with the obturator internus muscle. The suture 24 is allowed to descend through the support 22 and the incision 145 until fixated by the surgeon.

Regarding one process of anchoring the anchor to tissue, and as the steps are illustrated in FIG. 22E, the second anchor is inserted into a bore of a separate second cannula; the separate second cannula is inserted into the incision and along a second cannula path into tissue of an obturator foramen; the second anchor is ejected out of the bore of the separate second cannula and into the tissue of the obturator foramen; the second suture is pulled in a direction away from the patient to rotate the second anchor to position a length of the second anchor transverse to the second cannula path; and the second continuous suture loop is broken, allowing a second knot to be tied with the second suture to fixate the support in the patient.

Figure 22F:
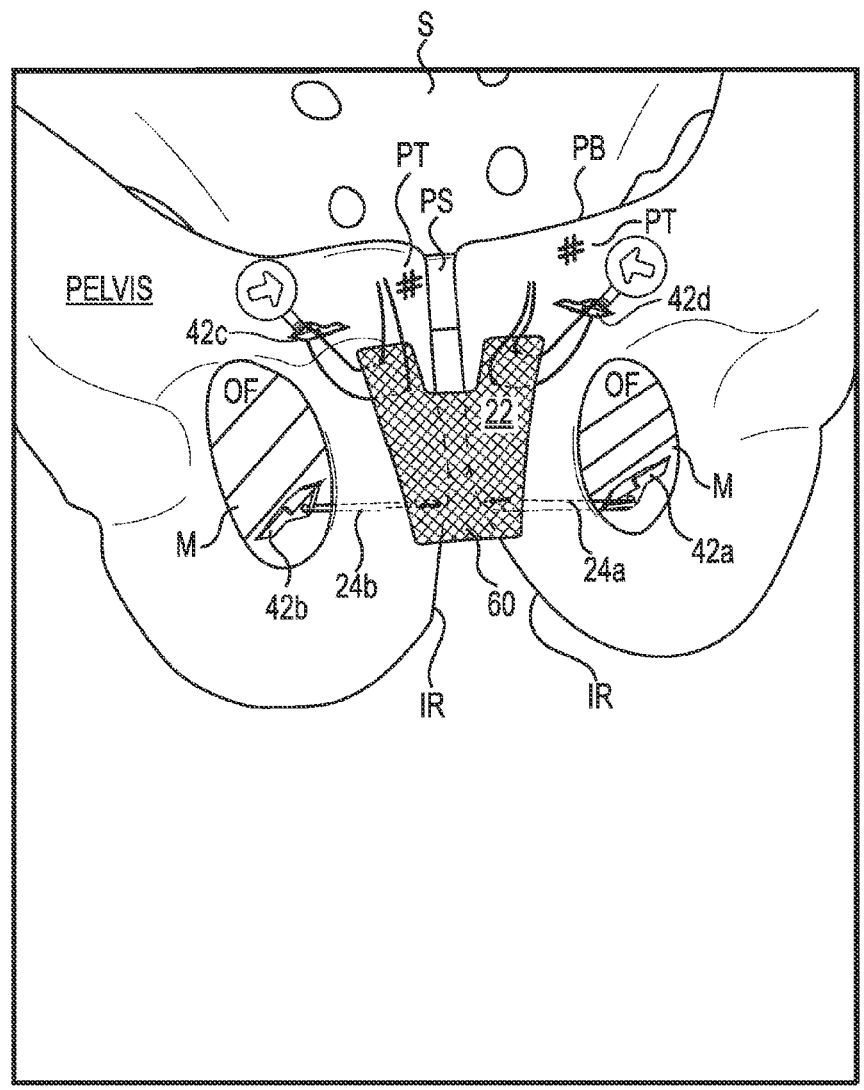

FIG. 22F is a schematic view of the support 22 guided through the incision with the base 60 maintained in a lateral orientation between the opposing obturator foramen OF. The surgeon locates a desired orientation for the base 60 and terminates the suture 24 connected to the anchor 42b and terminates the suture 24 connected to the anchor 42a. The surgeon applies an appropriate level of tension to the base 60 while terminating the sutures 24. In this way, the base 60 is suspended between the sutures 24 and a respective one of the anchors 42b, 42a. The pre-pubic arms 62, 64 are elevated to either side of the pubic symphysis PS.

Figure 22G:
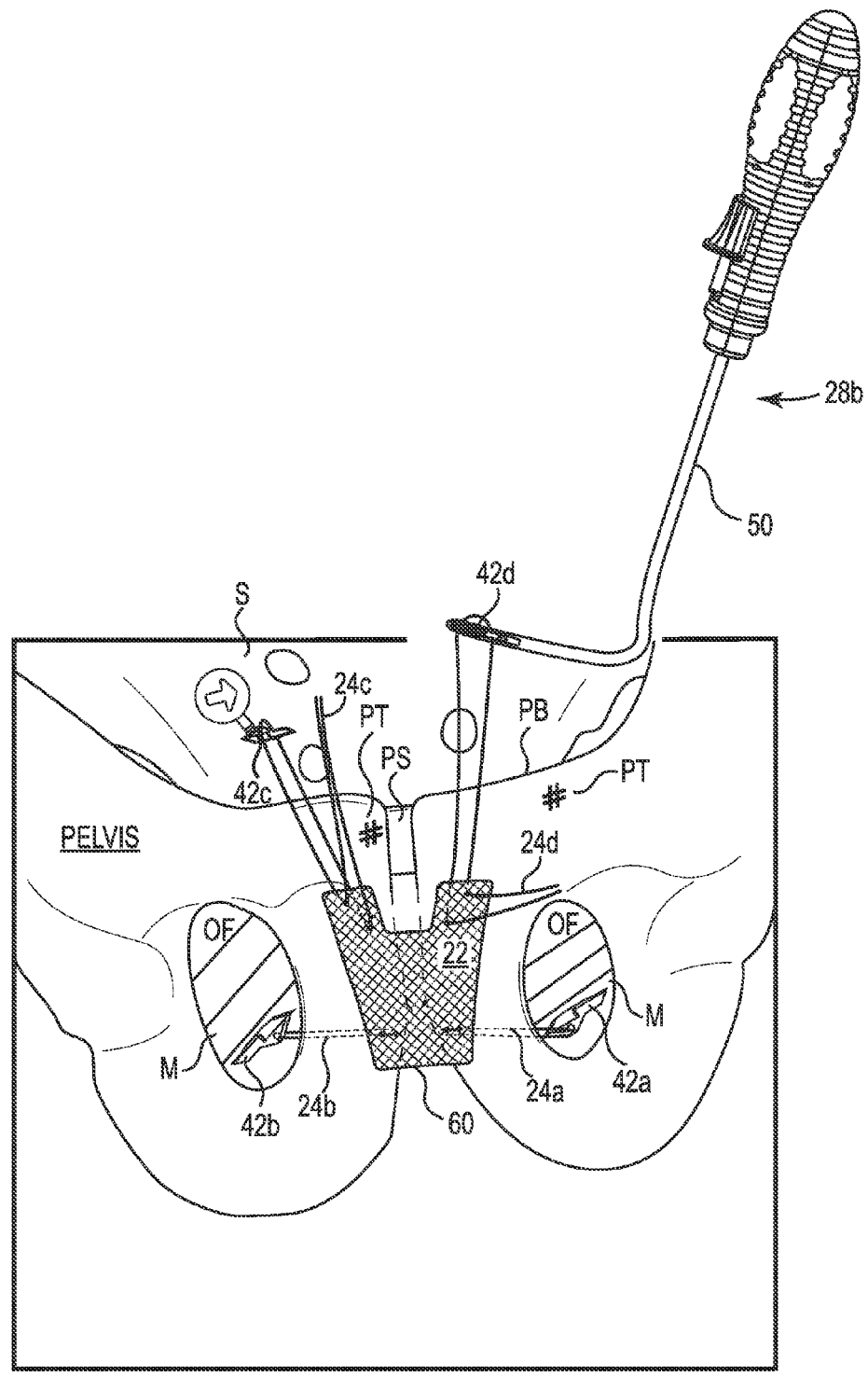

FIG. 22G is a schematic view of the anchor 42d loaded into the cannula 50 of the left side introducer 28b. The insertion tab 40 has been removed and discarded. The procedure allows for placement of the pre-pubic arm anchors 42c, 42d with either the right side introducer 28a or the left side introducer 28b, as determined by the preference of the surgeon. At times, the surgeon will simply maintain use of the most recently used introducer (in this case, introducer 28b from FIG. 22E); at other times, the most recently used introducer is returned to one of the surgical staff and the other introducer is employed.

Figure 22H:
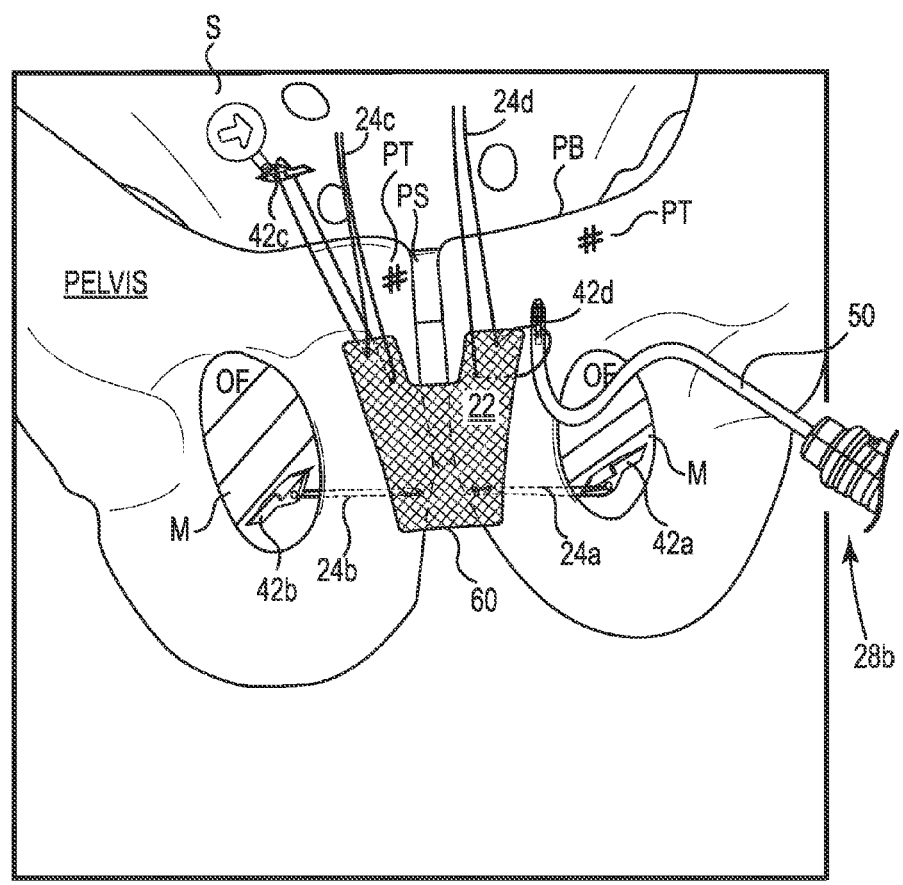

FIG. 22H is a schematic view of the introducer 28b inserted through the incision 145 to attach the pre-pubic arm 62 to the left-hand side of the patient. The end 80 of the cannula 50 is inserted through the periosteum tissue PT. The end 80 of the cannula 50 is bent/sloped or otherwise configured to allow the tip of the introducer to slide along the bone and avoid digging into the bone under the periosteum tissue PT. The button 56 is manipulated to eject the anchor 42d out of the cannula and under the periosteum tissue PT and on top of the bone. The introducer 28b is removed from the incision. The surgeon applies a pulling force to the suture 24 that is connected the anchor 42d, and this force toggles and rotates the anchor 42d into a broadside-on position that fully engages the anchor 42d with the periosteum tissue PT. the suture 24d extends from the implanted anchor 42d, through the pre-pubic arm of the support 22, and out of the incision for subsequent fixation.

Regarding one process of anchoring the anchor to tissue, and as the steps are illustrated in FIG. 22H, another anchor is inserted into the bore of the same cannula 28b that was employed in placing an anchor into the tissue of the obturator foramen, and this other anchor is inserted in the cannula and into the incision and along a second cannula path into periosteum tissue. This other anchor is ejected out of the bore of the cannula and into the periosteum tissue. The other suture attached to the other anchor is pulled in a direction away from the patient to rotate the other anchor to position a length of the anchor transverse to the second cannula path. The other continuous suture loop is broken to allow a knot to be tied to fixate the support over the periosteum tissue.

Figure 22I:
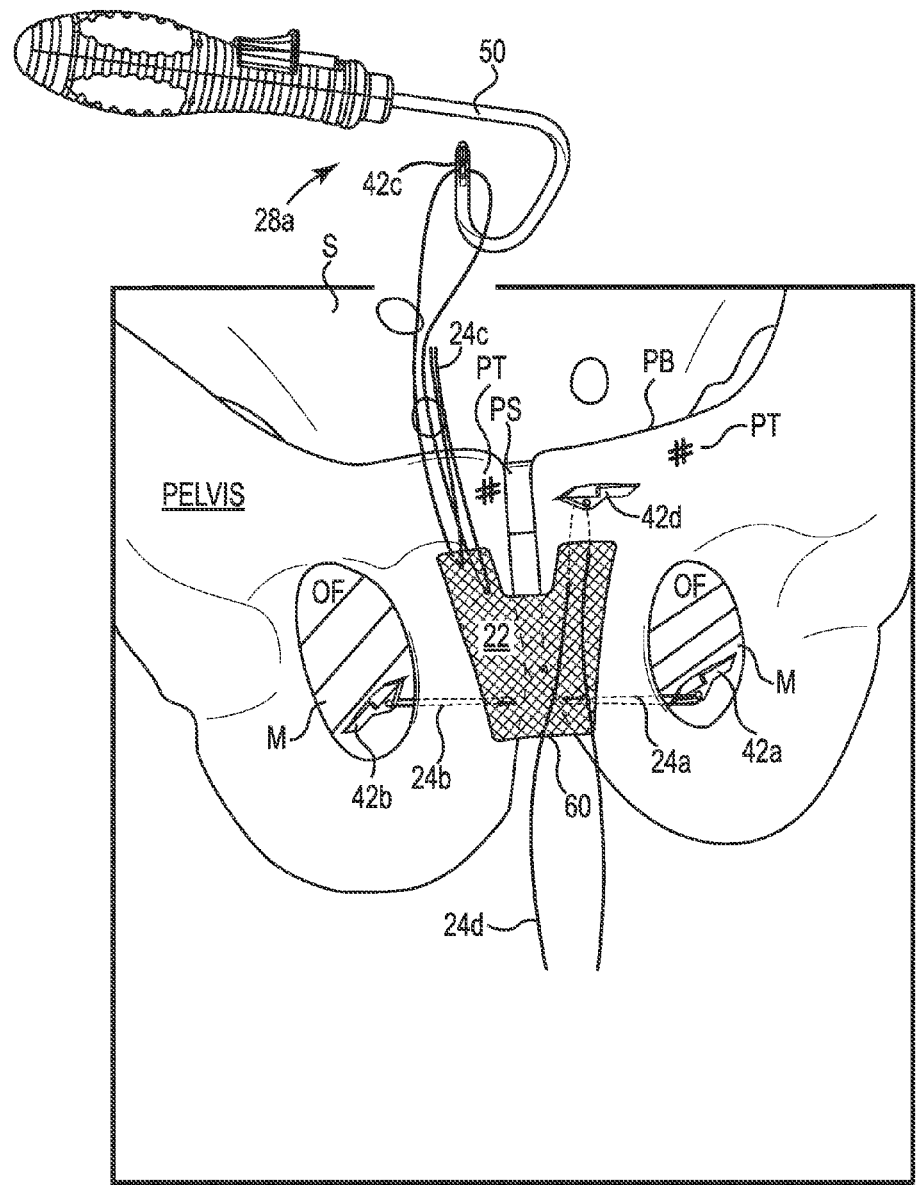

FIG. 22I is a schematic view of the base 60 of the support 22 suspended between the obturator foramen OF with the pre-pubic arm 62 secured to the periosteum tissue PT on the left-hand side of the patient by the anchor 42d. A fourth anchor 42c is inserted into the cannula 50 of, in this instance, the introducer 28a. Again, the insertion tab 40 has been removed from the anchor 42c and discarded.

Figure 22J:
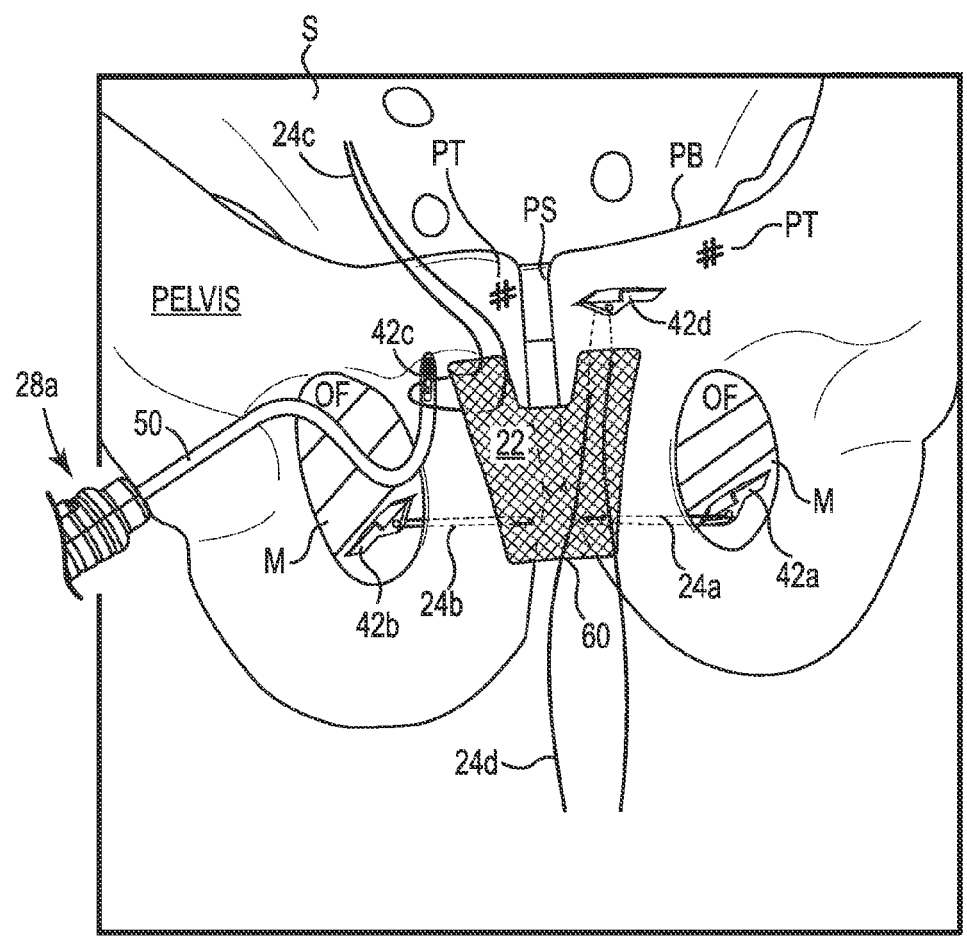

FIG. 22J is a schematic view of the introducer 28a inserted through the incision to fixate the pre-pubic arm 64 on the right-hand side of the patient. The end 80 of the cannula 50 is directed through the periosteum tissue PT. The end 80 of the cannula 50 will slide along the surface of the bone. When suitably placed between the periosteum tissue PT and the bone, the button 56 is pushed forward to eject the anchor 42c out of the cannula 50. The introducer 28b is removed from the incision. The surgeon applies a tension to the suture 24 to toggle, rotate, and engage the anchor 42c within the periosteum tissue PT. At this point in the process, two anchors 42d, 42c are attached in the two pre-pubic arms and the associated sutures 24d, 24c extend from the anchors 42d, 42c freely out of the incision 145.

The surgeon elevates both of the pre-pubic arms 62, 64 in tension against the fixed base 60 and terminates the sutures 24d, 24c.

Figure 22K:
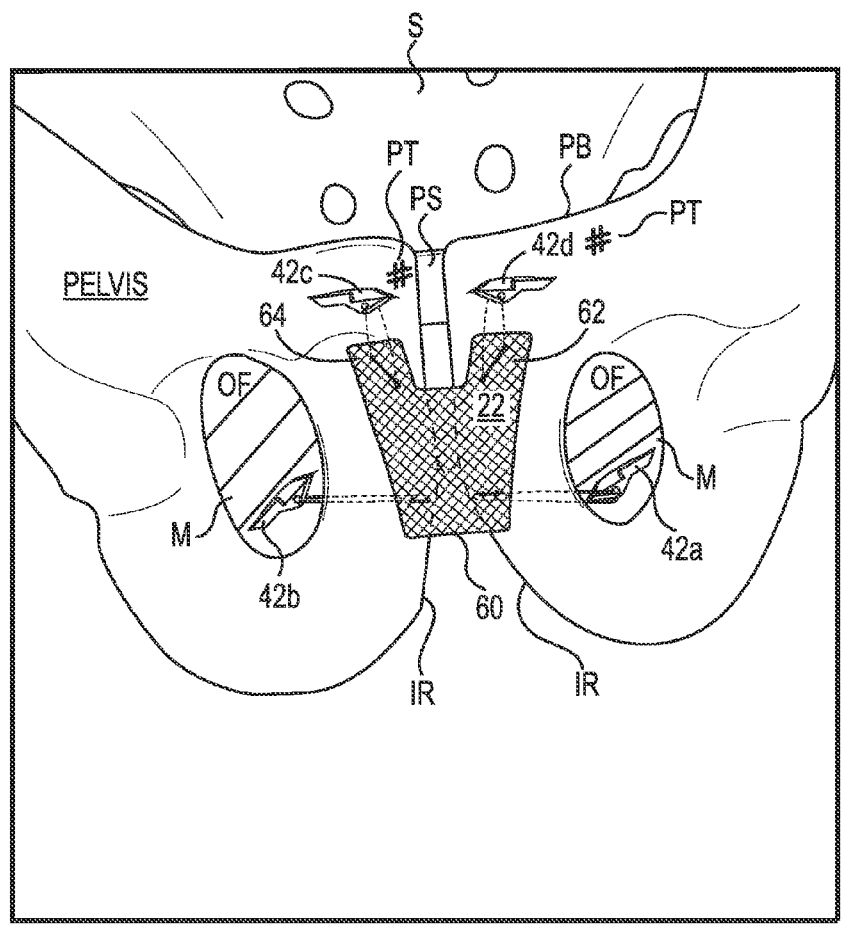
Figure 26:
FIGS. 26-38 are illustrations of embodiments of anchors suitable for use in the tissue anchor system.
Figure 27:
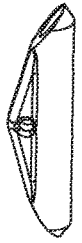
Figure 28:
Figure 29:
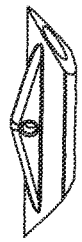
Figure 30:
Figure 31:
Figure 32:
Figure 33:

FIG. 22K is a schematic view of the support 22 suspended between the obturator foramen OF and the anchors 42a, 42b and fixated to the periosteum tissue PT by anchors 42c, 42d. The support 22 has been implanted through a single (one and only one) incision. The implanted anchors 42 combine with the sutures 24 to hold the support 22 in place and to elevate and compress the bulbar urethral complex in treating male urinary incontinence.

Some introducers and anchors suitable for use with the system 20 include an introducer provided with a needle, and an anchor having a recess that is sized to fit on and over the needle.

FIG. 23 is a side view of one embodiment of a system 400 including an introducer 402 provided with a needle 404 and an anchor 406 pinned onto and over the needle 404.

FIG. 24 is a side view of the needle 404 and the anchor 406 illustrated in FIG. 23. The needle 404 includes a pin 408 and the anchor 406 includes a recess 410 that is sized to receive the pin 408. A suitable suture is engaged with the anchor 406 and operates in a manner that is similar to the anchor 42 described above.

FIG. 25 is a side view of the anchor 406 engaged with the pin 408 of the needle 404.

The anchors described above include some aspect of an asymmetric geometry and some aspect of an asymmetric distribution of mass along a length of the anchor. It has been discovered that other anchors shapes and sizes are also suitable.

FIG. 26-FIG. 33 illustrate anchors provided with symmetry relative to a vertical line drawn through a midpoint of the length of the anchor. These anchors have an asymmetric mass distribution relative to a longitudinal axis of the anchor. For example, the anchors illustrated in FIG. 26-FIG. 33 are symmetric relative left and right to the eyelet provided for engagement with the suture. The anchors illustrated in FIG. 26-FIG. 33 are pre-formed to include a recess sized for placement over a pin or needle of an introducer. These laterally symmetric anchors could also be configured for placement into a cannula, similar to the cannula 50 described above.

Figure 34:
Figure 35:
Figure 36:

FIG. 34-FIG. 36 illustrate anchors having a geometric asymmetry and an asymmetric distribution of mass relative to the eyelet. The anchor illustrated in FIG. 34 has a single tissue engagement fin, and the anchor illustrated in FIG. 35 has multiple tissue engagement fins. FIG. 36 illustrates an anchor having an eyelet and no fin.

Figure 37:
Figure 38:

FIG. 37-FIG. 38 illustrate solid anchors having a geometric symmetry relative left and right to the eyelet and more mass on the longitudinal side of the eyelet than on the side of the anchor opposite of the eyelet.

Figure 39:
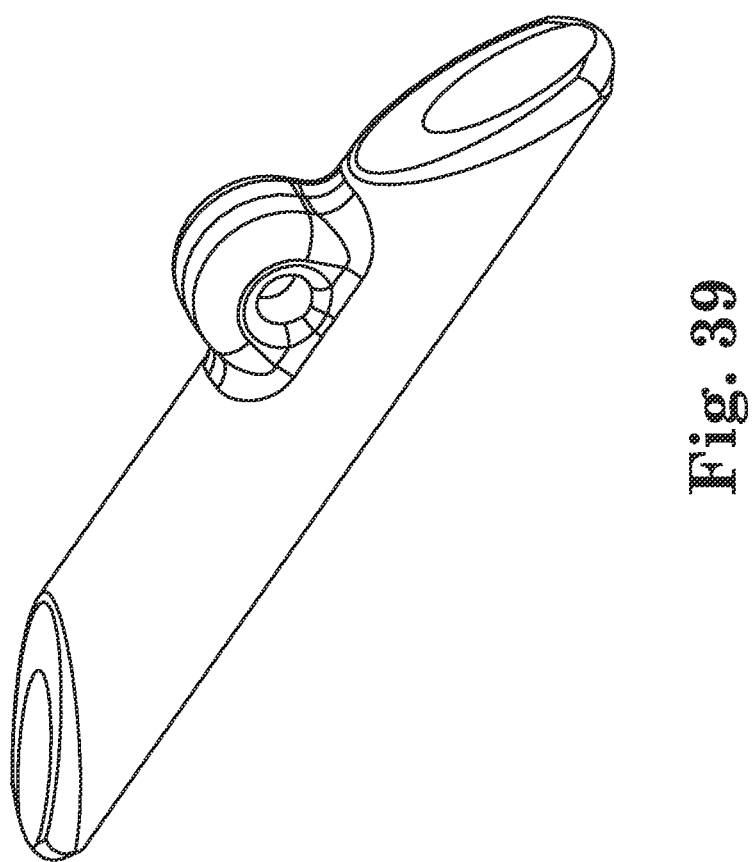
FIGS. 39-46 are views of embodiments of anchors suitable for use in the tissue anchor system.

FIG. 39 is a perspective view of one embodiment of an anchor suitable for use with the system 20 described above.

Figure 40:
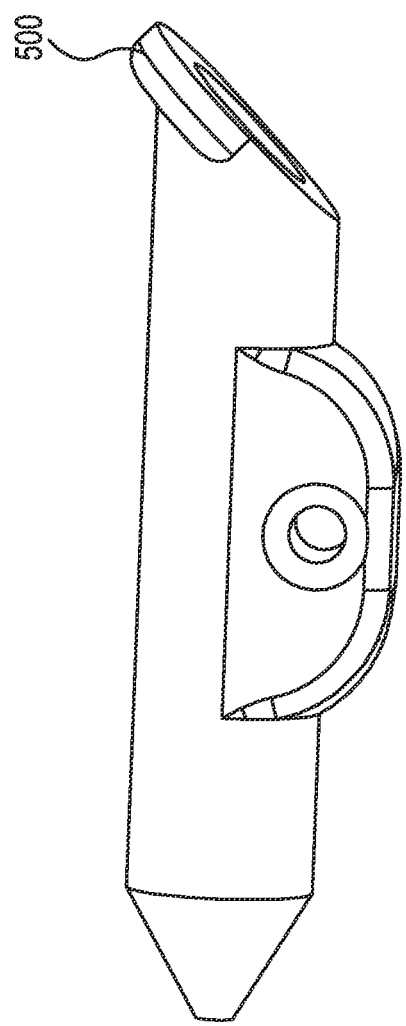

FIG. 40 is a perspective view of one embodiment of an anchor suitable for use with the system 20 described above. The anchor illustrated in FIG. 40 includes a flange 500 that is configured to drag as the anchor is pulled through tissue, which encourages rotation and engagement of the anchor in the tissue.

Figure 41:
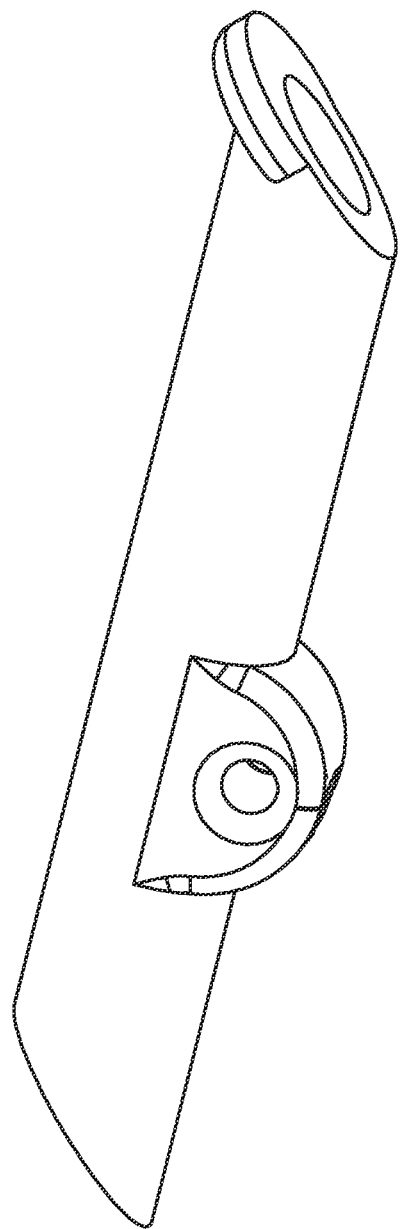

FIG. 41 is a perspective view of one embodiment of an anchor suitable for use with the system 20 described above.

Figure 42:
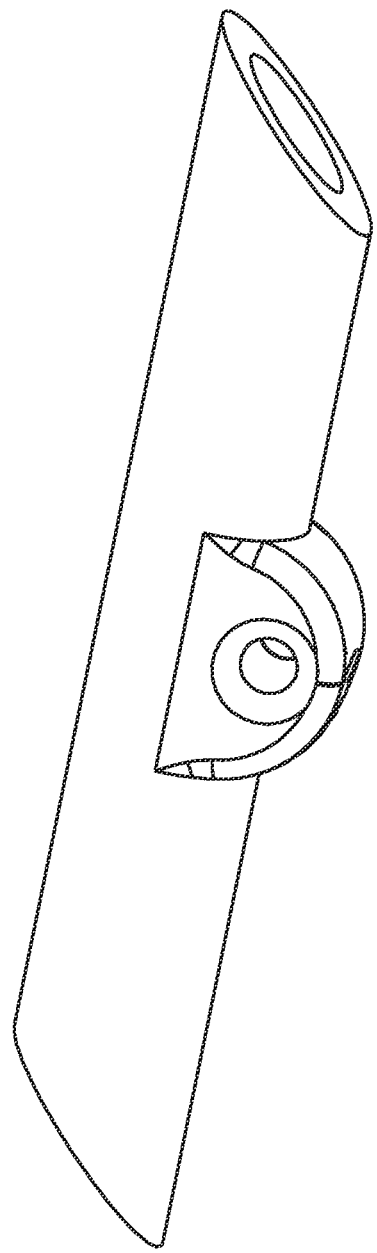

FIG. 42 is a perspective view of one embodiment of an anchor suitable for use with the system 20 described above.

Figure 43:
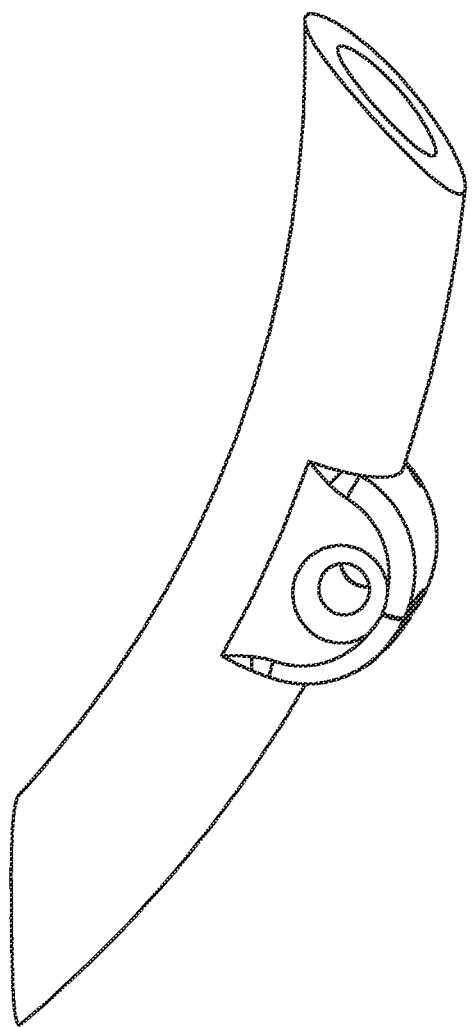

FIG. 43 is a perspective view of one embodiment of an anchor suitable for use with the system 20 described above. The anchor illustrated in FIG. 43 is has an arcuate body provided with a curvature.

Figure 44:
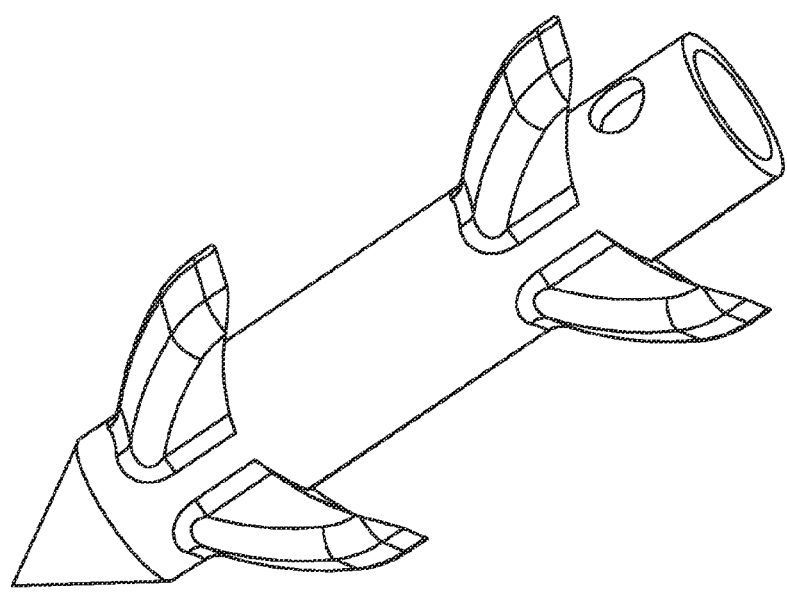
Figure 45:
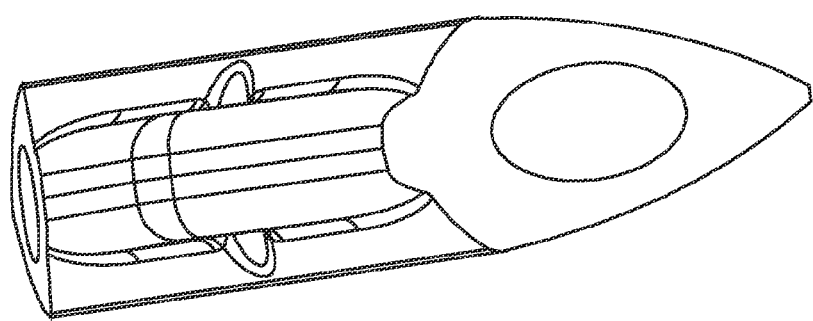
Figure 46:
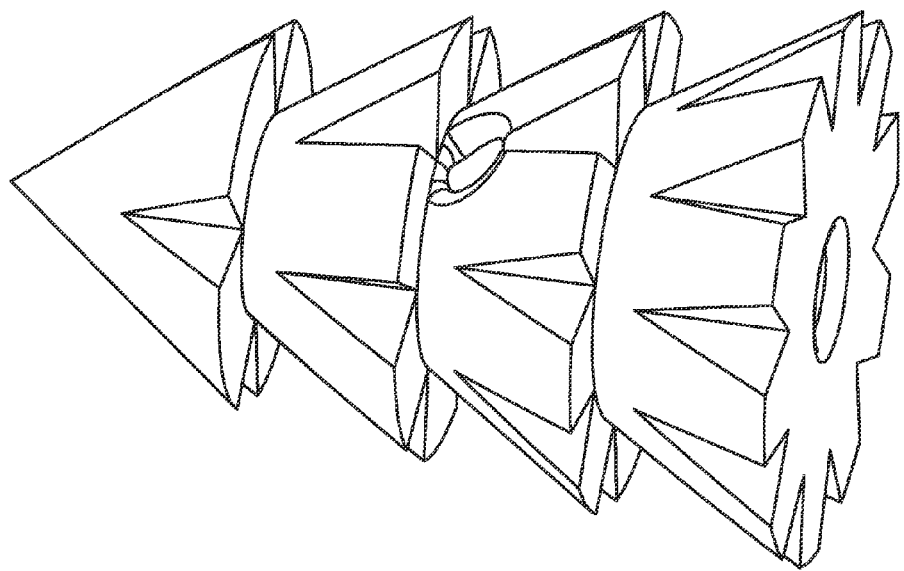

FIG. 44-FIG. 46 are perspective views of anchors suitable for use with the system 20 described above. Each of the anchors illustrated in FIG. 44-FIG. 46 include multiple tissue engagement flanges. The anchor illustrated in FIG. 44 is bullet-shaped for ease of insertion into tissue and has multiple flaps that are configured to provide excellent engagement with tissue.

A variety of suitable suture management devices are described, including the break pad 30 illustrated in FIG. 1, in addition to buttons, sliding knots, fixed knots, destructive bonds, smash bonds, and other suture management devices.

Figure 47:
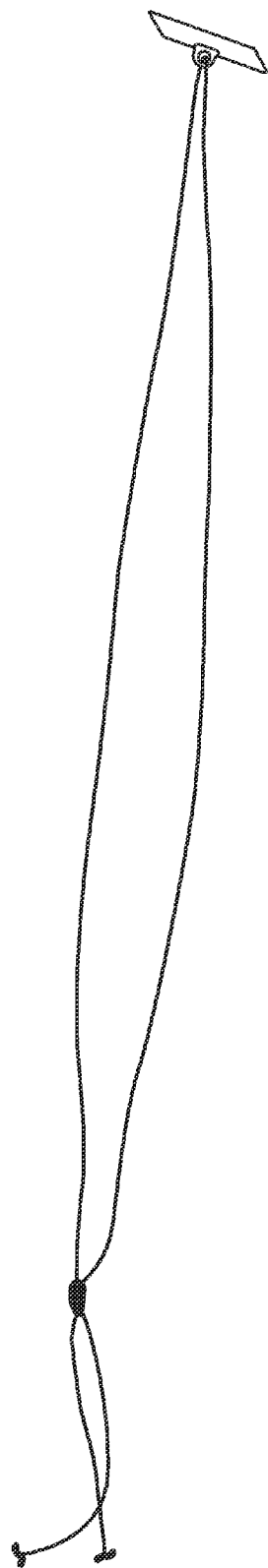
FIG. 47 is a perspective view of one embodiment of an anchor assembly.

FIG. 47 illustrates a suture engaged with an anchor, with a suture management device engage between a top segment and a bottom segment of the suture.

Figure 48:
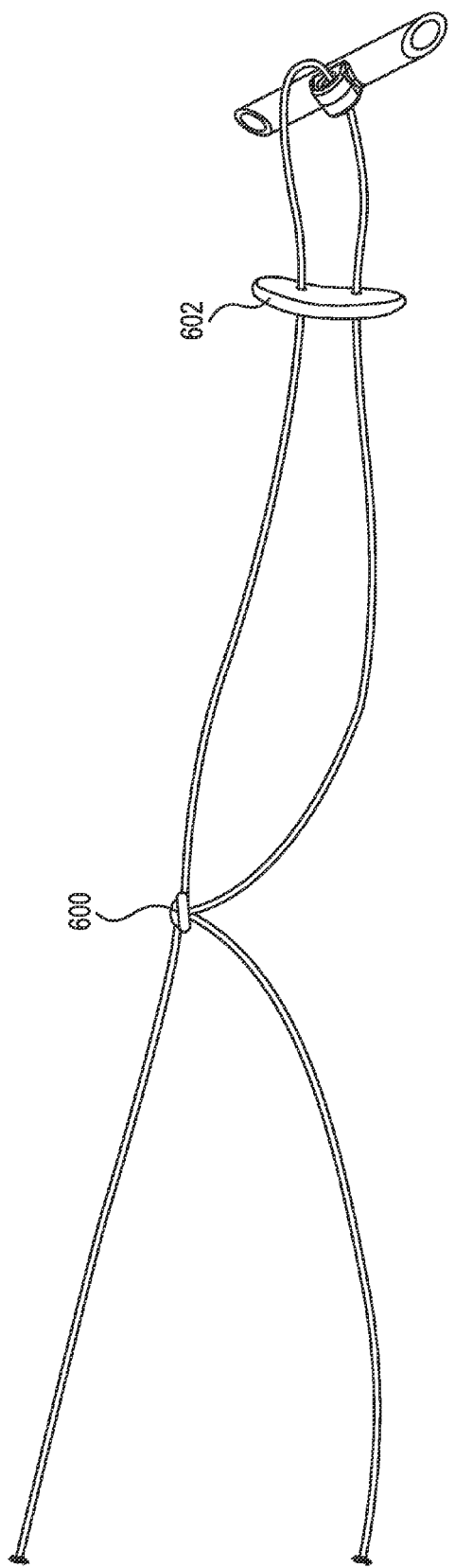
FIG. 48 is a perspective view of one embodiment of an anchor assembly including a stop knot engagement feature.

FIG. 48 is a perspective view of a suture engaged through an eyelet of an anchor, with the suture provided with a sliding knot 600 and a sliding fixation mechanism 602. After placement of the anchor, the sliding fixation mechanism 602 is slid along the suture to hold a support material in place. The sliding knot 600 is slid down the suture into engagement with the fixation mechanism 602, which prevents the sliding fixation mechanism 602 from becoming loose.

Other Approaches Employing Anchor Assembly 26

The following disclosure describes other approaches in which the system 20 described above could be used in treating urinary incontinence. The following disclosure cooperates with and complements the disclosure above and forms a part of this specification.

The following disclosure illustrates a different set of FIG. 49-FIG. 77 describing an introducer for delivering an anchor 42 attached to a suture 24. All of the following procedures described in the following FIG. 49-FIG. 77 can be suitably achieved by employing the anchor assembly 26 and the introducer 28 as described above. The shape of the support material is suitably selected from the support material 22 described above in FIG. 1, or with the support materials described below in FIG. 53-FIG. 54, FIG. 60-FIG. 65, FIG. 666-FIG. 71B, FIG. 76, or FIG. 77.

Figure 49:
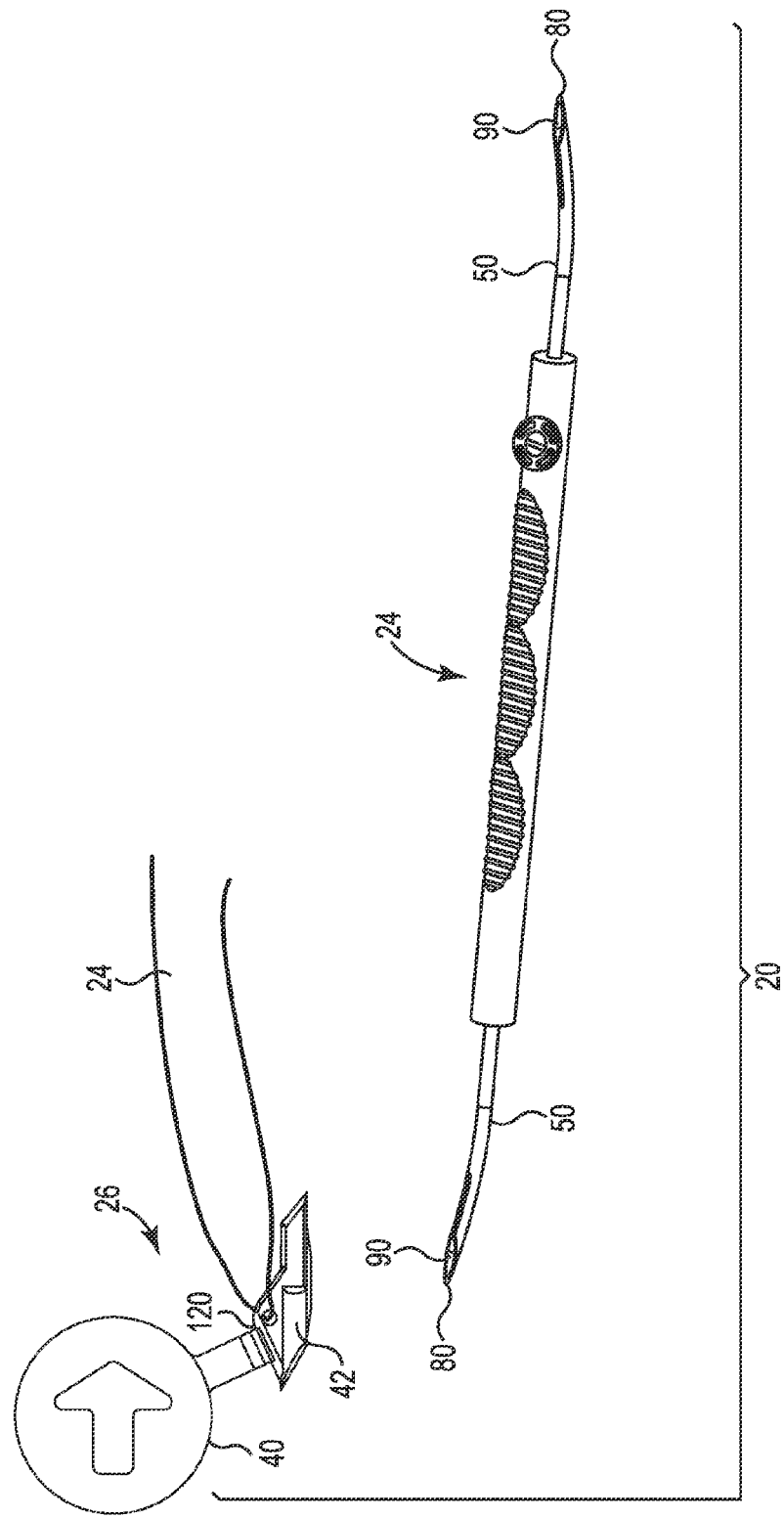
FIG. 49 is a perspective view of one embodiment of a surgical system including anchors insertable into a dual cannula introducer.

FIG. 49 is a perspective view of one embodiment of a surgical system 20 including a dual-ended introducer, with each end having one of the cannulas 50 described above that is sized for use with the anchor 42.

The introducer includes two cannulas 50 extending from a handle. The handle includes a gripping surface formed on at least one side of the handle. It is acceptable to provide the handle with several gripping surfaces or with no gripping surfaces. During a suturing procedure, the anchor 42 is loaded into the opening of the cannula 50 and the surgeon grips the handle and directs the pointed distal end of the cannula 50 to a targeted tissue landmark. Force delivered to the handle in a distal direction will drive the pointed distal end of the cannula 50 into the tissue, such that a subsequent withdrawal of the introducer in a proximal direction will allow the introducer to exit the tissue. The anchor 42 is engaged with and deposited in the tissue after the cannula 50 is withdrawn.

In one embodiment, the introducer includes a pair of cannulas, including a second cannula 50 having the same pointed distal end and an opening formed in the cannula 50. The second cannula 50 is provided to receive a second, separate anchor 42.

Suitable materials for fabricating the anchor 42 include plastics, or metal, or sintered material. One suitable material for fabricating the anchor 42 is polypropylene. Another suitable material for fabricating the anchor 42 is a bioabsorbable polymer that configures the anchor 42 to be absorbed into the body over a period of several weeks.

Suitable materials for fabricating the length of suture 24 include bio-inert components that do not bioabsorb, or bioabsorbable components that are configured to be absorbed or resorbed by the body. One suitable material for fabricating the length of suture 24 is polypropylene. Other suitable materials for fabricating the length of suture 24 include dissolvable sutures available from Ethicon™, a J&J Company located in Somerville, N.J., and include Monocryl™ (polyglycaprone 25) sutures, coated Vicryl™ (polyglactin 910) sutures, Ethicon Plus™ Sutures, or polydioxanone sutures as examples.

Suitable materials for fabricating the cannula 50 and include plastics or metal. One suitable material for fabricating the cannula 50 is stainless steel. Other suitable materials are acceptable.

The anchor 42 is useful for fixating a support material within a patient's body. The introducer is sized to place the anchors 42 through a single incision and into the periosteum tissue that covers the pubic bone, examples of which are described below.

Figure 50:
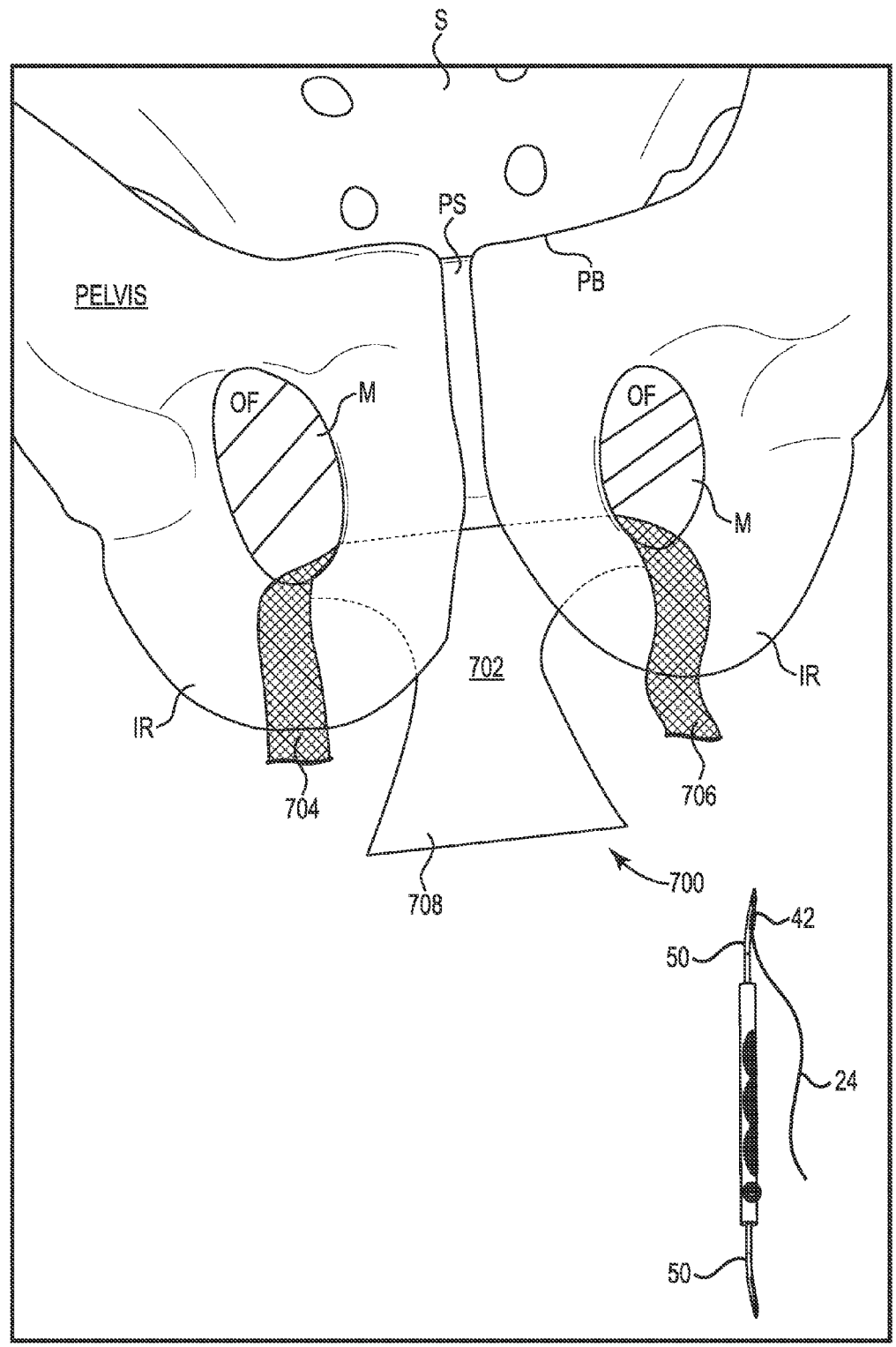
FIG. 50 is a schematic view of one embodiment of the surgical system provided to anchor a support material to tissue of the human body, with the support material having an arm inserted through each of two obturator foramen of the pelvis.

FIG. 50 is a schematic view of one embodiment of a support 700 attachable to a pelvis of a patient. FIG. 50 provides an anterior view of the pelvis with the sacrum S located in a posterior portion of the view, with the pubic symphysis PS centered relative to the pubic bone PB, and an obturator foramen OF on each bilateral side of the pelvis. Each obturator foramen OF provides an opening or a window that is covered by a membrane M. Nerves and arteries traverse the upper reaches of the obturator foramen OF. The membrane M generally includes several layers of muscle and at least one layer of ligament-like tissue that connects the muscles in the membrane M to the pelvis. The ischial pubic ramus IR is located inferior to the pubic bone PB and the obturator foramen OF.

The support 700 is provided to elevate and compress the male urethra and includes a body 702, a first arm 704 extending from the body 702, a second arm 706 extending from the body 702, and a pre-pubic portion 708 that is oriented in a generally orthogonal position relative to the arms 704, 706. The illustrated embodiment is a two-arm device.

Suitable materials for fabricating the support 700 include porous materials that allow tissue ingrowth throughout the support structure to anchor the support 700 in the body after implantation and healing. Suitable such porous materials include autograft material (the patient's own tissue), allograft material (tissue from a cadaver), xenograft material (tissue from another species), or synthetic materials such as woven fabrics, knitted fabrics, meshes, nonwoven fabrics, meshes, fibrillated fibers, or spun and fibrillated fibers that are provided with voids (pores) configured to allow tissue ingrowth into the support 700. The pores are generally larger, on average, than 75 µm.

The support 700 is attached to the pelvis with each arm 704, 706 inserted into one of the respective obturator foramen OF, and with the pre-pubic portion 708 attached to the periosteum tissue that lines the exterior of the pubic bone PB. The following surgical procedure is one example of the suitable implantation of the support 700 into a male patient.

The patient is positioned on a surgical operating table in a lithotomy, or modified lithotomy position, and is anesthetized. A vertical midline perineal incision is formed between the scrotum and the anus. Tissue is dissected to expose the bulbous muscle around the urethra. A suitable tool is used to direct the arm 704 into and through the first obturator foramen OF, and this procedure is repeated on the contralateral side to place the arm 706 into and through the second obturator foramen OF.

One suitable approach of placing the arms 704, 706 through the obturator foramen OF is described as an "outside-in" approach. The outside-in approach includes directing a needle or other device through the skin of the groin area of the patient external of the obturator foramen OF along a curved path through the membrane M and around the ischial pubic ramus R such that the tool exits the midline perineal incision. One of the arms 704, 706 is attached to the tool, and the tool is withdrawn along its curved pathway back around the ischial pubic ramus IR, through the membrane M, out of the obturator foramen OF, and out of the skin at the groin area. In this manner, each arm 704, 706 is directed through and placed in one of the obturator foramen OF. The arms 704, 706 are trimmed to a subcutaneous level. A holding stitch is placed to hold the arm 704, 706 relative to the groin tissue, as determined by the surgeon.

A different approach is the "inside-out" approach in which the needle or tool is coupled to the support and directed from the perineal incision (inside) outward to the skin at the groin area (outside). Placement of the arms 704, 706 with the inside-out approach is also acceptable.

One acceptable single incision approach includes the formation of a single (exactly one) incision in the urogenital triangle. Tissue is dissected distal the incision to access the urethra and the pelvis. The arms 704, 706 of the support 700 are directed into the single incision and anchored to the membrane M of the obturator foramen OF, for example with the anchor 42 as described above in FIGS. 22A-22K. The pre-pubic portion 708 is inserted into the single incision and fixed to the periosteum tissue over the pubic bone PB by the anchor 42 as delivered by the introducer. In this manner, a treatment for urinary incontinence is provided to the patient by forming exactly and only one incision and implanting the support 700 through that single incision.

Figure 51:
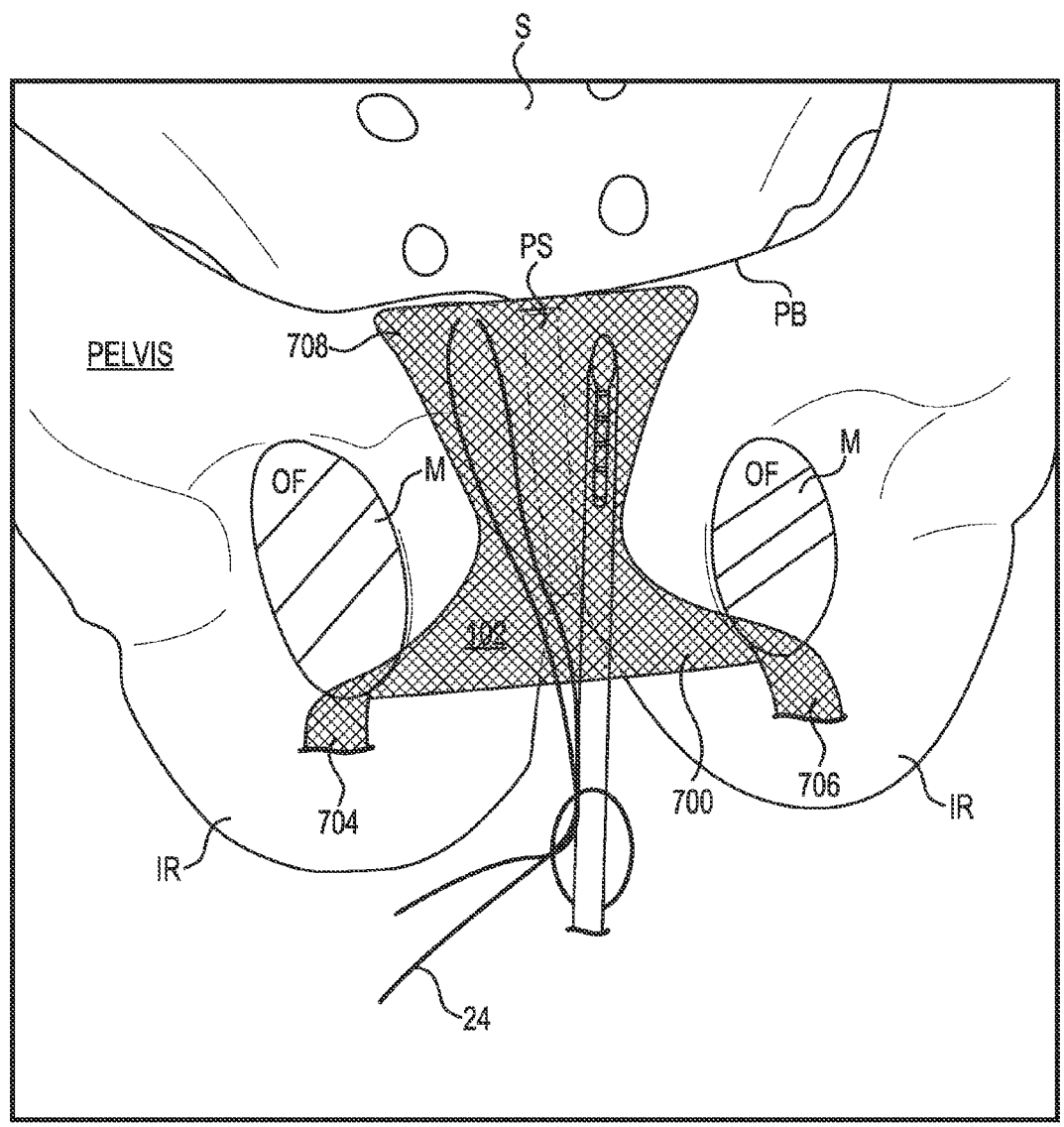
FIG. 51 is a schematic view of one embodiment of the surgical system employed to anchor a support material to the tissue of the human body showing a pre-pubic portion being attached to the periosteum of the pubic bone.

FIG. 51 is a schematic view of the surgical system employed to fixate the pre-pubic portion 708 of the support 700 to the periosteum tissue of the pubic bone PB. The cannula 50 of the introducer is inserted into the perineal incision and directed to the pubic bone PB anterior to the pelvis.

In one suitable approach, the anchor 42 is driven through the material of the support 700 and into the periosteum tissue that covers the pubic bone PB. The cannula 50 pierces the periosteum tissue and slides along the bone of the pelvis without entering or penetrating the bone. The anchor 42 is engaged under the periosteum tissue and the suture 24 extends through the support 700 out through the perineal incision. The surgeon, depending upon surgeon preference, will place at least one anchor 42 through the pre-pubic portion 708 an each side of the pubic symphysis PS. The suture 24 extends from each anchor out through the perineal incision and is available for subsequent tying or other termination.

In a different suitable approach, the anchor 42 is loaded into the introducer and the cannula 50 is introduced in the perineal incision up to the pubic bone PB anterior to the pelvis. The introducer is employed to drive the anchor 42 under the periosteum tissue of the pubic bone PB and the cannula 50 is withdrawn through the perineal incision. The suture 24 trails behind the anchor 42 and exits the body at the incision. An end of the suture 24 is inserted through the pre-pubic portion 708 of the support 700, and the pre-pubic portion 708 is guided along the suture 24, through the incision, and up to the pubic bone PB. Thereafter, the suture 24 is tied or terminated to hold the pre-pubic portion 708 against the pubic bone.

Figure 52:
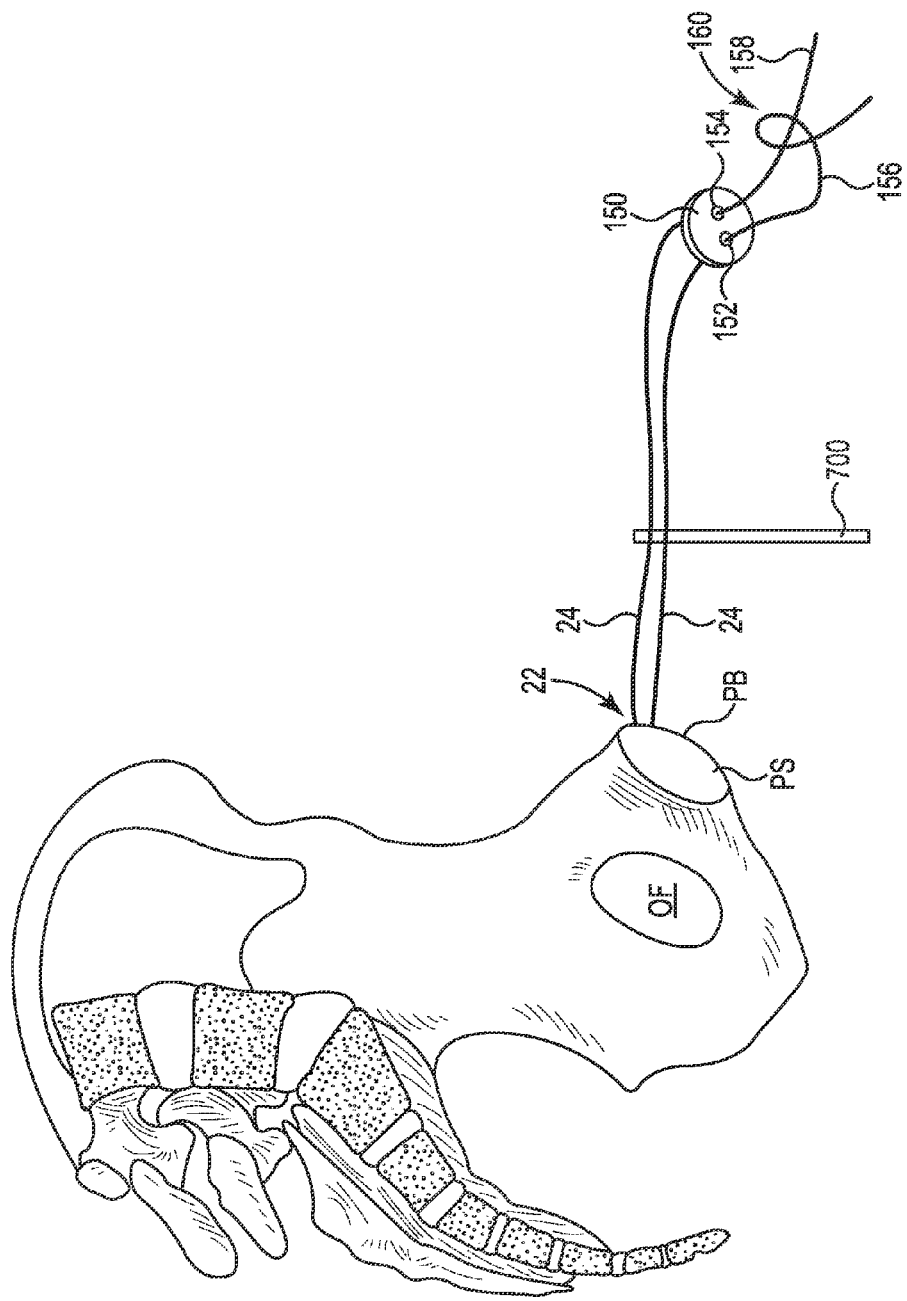
FIG. 52 is a schematic view of the anchor secured to tissue and including a stopper coupled with a suture and located between the anchor and a slip knot.
Figure 53:
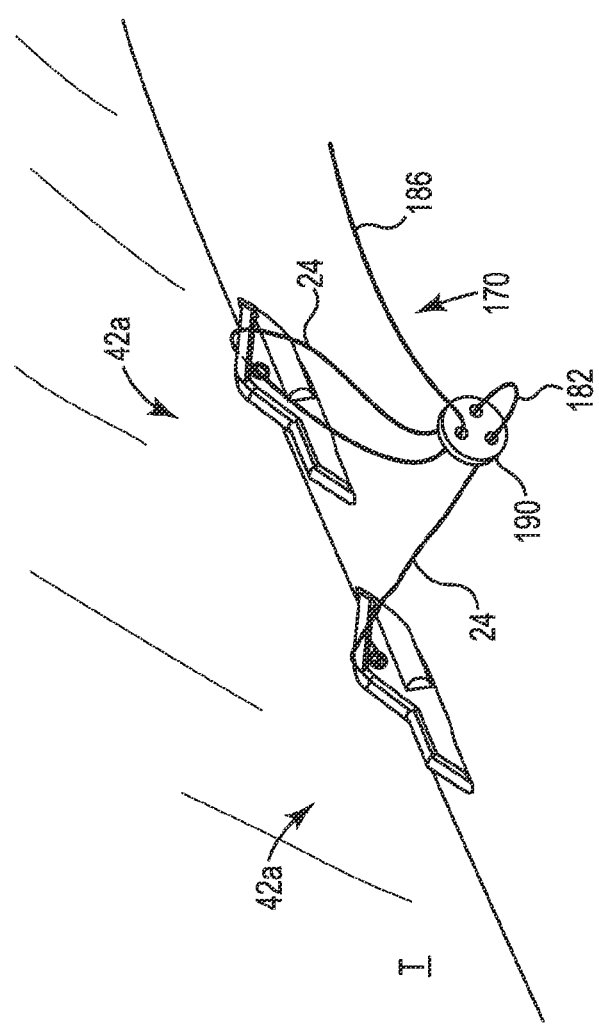
FIG. 53 is a schematic view of two anchors secured to tissue and coupled with a suture.

FIG. 52 is a schematic view of the anchor 42 secured to the periosteum tissue and the support 700 secured to the suture 24. In one embodiment, the system 20 described above includes a stopper 150 that is attached to the suture 24, where the stopper 150 is configured to slide along the suture 24 and direct the support 700 into the patient's body and against the tissue. In one embodiment, the stopper 150 has a first orifice 152 and a second orifice 154. One or more of the anchors 42 is engaged with the periosteum tissue of the pubic bone PB, and a first end 156 of the suture 24 extends from the anchor 42 through the first orifice 152, and a second end 158 of the suture 24 extends to the second orifice 154. The stopper 150 slides along the suture 24 and is operable to push or otherwise deliver the support 700 against the pubic bone PB. In one embodiment, a slip knot 160 or other termination device is provided to tie the suture 24 against the stopper 150 after the stopper 150 and the support 700 has been delivered to the pubic bone PB. The stopper 150 is located between the anchor 42 and the slip knot 160.

Suitable materials for fabricating the stopper 150 include plastics or metal. One suitable material for fabricating the stopper 150 includes polypropylene. Another suitable material for fabricating the stopper 150 includes stainless steel. In one embodiment, the stopper 150 is fabricated to be bioabsorbable.

Figure 55:
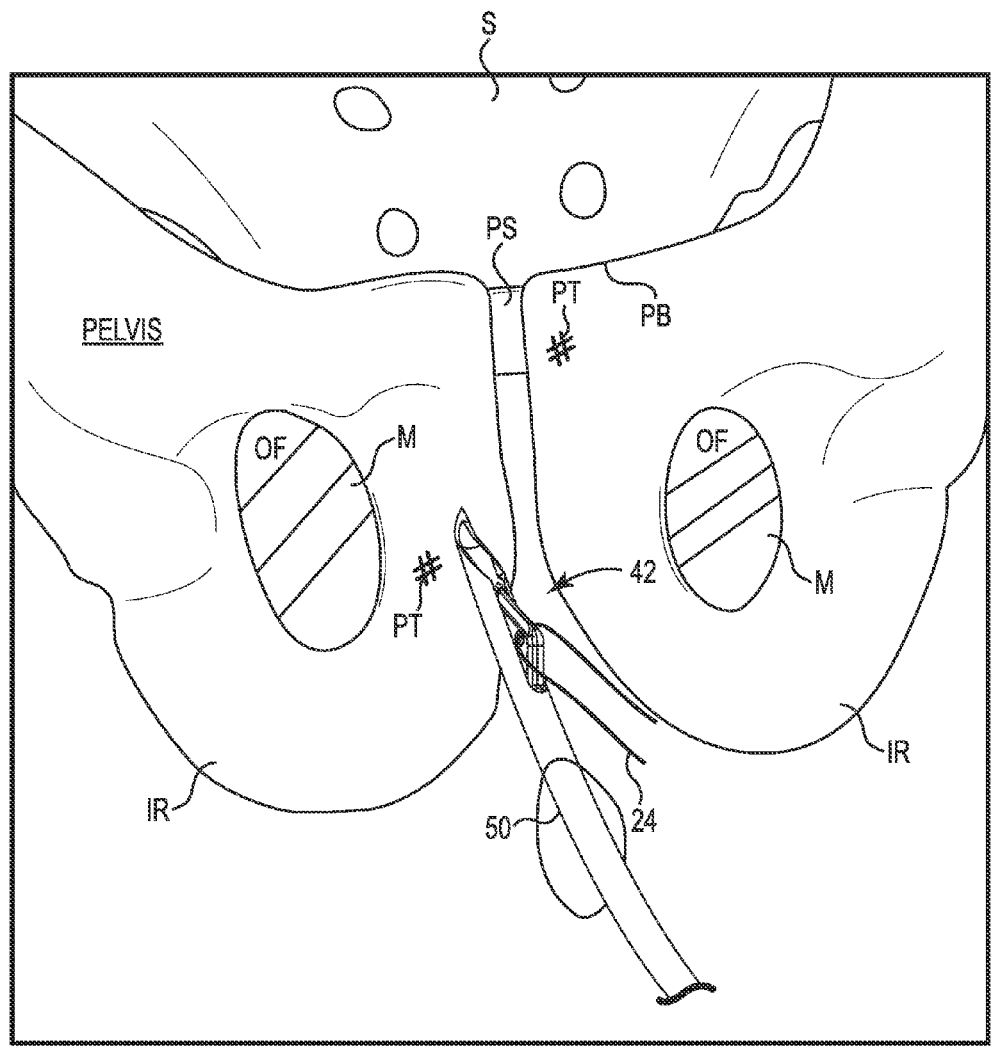

FIG. 55 is a schematic view of two anchors 42 secured to tissue T and coupled with a suture 170. The anchors include a first anchor 42a and a second anchor 42b. The anchors 42 are engaged with the tissue T, for example through the use of the introducers described above. A suture 170 is provided having a first end 180 terminated to the eyelet of the anchor 42a, a mid-portion 182 of the suture located between the first anchor 42a and the second anchor 42b, and a portion 184 of the suture in sliding engagement with the eyelet of the second anchor 42b. A free end 186 of the suture 170 is provided, and pulling on the free end 186 of the suture 170 cinches the mid-portion 182 of the suture between the first anchor 42a and the second anchor 42b. In one embodiment, a slide knot 190 or sliding engagement feature 190 is coupled to the suture 170 and is so configured to secure or lock the mid-portion 182 of the suture in a desired position relative to the anchors 22. The slide knot 190 operates to cinch the suture 170 tightly against the support 700 (FIG. 51) against the tissue T.

Some male incontinence treatment devices have several arms, including some form of arms that traverse the obturator foramen and other arms that are implanted anterior to the pubic bone (called pre-pubic arms). The pre-pubic arms are tunnelled anterior to the pelvis and exit the skin of the abdomen.

In contrast, embodiments of the system described above provide a support with two arms that are A) secured to the periosteum alongside the obturator foramen or B) secured to the membrane M covering the obturator foramen or C) secured through the obturator foramen and a system 20 to attach a portion of the support directly and efficiently to the periosteum tissue over the pubic bone. The system obviates the use of additional pre-pubic arms that are tunnelled under and affixed to the skin. The system is easier to implant and reduces the amount of time that the patient is in the operating room.

FIGS. 54-62 are schematic views illustrating embodiments of a method of anchoring a support material to tissue.

Figure 54:
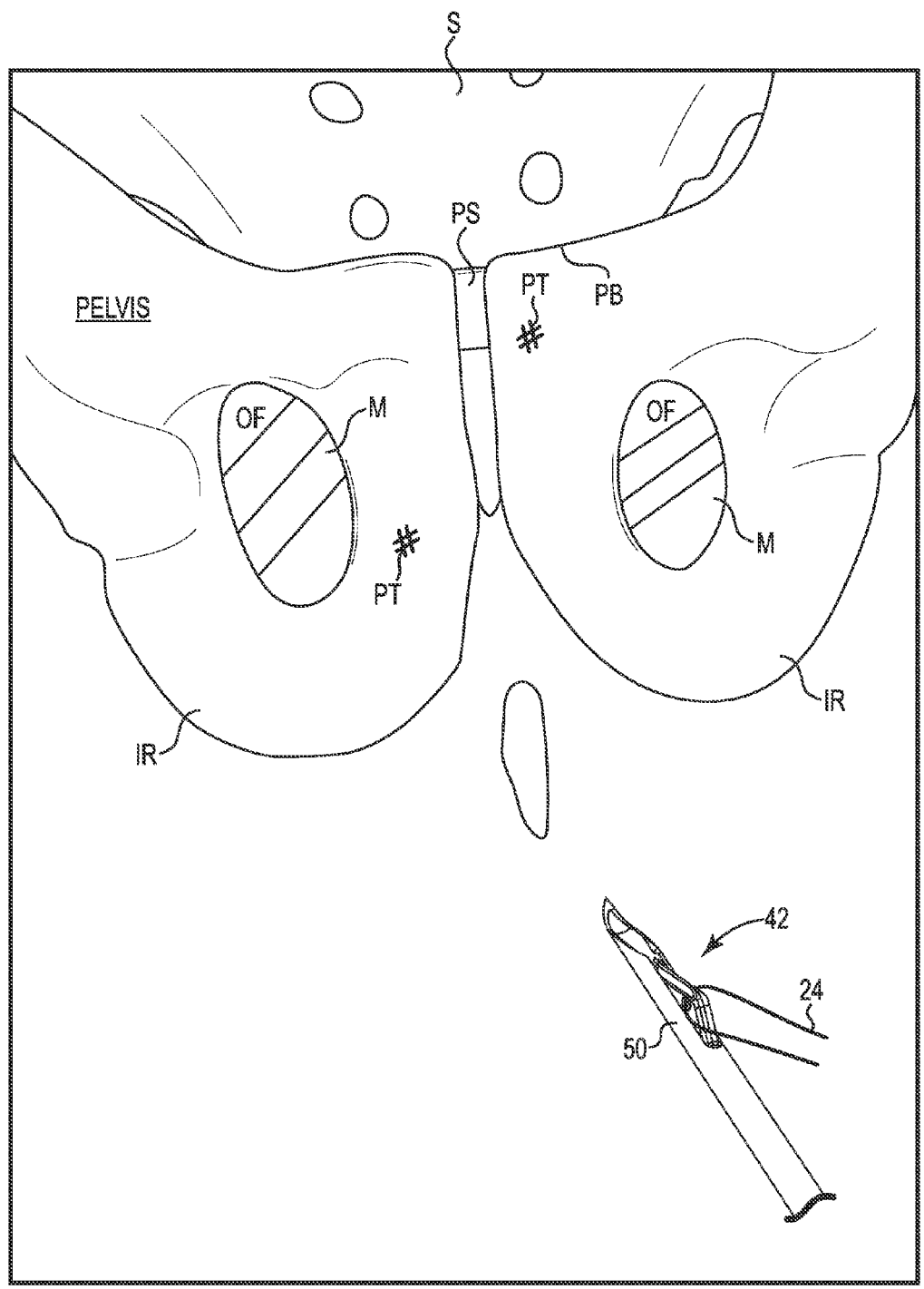
FIGS. 54-62 are schematic views of embodiments of a method of anchoring a support material to tissue.

FIG. 54 is a schematic view of a pelvis. The view has been simplified by not illustrating certain extraneous aspects of human anatomy such as certain of the organs and certain of the muscle and other connective tissues. The view is oriented from a location anterior to the pelvis and shows the sacrum S in the background and the pubic symphysis PS in the foreground.

The patient is prepared for surgery according to the accepted procedures of the hospital or clinic, suitably anesthetized, and placed in a lithotomy position with the feet elevated above the level of the hips and the perineum at the edge of the surgical table. An incision is formed in the urogenital triangle of the patient. The urogenital triangle is that region on a female patient where a base leg of the urogenital triangle is oriented in a horizontal manner between the vagina and the anus, and the pair of generally equilateral legs of the urogenital triangle extending from the base leg meets at an apex above the vertex of the labia. The urogenital triangle is that region on a male patient between the scrotum and the anus. Tissue is dissected away from the incision to access the urethra, and in some procedures, the ischial pubic rami IR.

The method of anchoring a support material to tissue includes first forming the incision in the urogenital triangle of a male patient or a female patient for access to the pelvic anatomy. Thereafter, one of the anchors 42 is placed in the tissue (i.e., not in the bone) leaving the suture 24 trailing out of the incision. The support is delivered along the suture 24 in a distal direction (e.g., along an inward direction) to the location of the anchor 42. The suture 24 is terminated to the support to fixate the support inside the patient. Consistent with this description, the anchor 42 is inserted into the cannula 50 of the introducer. The introducer is now readied to affix the anchor 42 to the tissue.

FIG. 55 is a schematic view of the leading end of the cannula 50 inserted into and guided through the incision. The surgeon palpates for the surface of the pelvis and thereafter pushes the leading end of the cannula 50 into the periosteum tissue PT of the pelvis until the anchor 42 is engaged with (e.g., under) the periosteum tissue PT. Periosteum tissue is a thin sheet of dense fibrous connective tissue that is attached at the outer surface of all bones. The periosteum tissue PT is represented as a hashed area and it is understood that the periosteum tissue PT covers the exterior of the boney pelvis.

Figure 56:
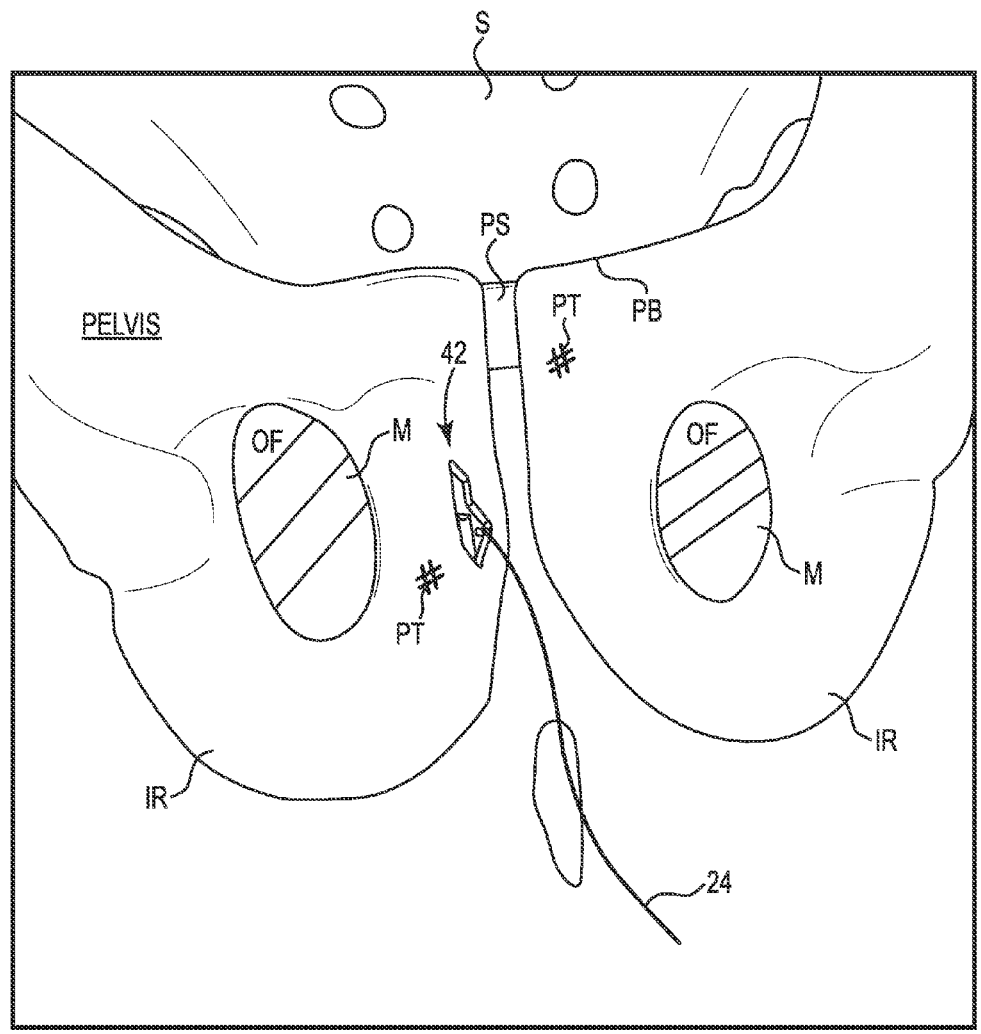

FIG. 56 is a schematic view of the anchor 42 engaged with the periosteum tissue PT. The cannula 50 (FIG. 55) has been withdrawn from an incision leaving the anchor 42 embedded or engaged with the periosteum tissue PT. The anchor 42 is under the periosteum tissue PT and over (or above or superior) to the bone of the pelvis. The anchor 42 is not inserted into the bone of the pelvis. The suture 24 is connected to the anchor 42, and a portion of the suture 24 extends out of the incision and is available (for example as a conduit) to allow the surgeon to deliver support material along the suture 24 to the anchor 42. In this manner, since the anchor 42 is embedded in the periosteum tissue PT a support can be delivered to the anchor and fixed against nearly any bone in the body. Thus, the surgeon need not "aim" for the obturator foramen or other specific tissue landmark; the surgeon simply anchors the anchor 42 into periosteum tissue PT.

Figure 57:
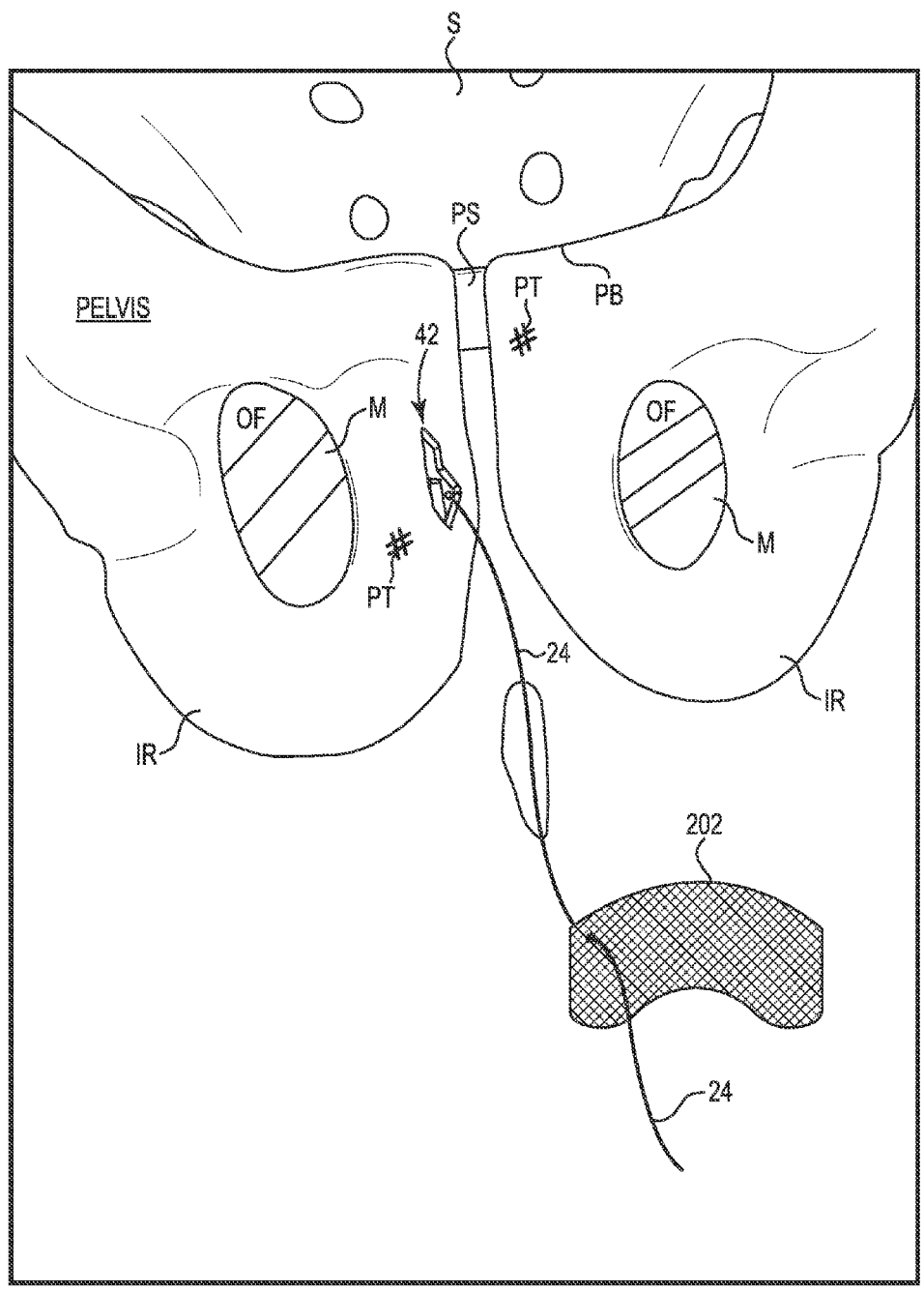

FIG. 57 is a schematic view of support material 202 coupled in sliding engagement with the suture 24. The support material 202 is illustrated in a generalized form. The support material 202 includes an area of a support. In some embodiments, one or more arms or one or more legs extend from the area of support material 202. In some embodiments, the support material 202 is just an area of material without arms or legs, for example a trapezoid or a rectangle of material that allows the surgeon to trim a desired shape (i.e., a "trim-to-size" support). The support material 202 is acceptably fabricated from the material of the support 700 described above.

The surgeon secures the support material 202 to the suture 24, for example by guiding the suture 24 through a pore or other opening of the support material 202. If the support material is a solid and does not have an opening, the surgeon employs a needle to direct the suture 24 through the support material 202. The portion of the suture 24 that extends out incision allows the surgeon to conveniently couple the support material 202 to the suture 24 outside of the patient's body.

Figure 58:
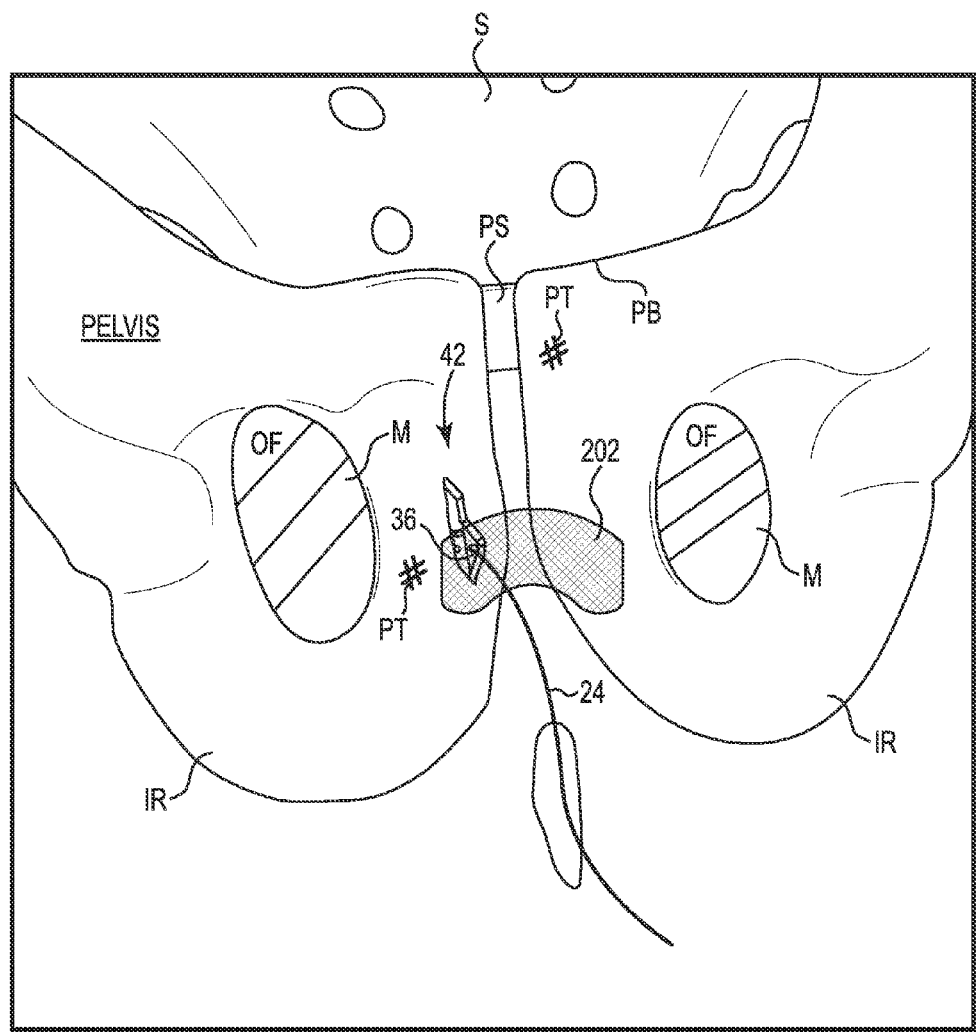

FIG. 58 is a schematic view of the support material 202 having been delivered along the suture 24, through the incision, in a distal direction to the patient's pelvis. The surgeon uses an instrument, or perhaps a finger, to guide the support material 202 through the incision inward toward the pelvis. The anchor 42 is buried or otherwise implanted into the periosteum tissue PT, and the support material 202 is proximal to the anchor 42.

Figure 59A:
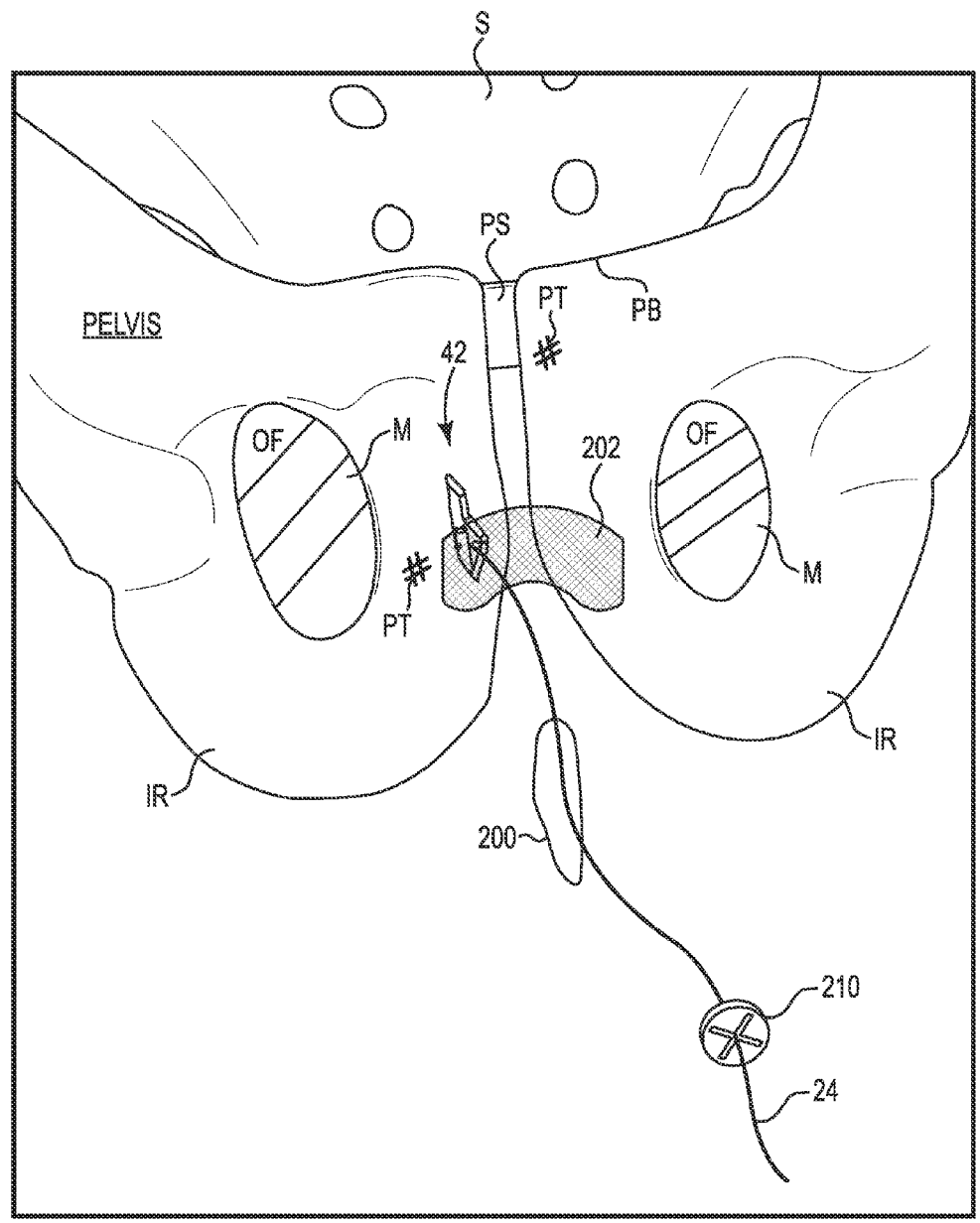

FIG. 59A is a schematic view of the support material 202 located between the anchor 42 and a stopper 210. The support material 202 has been delivered through the incision to the pelvis of the patient, and the stopper 210 is configured to engage with the suture 24 and fixate the support material 202 against the pelvis. The anchoring of the support material 202 to the pelvis will support the urethra of the patient. The stopper 210 is configured such that sliding the stopper 210 along the suture 24 will forcibly affix the support material 202 to the patient. In one embodiment, the stopper 210 is configured for one-directional sliding along anchor 42, for example, only in a direction into the patient. The stopper 210 includes fingers that prevent the stopper 210 from moving in the direction out of the patient's body.

Figure 59B:
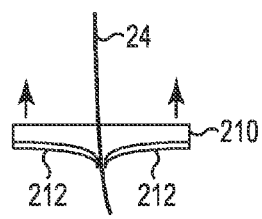

FIG. 59B is a schematic side view of the stopper 210 and the fingers 212. The fingers 212 are deflected to diverge away from the patient's body, which allows the stopper 210 to move along the suture 24 in the direction into the patient's body as indicated by the arrows. The stopper 210 is configured as a unidirectional stopper that is allowed to move in one direction along the suture 24. Attempted movement of the stopper 210 in the opposite direction causes the fingers 212 to impinge against the suture 24, which prevents movement of the stopper 210 of the patient's body.

Figure 60:
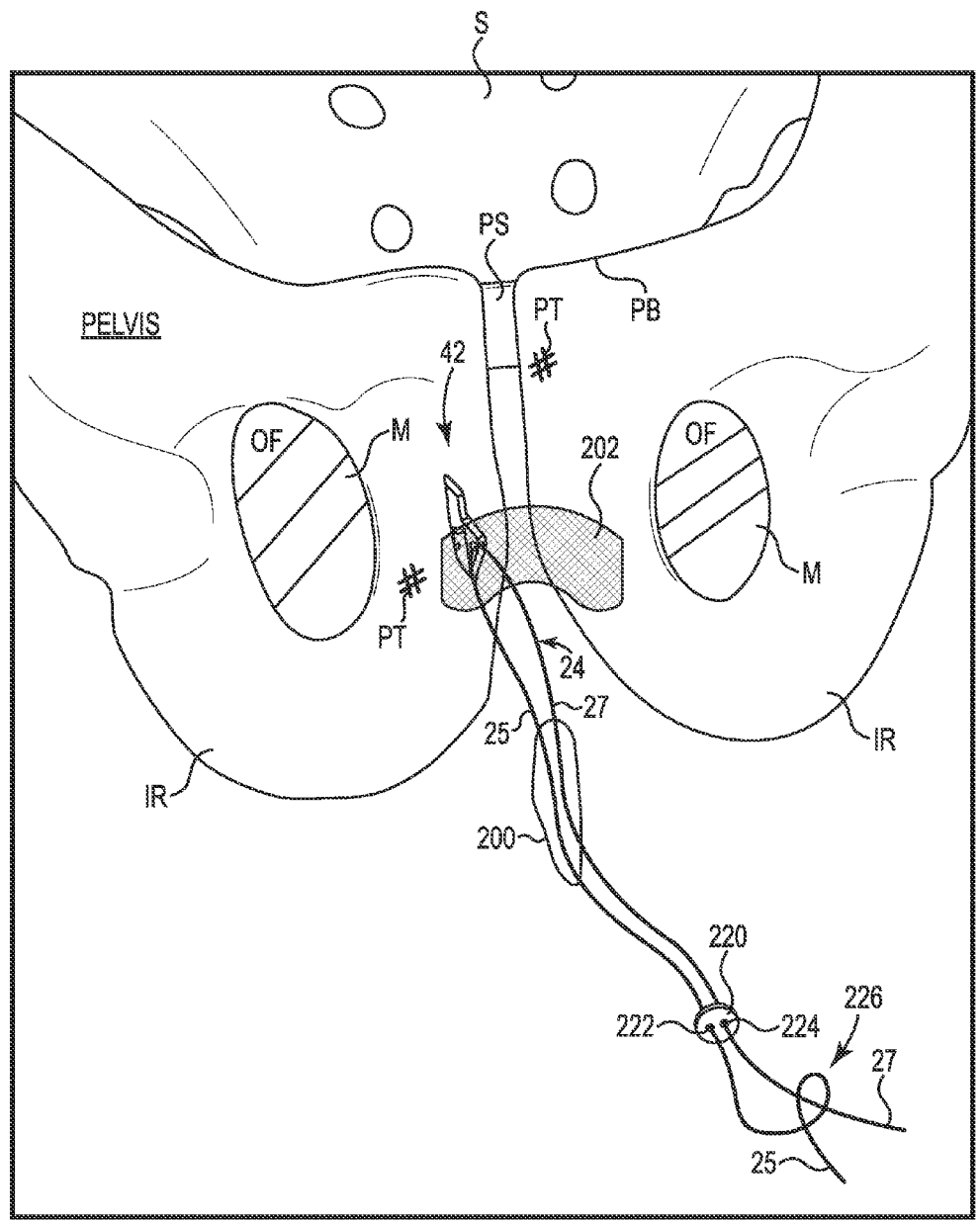

FIG. 60 is a schematic view of one embodiment of a stopper 220 provided to secure the support material 202 within the patient. The stopper 220, also referred to as a button 220, includes a first orifice 222 and a second orifice 224. The suture 24 includes a first strand 25 that is inserted through the first orifice 222 and a second strand 27 that is inserted through the second orifice 224. The button 220 is operable to slide along the suture 24 as the strands 25, 27 slide through the orifices 222, 224, respectively. In this manner, the button 220 is operable to be delivered through the incision and into the patient. It is desirable to secure the button 220 against the support material 202. In one embodiment, the first strand 25 is tied to the second strand 27 to provide a slip knot 226. Pulling on the free end (e.g., strand 25) drives the slip knot 226 in a distal direction into the patient until the slip knot is secure against the button 220. Eventually, that portion of the suture 24 that is proximal of the button 220 is tied or otherwise terminated, and the excess suture 24 is removed by the surgeon.

Figure 61:
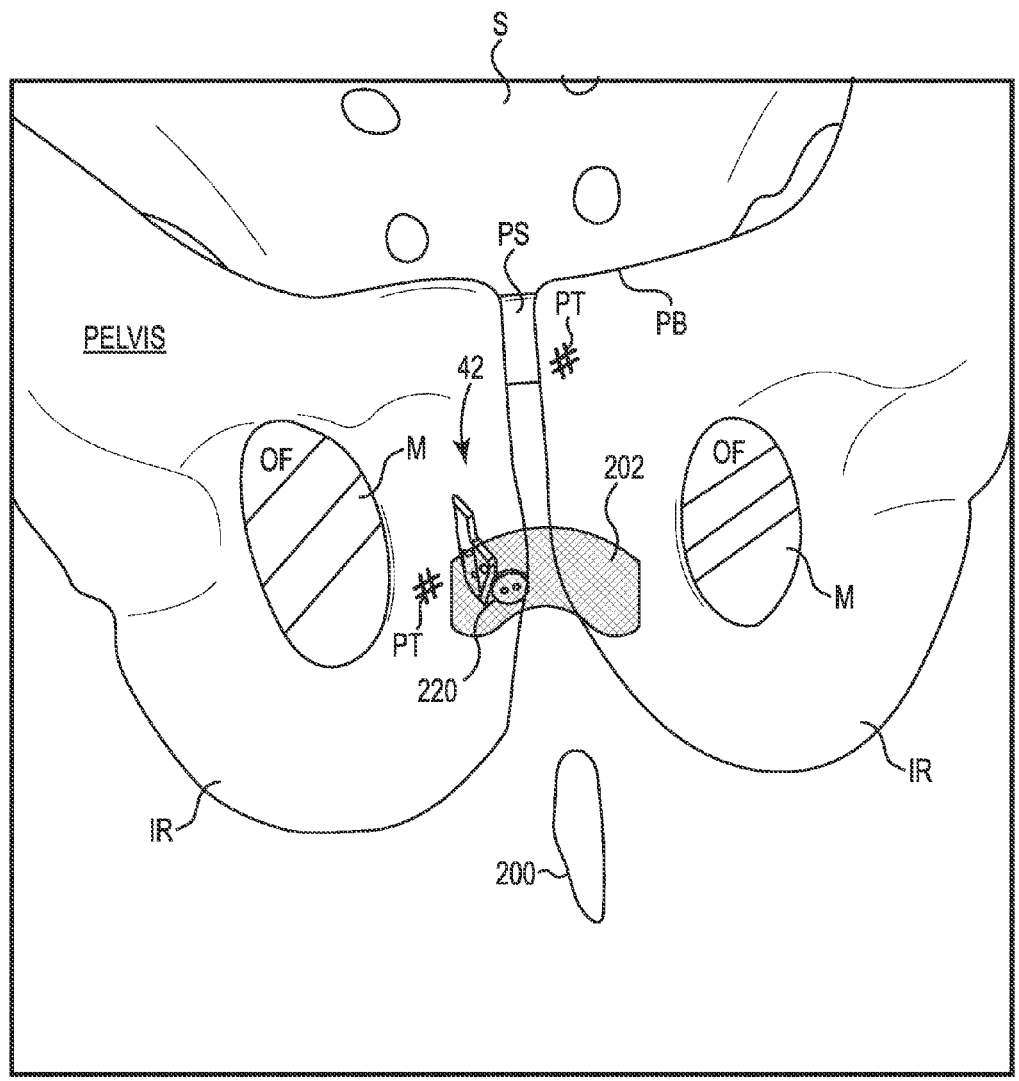

FIG. 61 is a schematic view of the support material 202 secured to the patient and located between anchor 42 and the stopper 220 (or button 220). The excess portion of the suture 24 has been removed. Other portions of the support material 202 may also be secured to other tissue of the patient, for example in a bilateral manner by using the introducer and the anchor 42 as described above.

Figure 62:
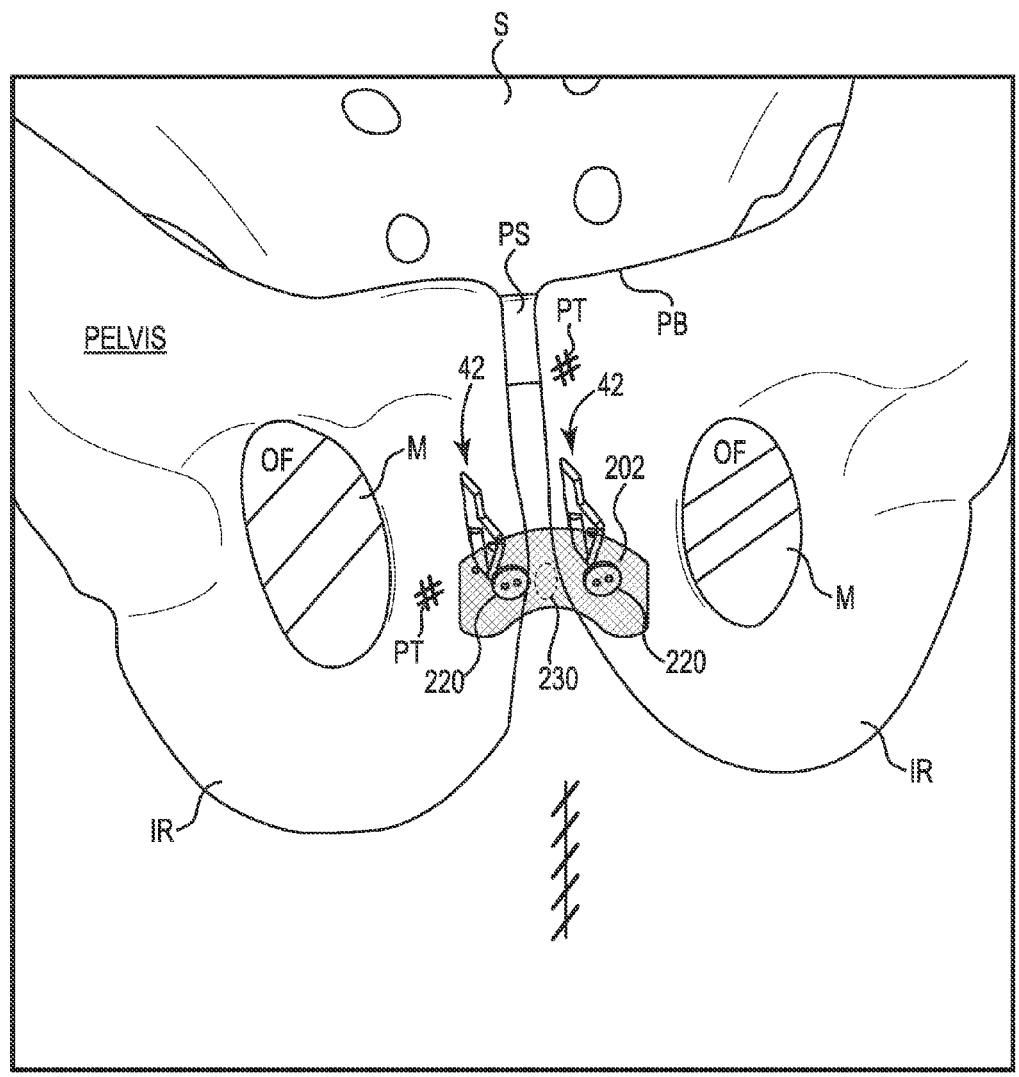

FIG. 62 is a schematic view of the support material 202 secured to the periosteum tissue PT of the patient on either lateral side of the pubic symphysis PS. The support material 202 is secured or fixated at two locations, a left side location (relative to the view of FIG. 64) and a right location. Each fixation location has the support material 202 positioned between the anchor 42 lodged in the periosteum tissue and the stopper 220, with the excess portion of the suture 24 removed. When the surgeon is satisfied that the support material 202 is appropriately placed and fixated, the incision is closed.

In the case of a male patient, the support material 202 has a trapezoidal shape that is sized to support the bulbar urethral complex 230 (muscle and other tissue) and elevate and support the male urethra. The support material 202 in the case of the male patient is typically secured in more than two bilateral locations to allow substantial support and elevation to the longer male urethra.

In the case of a female patient, the support material 202 has a rectangular (e.g., "sling") shape of about 1 cm wide by 5-10 cm long that is sized to extend across the descending rami to support the short (~2 cm) female urethra 230. The support material 202 in the case of the female patient is typically secured in two bilateral locations to provide support without compression (or with reduced compression to the urethra).

FIGS. 63-68 are schematic views illustrating embodiments of a method of anchoring a support 310 to tissue. The support 310 is a rectangular sling-style of support as is appropriate for treating female urinary incontinence.

Figure 63:
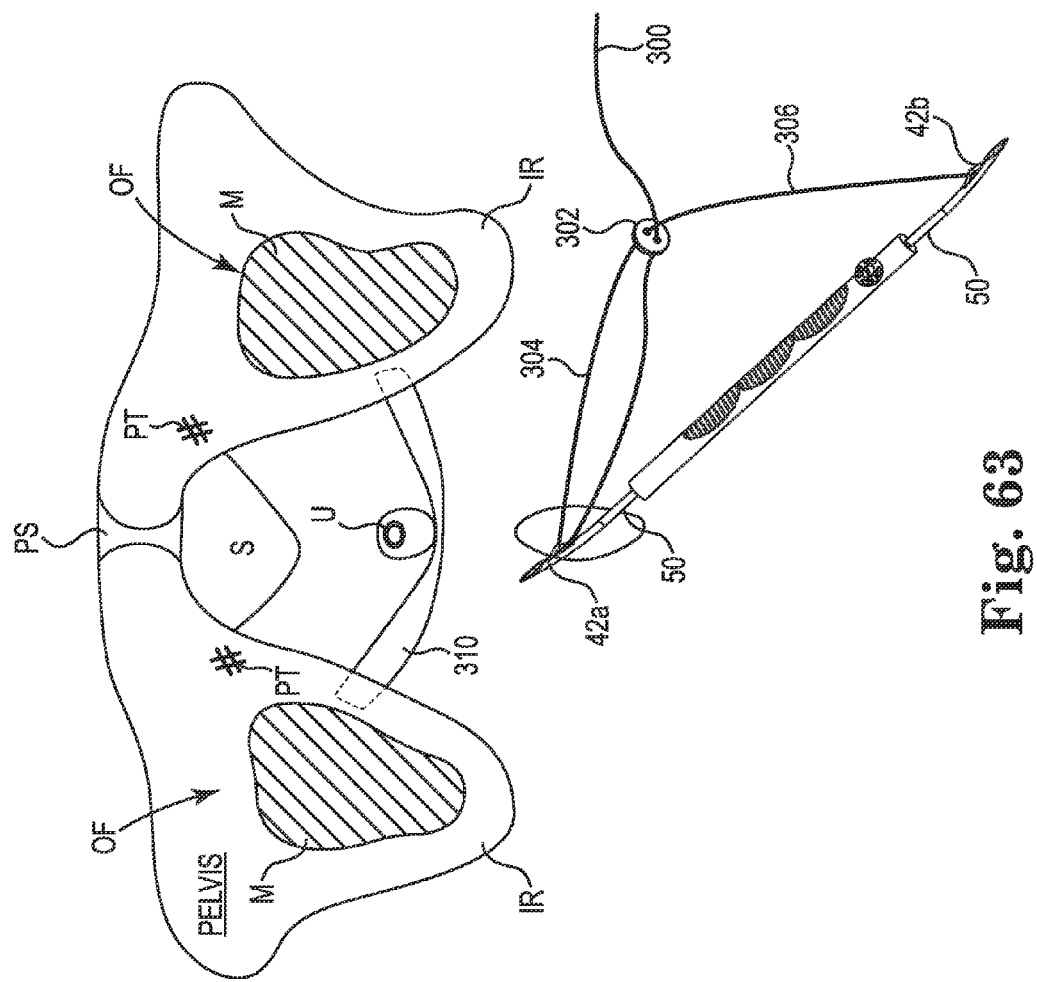

FIG. 63 is a schematic view of the system employed to secure the support 310 to the pelvis. The system includes the first anchor 42*a* inserted into the first cannula 50, the second anchor 42*b* inserted into the second cannula 50, and a length of suture 300 connected between the first anchor 42*a* and the second anchor 42*b*. The suture 300 is provided to slide relative to the first anchor 42*a* and includes a stopper 302 that fixes the suture 300 in a position selected by the surgeon.

Aspects of the surgical procedure include forming an incision in a urogenital triangle, for example in the upper wall of the vagina and dissecting tissue to identify each of the two descending ischial pubic rami IR. The support 310 is inserted in the incision after suitable dissection of the tissue. The system is employed to anchor or fixate the support 310 in a position inferior to (under) the urethra U.

The anchor 42a is loaded into the first cannula 50 and the cannula 50 is introduced into the incision.

Figure 64:
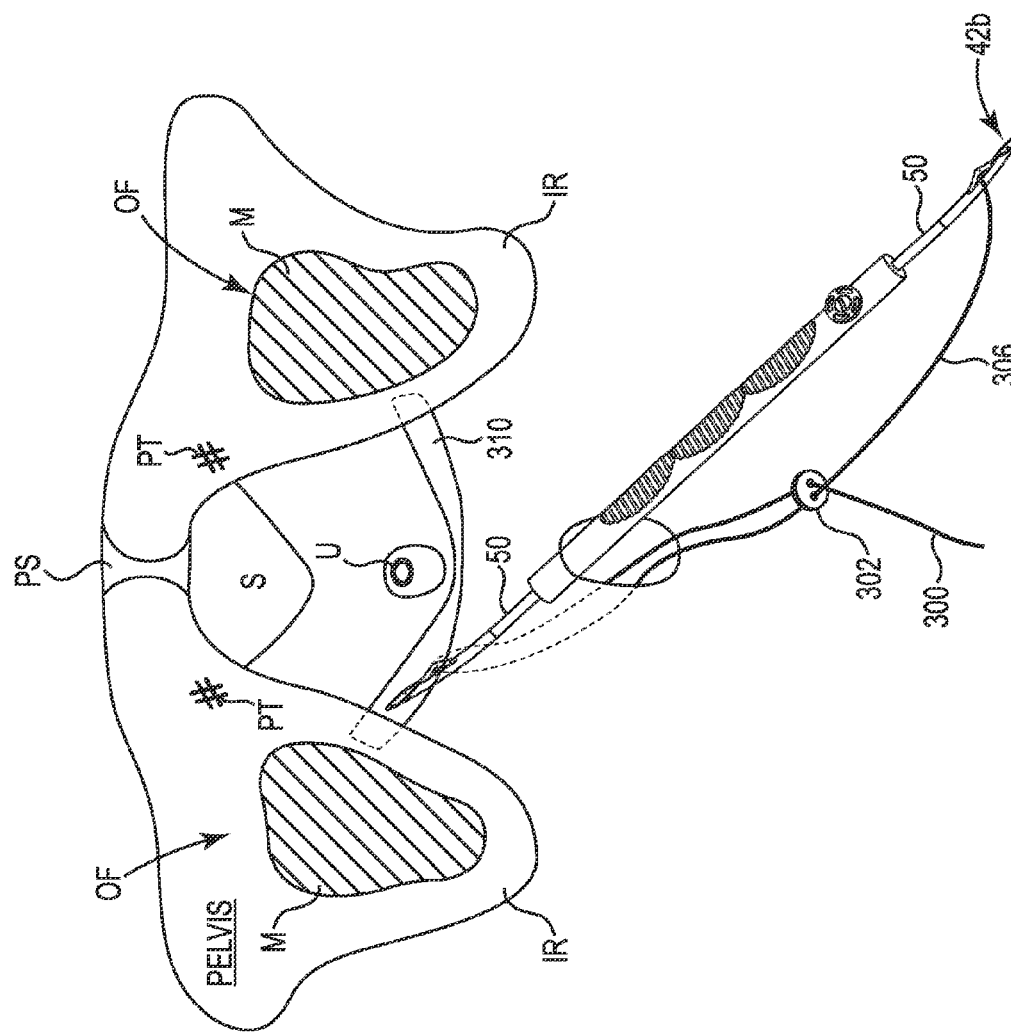

FIG. 64 is a schematic view of the support 310 relative to the pelvis and illustrates the first cannula 50 inserted through the incision, posterior the ramus IR, and through the support 310 until the leading end of the cannula 50 slides under the periosteum tissue PT. The leading end of the cannula 50 is sharp and so configured to pierce the periosteum tissue PT and deliver the anchor 42a between the bone and under the periosteum tissue PT.

Figure 65:
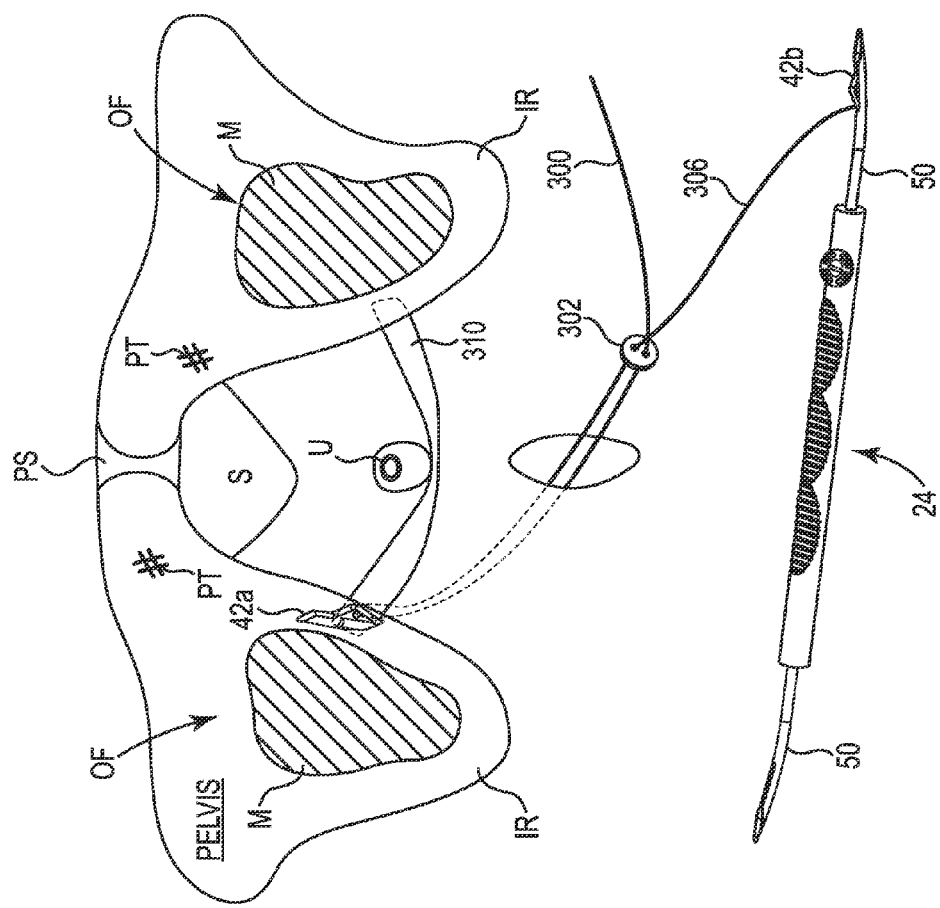

FIG. 65 is a schematic view of the first cannula 50 withdrawn from the incision leaving the first anchor 42a embedded in or secured to the periosteum tissue PT. The suture 300 trails away from the first anchor 42a out of the patient through the incision.

Figure 66:
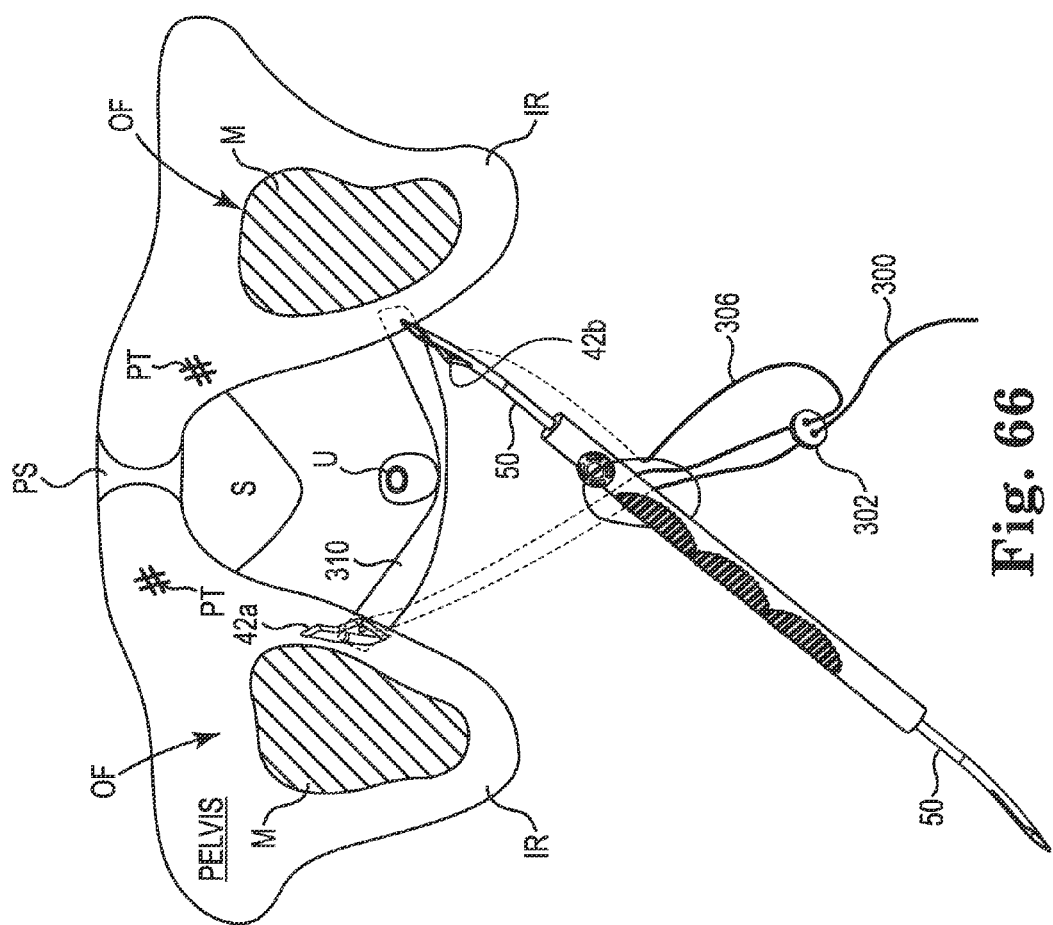

FIG. 66 is a schematic view of the second cannula 50 inserted into the incision, posterior to the ramus IR, and through the support 310. The surgeon directs the introducer in a distal direction until the sharp distal end of the cannula 50 pierces the periosteum tissue PT and delivers the anchor 42b. The suture 300 remains connected between the first anchor 42a and the second anchor 42b, and the stopper 302 is outside of the patient's body.

Figure 67:
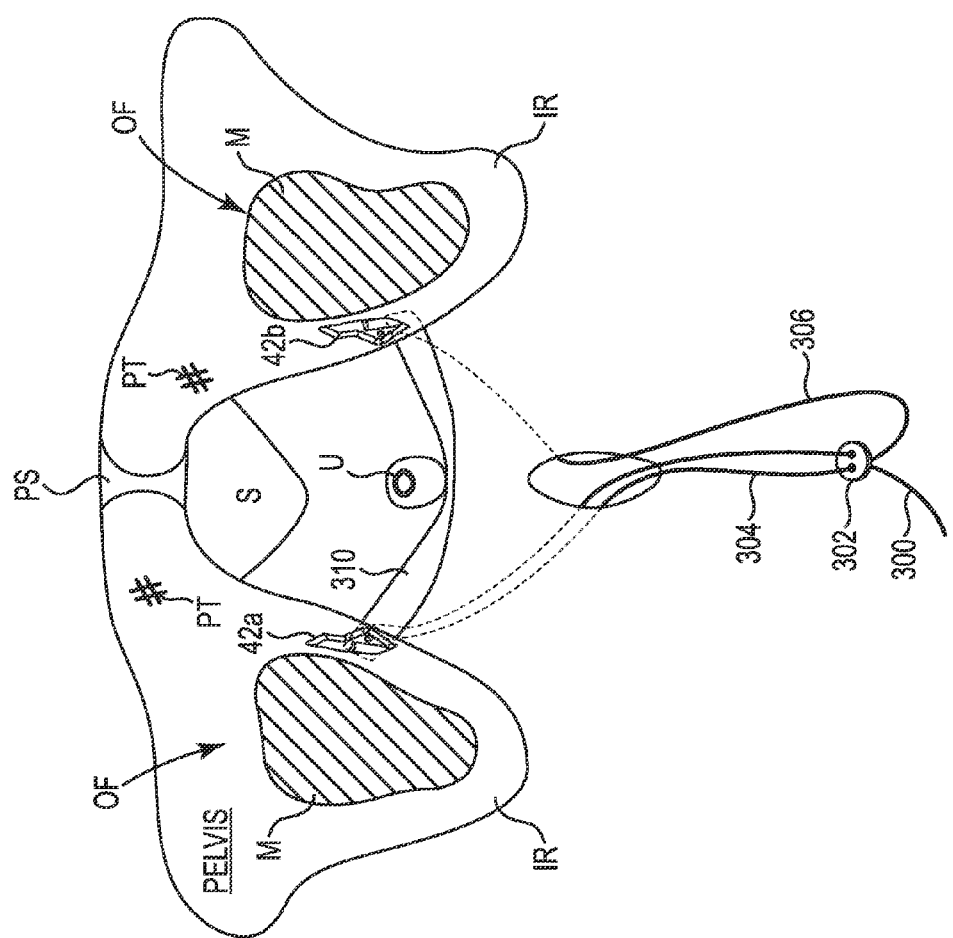

FIG. 67 is a schematic view of the support 310 secured on a first side by the first anchor 42a and secured on an opposite second side by the second anchor 42b. The suture 300 is looped through the first anchor 42a and includes a first segment 304 between the anchor 42a and the stopper 302, a second segment 306 between the stopper 302 and the anchor 42b, and the trailing portion 300. Pulling on the trailing portion 300 operates to cinch the stopper 302 into a supporting configuration against the support 310.

FIG. 68A is a schematic view of the support 310 secured relative to the pelvis, and FIG. 68B is a bottom view of the support 310 as secured between the opposed descending rami IR. The trailing portion 300 of the suture has been pulled by the surgeon in a proximal direction resulting in the stopper 302 being guided up to the support 310. The stopper 302 is configured to engage with the suture 300 and maintain the support 310 in position relative to the urethra U.

FIG. 68B illustrates the first segment 304 of the suture with the slack removed and tightened against the support 310, and the second segment 306 of the suture with the slack removed and tightened against the support 310. The stopper 302 secures the segments 304, 306 against the support 310.

Embodiments described above include pushing the pointed leading end of the cannula 50 through both the support 310 and the periosteum tissue PT to secure the anchor 42 in the patient. The trailing suture 300 is accessible by the surgeon outside of the patient's body to allow the surgeon to direct the stopper 302 upwards (or inwards) to the support 310.

In an alternative embodiment of this approach, the surgeon pushes the leading end of the cannula 50 into the periosteum tissue PT of the first ramus IR and engages the first anchor 42a in the periosteum tissue, while leaving a single strand of suture 300 trailing from the first anchor 42a and out of the vaginal incision. The surgeon completes a similar process on the contralateral side by pushing the leading end of the cannula 50 into periosteum tissue PT of the second ramus IR and engaging a second, different anchor 42b with the periosteum tissue PT. A second, separate suture strand is left trailing from the second anchor and out of the vaginal incision. Along these two trailing suture strands the surgeon delivers a first end portion of a sling 310 along the first suture strand, through the vaginal incision and to the first ramus IR of the pelvis, and a second end portion of the sling 310 along the second suture and through the vaginal incision to the second ramus IR of the pelvis. The surgeon subsequently secures each suture strand, for example by tying the strand to form a knot at the sling 310.

Embodiments described above include pushing the pointed leading end of the cannula 50 through both the support 310 and the periosteum tissue. The trailing suture 300 is accessible by the surgeon outside of the patient to allow the surgeon to direct the stopper 302 upwards (or inwards) to the support 310. In an alternative embodiment of this approach, the surgeon fixates a support material 310 between opposed membranes M of the opposed obturator foramen OF. In such a procedure, the surgeon guides the leading end of the cannula 50 through a first end portion of the sling 310, through the vaginal incision, and into the membrane M of the first obturator foramen OF to engage the first anchor with the membrane M, thus leaving a suture connected to the first anchor. The surgeon performs a similar procedure on the contralateral side by loading another anchor into the cannula 50 and guiding the leading end of the cannula 50 through a second end portion of the sling 310, through the vaginal incision, and into a membrane M of a second obturator foramen OF. The surgeon engages the second anchor with the membrane M, where the suture is coupled to the second anchor. The surgeon pulls on a free end of the suture and secures the first end portion of the sling 310 to the first membrane M of the first obturator foramen OF and secures the second end portion of the sling 310 to the membrane M of the second obturator foramen OF.

FIGS. 69-73 are schematic views of embodiments of a method of anchoring a support to tissue.

Figure 69:
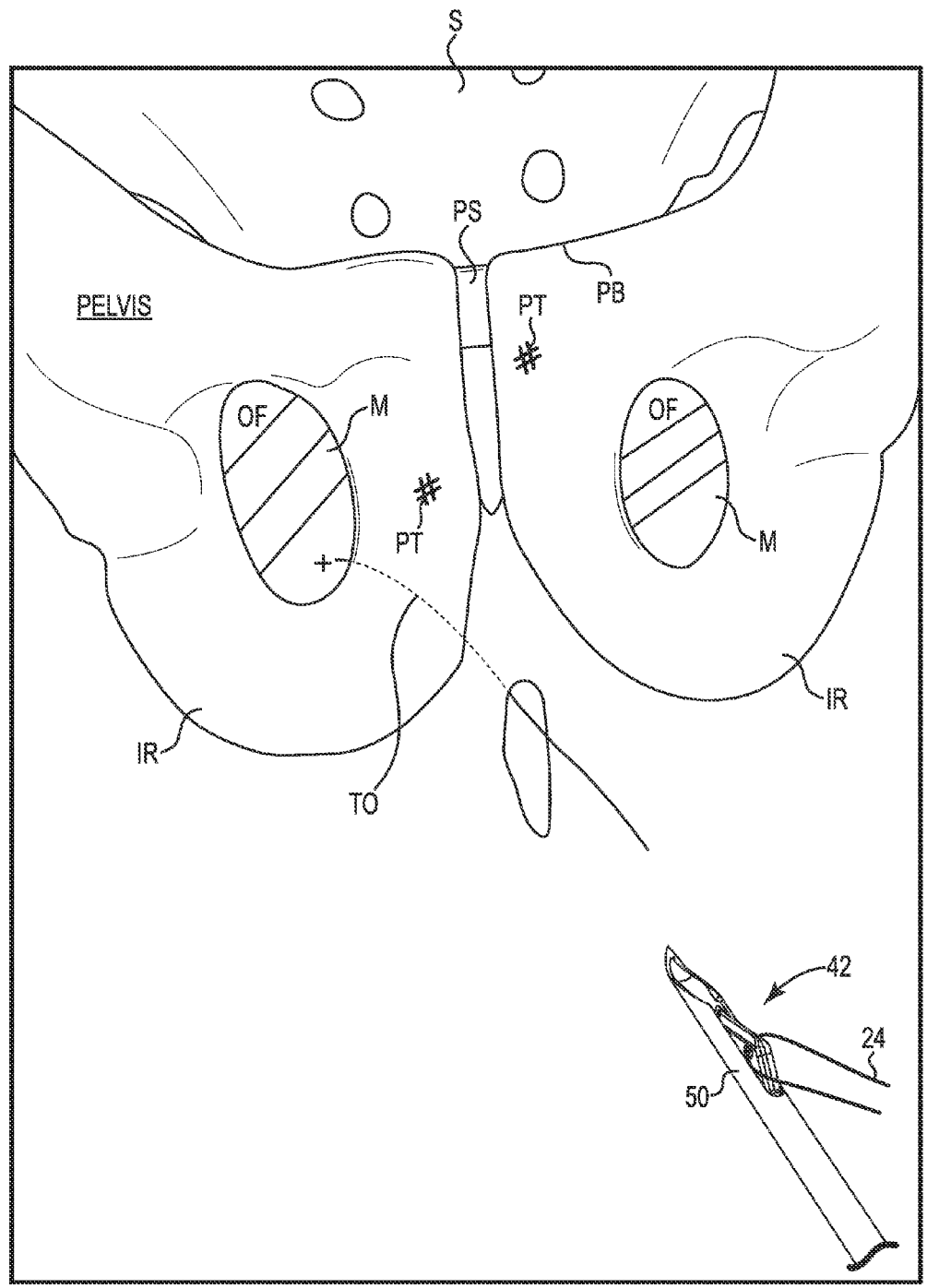
FIGS. 69-73 are schematic views of embodiments of a method of anchoring a support material to tissue.

FIG. 69 is a schematic view of a trans-obturator TO path that is followed by the cannula 50 to place the anchor 42 into the membrane M of the obturator foramen OF. The trans-obturator TO path extends from the incision posterior to the ramus (i.e., behind the ramus) and into the membrane M. It is desirable to place the anchor 42 in a lower quadrant of the membrane M. In one approach, the surgeon palpates along the inferior portion of the ramus IR and guides the cannula 50 along and behind the ramus IR into the membrane M.

Figure 70:
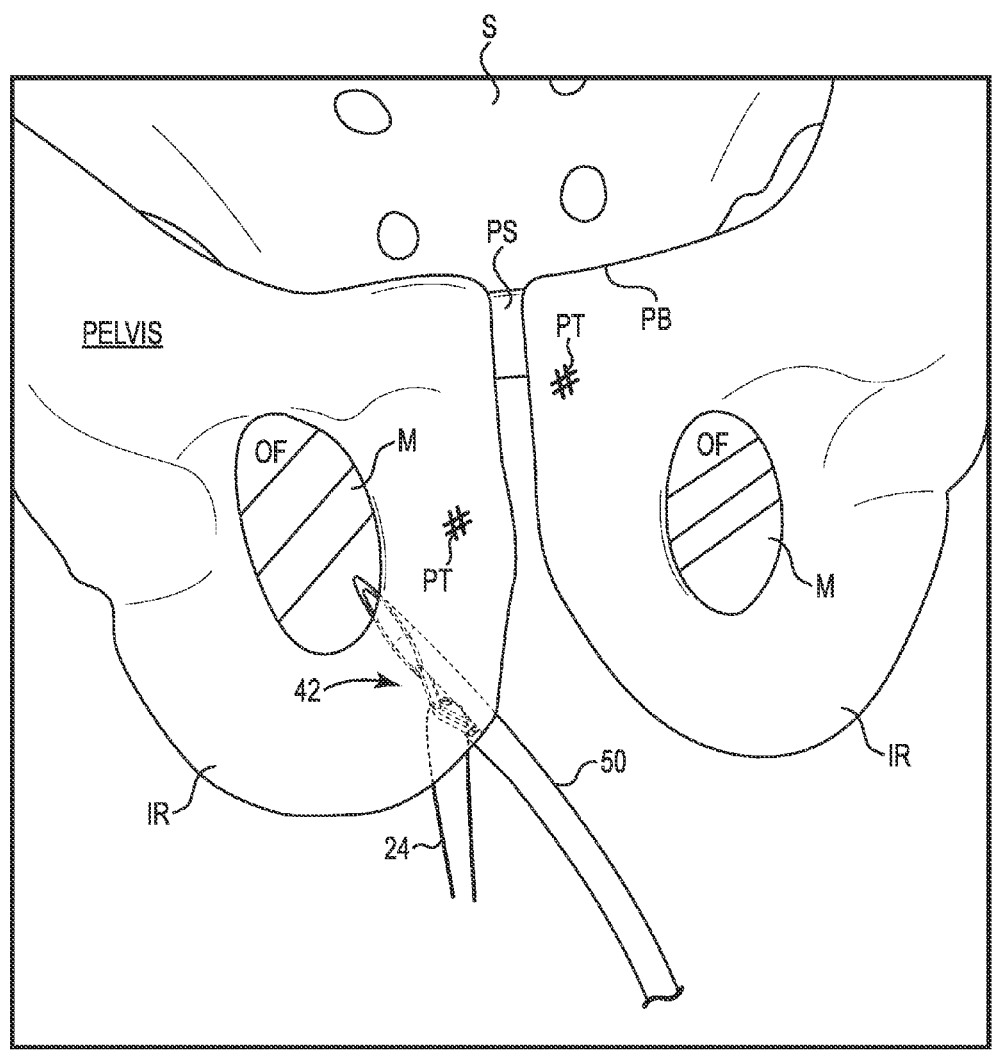

FIG. 70 is a schematic view of the cannula 50 introduced along the trans-obturator TO path posterior to the ramus IR and into the membrane M. The surgeon provides a pushing distal force that drives the anchor 42 into, but not through, the membrane M. The anchor is placed in the muscle of the OF membrane and not driven all the way through the membrane M from the posterior side to the anterior side. However, in one embodiment the anchor 42 is inserted entirely through the obturator foramen OF from the posterior side to the anterior side of the membrane M.

Figure 71:
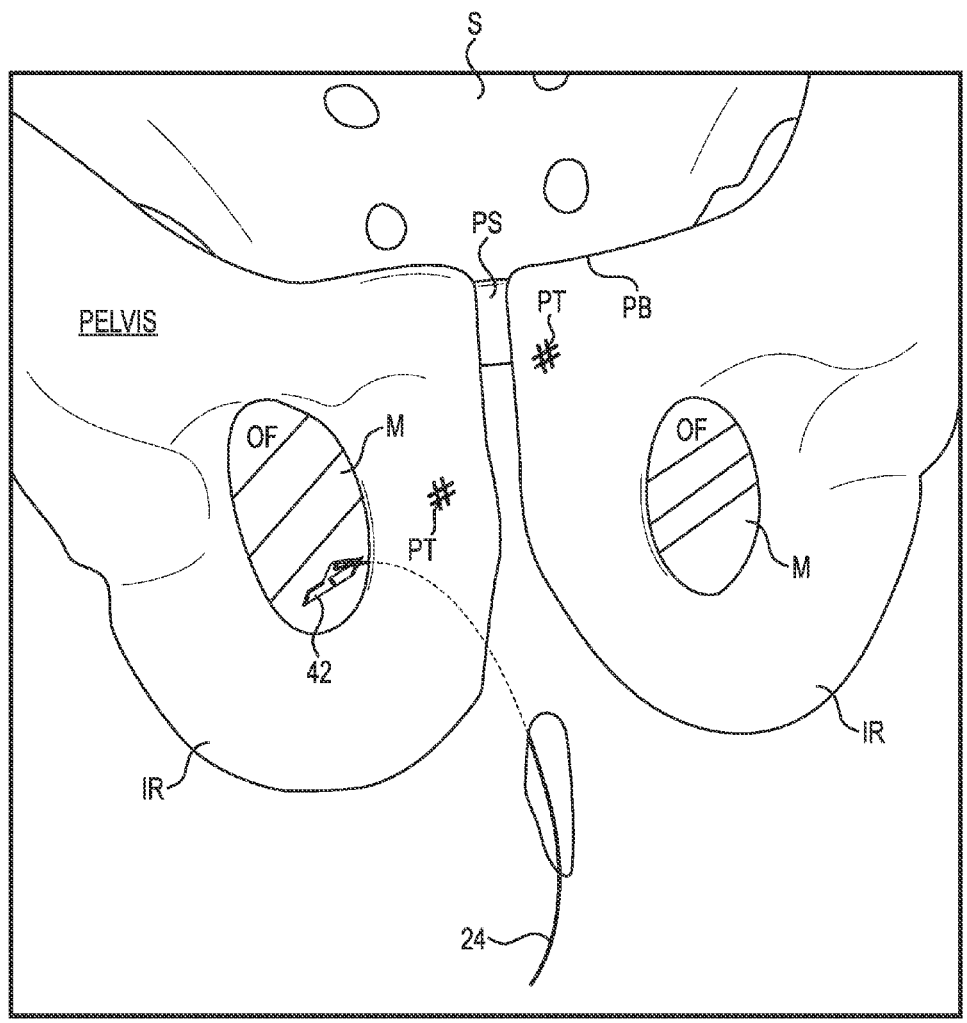

FIG. 71 is a schematic view of the anchor 42 inserted into the membrane M with the suture 24 extending posterior to the ramus IR and out of the incision. In this configuration, the suture 24 is available to deliver support material or other materials along the trans-obturator TO path posterior to the ramus IR upwards to the membrane M that covers the obturator foramen OF.

Figure 72:
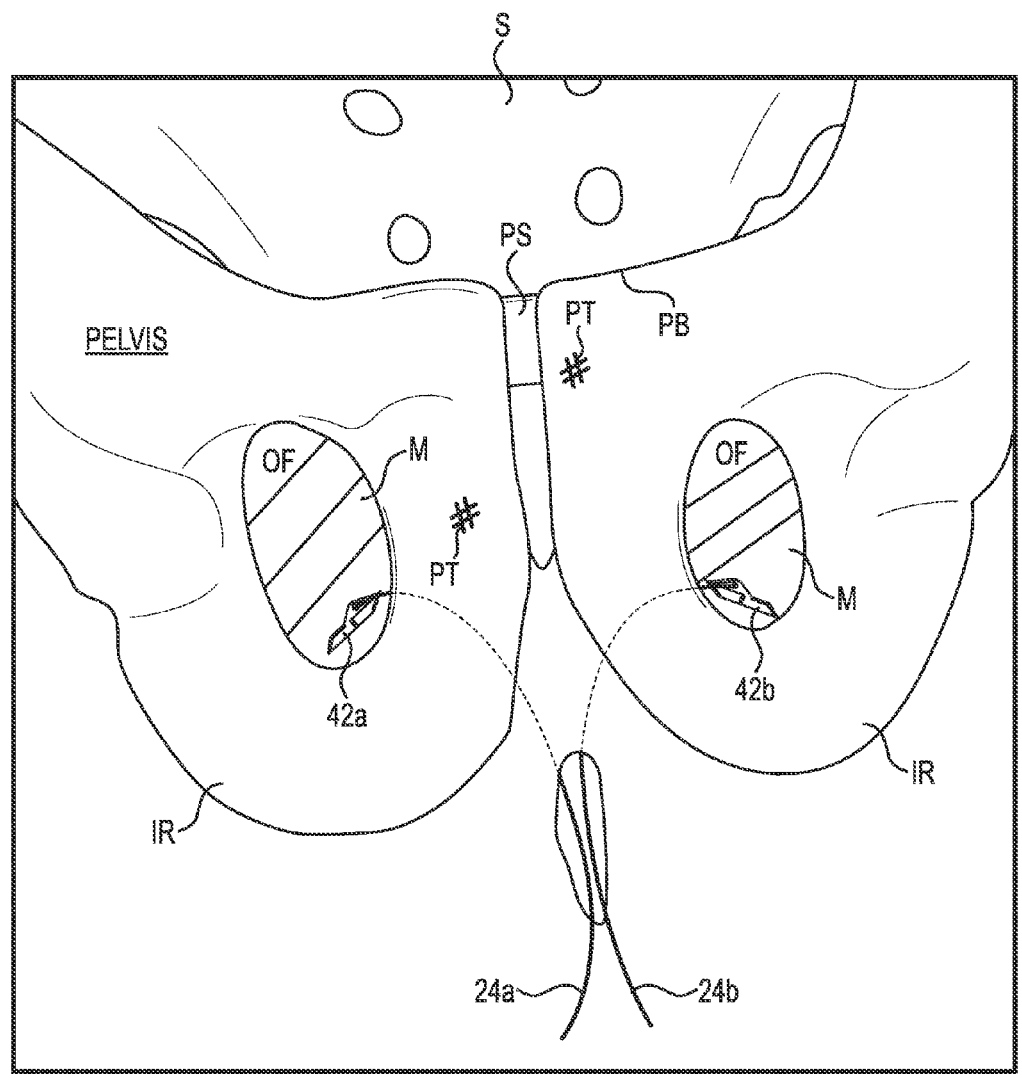

FIG. 72 is a schematic view after the surgeon completes the process described in FIGS. 69-71 on the contralateral side. The cannula 50 of the introducer has been directed along the trans-obturator TO path posterior to the ramus IR until the anchor 42b is positioned and inserted into the membrane M covering the obturator foramen OF. The suture 24b trails away from the anchor 42b and exits the incision. With this configuration, the first suture 24a is connected to the first anchor 42a that secured in a first one of the membranes M of the obturator foramen OF, and the second suture 24b is connected to the second anchor 42b that is secured in the membrane M of the opposed second obturator foramen OF. The sutures 24a, 24b extend out of the incision and are available to deliver the support material through the incision to support the urethra or other body organ.

Figure 73:
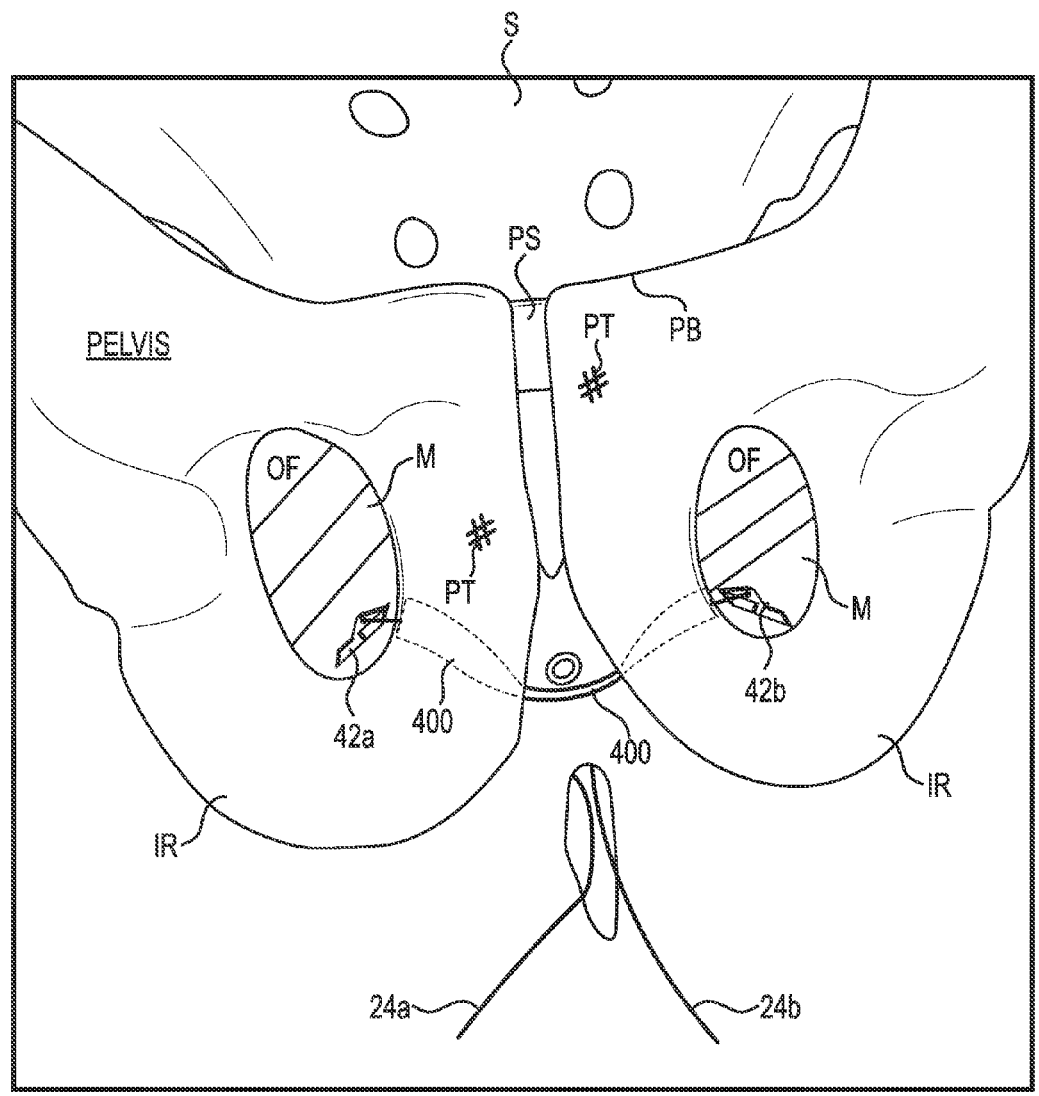

FIG. 73 is a schematic view of a support 400 inserted into a patient. A first end of the support 400 has been engaged with and delivered along the entire length of the first suture 24a to the anchor 42a. A second end of the support 400 has been engaged with and delivered along the entire length of the second suture 24b up to the second anchor 42b. The support 400 thus extends like a hammock from the first anchor 42a in the first membrane M of the first obturator foramen OF across the midline of the patient to the second anchor 42b in the second membrane M of the second obturator foramen OF. The surgeon terminates the first suture 24a at the support 400, for example by tying a knot, and likewise terminates the second suture 24b at the support 400. The excess length of suture 24a, 24b is removed and the incision is closed.

Figure 74:
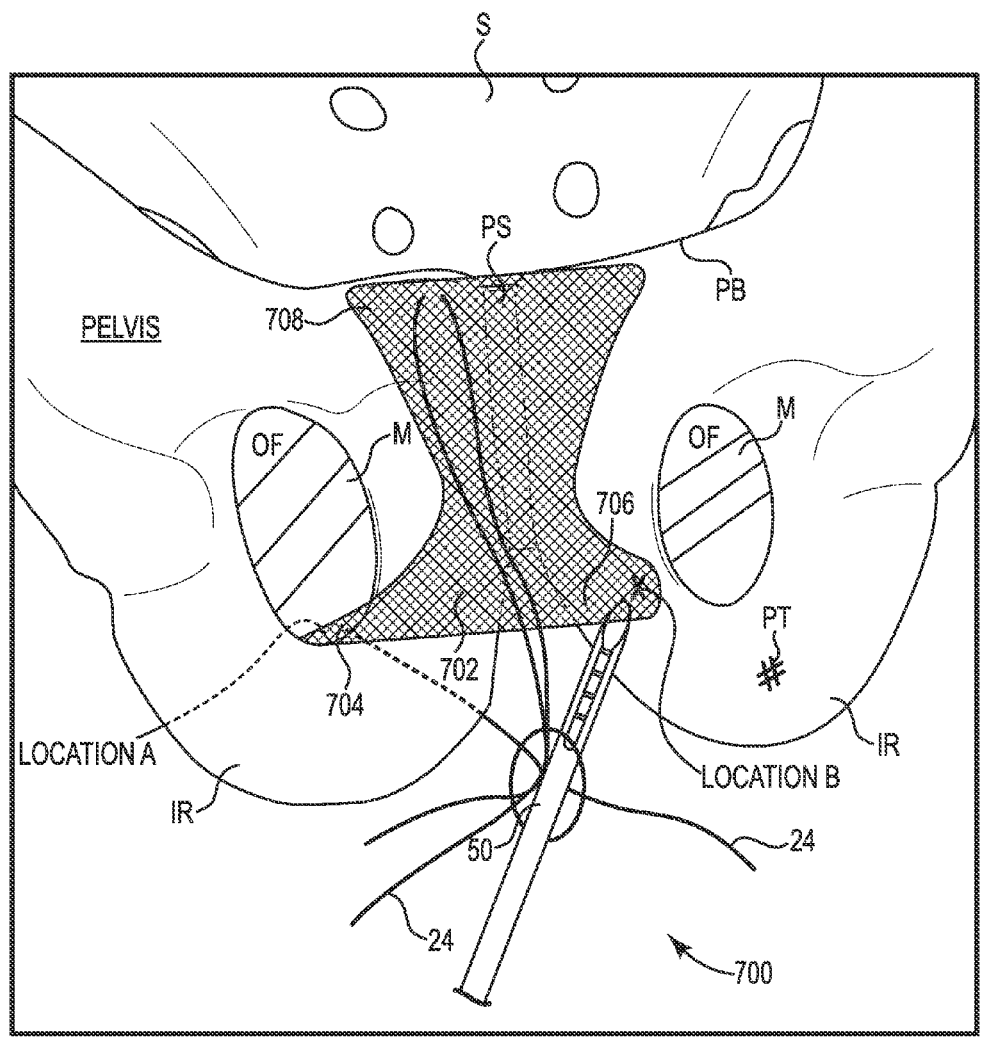
FIG. 74 is a schematic view illustrating embodiments of methods of anchoring a support to the pelvis of a male patient.

FIG. 74 is a schematic view illustrating embodiments of methods of anchoring the support 700 to the pelvis of a male patient. The pre-pubic side 708 of the support 700 is anchored at a superior location of the pelvis to the periosteum tissue anterior the pubic bone PB. The arms 704, 706 of the support 700 are suitably anchored to the periosteum tissue PT of the inferior ischial pubic ramus IR (anterior or posterior) or to the membrane M of the pelvis.

The method includes elevating and compressing the bulbar urethra of the male patient and includes:
forming a perineal incision in the male patient;
inserting a first arm 704 located on a first side of the support 700 into the perineal incision, directing an end portion of the first arm 704 toward an obturator foramen OF of the pelvis, and fixing the end portion of the first arm 704 to either Location A) the membrane M of the obturator foramen OF or Location B) the periosteum tissue of the ramus IR adjacent to the obturator foramen OF; and
inserting a second arm 706 located on a second side of the support 700 into the perineal incision, directing an end of the second arm 706 toward a second obturator foramen OF of the pelvis, and fixing the end portion of the second arm 706 to one of C) the membrane M of the second obturator foramen OF or D) the periosteum tissue of the ramus IR adjacent to the second obturator foramen OF; and
inserting a pre-pubic side 708 of the support 700 into the perineal incision and directing the pre-pubic side 708 of the support 700 anterior to the pelvis towards a pubic bone PB of the pelvis; and
pushing the anchor 42 through the pre-pubic side 708 of the support 700 and into periosteum tissue PT over the pubic bone PB and engaging the anchor 42 in the periosteum tissue PT of the pubic bone PB; and
securing the pre-pubic side 708 of the support 700 against the periosteum tissue PT of the pubic bone PB.

The arms 704, 706 of the support 700 are suitably anchored to the periosteum tissue PT posterior to (i.e., behind) the ischial ramus IR or anterior to the ischial ramus IR. Mindful of this, and as examples, FIG. 74 illustrates the arm 704 anchored to the membrane M at a posterior location relative to the ischial ramus IR (Location A) and the arm 706 anchored to the anterior surface of the ischial ramus IR (Location B). It is suitable to attach either arm 704, 106 to the inferior edge of the ischial pubic ramus IR.

An addition to the method of anchoring the support 700 relative to the pelvis includes: inserting a body portion of the anchor 42 into a lumen in a cannula 50; inserting a leading end of the cannula 50 and the anchor 42 into the perineal incision; and pushing the leading end of the cannula 50 and the anchor 42 into the periosteum tissue PT of the pubic bone PB.

An addition to the method of anchoring the support 700 relative to the pelvis includes: leaving a suture 24 attached to the anchor 42 trailing from the anchor 42 and out of the perineal incision; and tying the suture 24 against the pre-pubic 708 side of the support 700 and fixing the pre-pubic side 708 of the support 700 against the periosteum tissue PT of the pubic bone PB.

An addition to the method of anchoring the support 700 relative to the pelvis includes: leaving the suture 24 attached to the anchor 42 trailing from the anchor 42 and out of the perineal incision; and sliding a stopper 150 attached to the suture 24 from the perineal incision inward toward the pubic bone PB and fixing the pre-pubic side 708 of the support 700 against the periosteum tissue PT and between the stopper 150 and the pubic bone PB.

An addition to the method of anchoring the support 700 relative to the pelvis includes: inserting a body portion of the anchor 42 into a lumen in a cannula 50; inserting a leading end of the cannula 50 and the anchor 42 into the perineal incision; pushing the leading end of the cannula 50 and the anchor 42 into the membrane M of the first obturator foramen OF; and fixing the end portion of the first arm 704 to the membrane M of the first obturator foramen OF.

An addition to the method of anchoring the support 700 relative to the pelvis includes: inserting the anchor 42 into a lumen in a cannula 50; inserting a leading end of the cannula 50 and the anchor 42 into the perineal incision; pushing the leading end of the cannula 50 and the anchor 42 into the periosteum tissue PT of the ramus IR adjacent to the first obturator foramen OF; and fixing the end portion of the first arm 704 to the periosteum tissue PT of the ramus IR adjacent to the first obturator foramen OF.

One embodiment provides a tissue anchor comprising:
a body oriented on a longitudinal axis, the body having a leading tip, a leading end portion extending from the leading tip, a trailing end portion connected to the leading end portion, with the trailing end portion terminating in a trailing tip that is located opposite of the leading tip;
first and second protrusions formed on the leading end portion of the body, with each of the first and second protrusions extending outward in a radial direction perpendicular to the longitudinal axis, with a first anchor width measured between the first and second protrusions being greater than a second anchor width measured at the trailing end portion of the body;
a tissue engaging fin integrated with the leading end portion of the body and oriented in a direction perpendicular to the radial direction of the first and second protrusions, the tissue engaging fin having a fin width and provided with an eyelet formed through the fin width; and
a gripping tab removably attached to the tissue engaging fin.

One embodiment provides a method of fixating an implantable material in a patient, the method comprising:
forming an incision in the patient;
inserting an anchor into a bore of a cannula, with the anchor attached to a support by a suture having ends that are bonded together to form a continuous suture loop that is looped through an eyelet of the anchor and engaged through the support;
inserting the cannula into the incision and along a cannula path into soft tissue;

ejecting the anchor out of the bore of the cannula and into the soft tissue;

pulling on the suture in a direction away from the patient, and rotating the anchor to position a length of the anchor transverse to the cannula path; and breaking the continuous suture loop, tying a knot in the suture, and fixating the support in the patient.

One embodiment provides a tissue anchor system comprising:

a support material;

a suture engaged with the support material;

an anchor comprising a body, a fin extending from the body in a first direction with an eyelet formed in the fin, a pair of radial barrels extending from the body in a radial direction perpendicular to the first direction, and a gripping tab removably attached to the fin, with the suture engaged with the eyelet of the fin; and an introducer having a cannula defining a bore sized to receive the body of the anchor and a slot formed in a wall of the cannula, with the slot sized to receive the fin of the anchor, and an ejection mechanism provided to eject the anchor out of the cannula.

One embodiment provides a method of treating urinary incontinence in a patient, the method comprising:

forming one and only one incision in the patient and exposing tissue of a urethra;

implanting a base of a support in the patient by placing an anchor into tissue of an obturator foramen, with the anchor attached to the base of the support by a suture having ends that are bonded together to form a continuous suture loop that is looped through an eyelet of the anchor and engaged through the base of the support;

breaking the continuous suture loop, tying a knot in the suture, and fixating the base of the support in the patient;

implanting an arm of the support in the patient by placing a second anchor into periosteum tissue lateral to a pubic symphysis, with the second anchor attached to the arm of the support by a second suture having ends that are bonded together to form a second continuous suture loop that is looped through an eyelet of the second anchor and engaged through the arm of the support; and breaking the second continuous suture loop, tying a knot in the second suture, and fixating the arm of the support over the periosteum tissue.

FIG. 75 is a perspective view of one embodiment of an adjustable incontinence treatment device 800. The incontinence treatment device 800 (device 800) includes a support 802 connected at one end 804 to a fixed anchor 42FX by a first suspending member 806 and a second suspending member 808 attached at an opposite second end 810 of the support 802 that is movable through the eyelet 48 of an adjustable anchor 42AJ. Each anchor 42FX and 42AJ includes the removable insertion tab 40 described above that aids in placing the anchor into a cannula of an introducer tool.

The device 800 is implanted in a patient to treat urinary incontinence. In one method of placing the device 800, the patient is placed in a lithotomy position and prepped for surgery. A single (one and only one) incision is made in an upper wall of the vagina (the anterior wall) and tissue is dissected to expose a portion of the urethra. The left hand tool 28b (FIG. 1) is employed to place the fixed anchor 42FX in the obturator foramen (OF) on the left side of the patient. The anchor 42FX is inserted into the tool 28b through the use of the insertion tab 40. The insertion tab 40 is removed and discarded. The introducer 28b is inserted into the vaginal incision and passed along a path behind the descending ischial pubic ramus until the tip of the introducer 28b passes through the muscle of the left side OF. An audible "pop" can be heard in some instances, indicating that the tip of the introducer has passed through the muscle of the foramen. The button 56 is advanced and the fixed anchor 42FX is inserted into the left OF. The support 802 is thus fixed relative to the left side OF.

The right hand tool 28a (FIG. 1) is employed to place the adjustable anchor 42AJ in the OF on the right side of the patient. The anchor 42AJ is inserted into the tool 28a through the use of the insertion tab 40. The insertion tab 40 is removed and discarded. The introducer 28a is inserted into the vaginal incision and passed along a path behind the descending ischial pubic ramus on the right side of the patient until the tip of the introducer 28a passes through the muscle of the right side OF. An audible "pop" can be heard in some instances, indicating that the tip of the introducer has passed through the muscle of the foramen. The button 56 is advanced and the adjustable anchor 42AJ is inserted into the right OF. The support 802 is thus suspended under the urethra and the two anchors 42FX and 42AJ. The second suspending member 808 is movable through the eyelet 48 of the adjustable anchor 42AJ and extends out of the incision. The surgeon positions the support 802 relative to the urethra to achieve a desired location by sliding the suspending member 808 through the adjustable anchor 42AJ. When the support is positioned as desired by the surgeon, the surgeon then ties or terminates the second suspending member 808 to itself, to the support 802, or to tissue. This allows the surgeon to adjust the location of the support 802 to accommodate different body types and variations in the procedure. The excess portions of the suspending members 806, 808 are removed and the incision is closed.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention is limited only by its claims and their equivalents.

What is claimed is:

1. A method of treating urinary incontinence in a patient, the method comprising:

forming one and only one incision in the patient and exposing tissue of a urethra;

implanting a base of a support in the patient by placing a first anchor into tissue of an obturator foramen, with the first anchor attached to the base of the support by a suture having ends that are bonded together to form a first continuous suture loop that is looped through an eyelet of the first anchor and engaged through the base of the support;

breaking the first continuous suture loop, tying a knot in the suture, and fixating the base of the support in the patient;

implanting an arm of the support in the patient by placing a second anchor into periosteum tissue lateral to a pubic symphysis, with the second anchor attached to the arm of the support by a second suture having ends that are bonded together to form a second continuous suture loop that is looped through an eyelet of the second anchor and engaged through the arm of the support; and breaking the second continuous suture loop, tying a knot in the second suture, and fixating the arm of the support over the periosteum tissue.

2. The method of claim 1, further comprising:
fixating the base of the support in the patient, pulling on the arm of the support and applying tension to the support, and fixating the arm of the support over the periosteum tissue.

3. The method of claim 1, comprising inserting an entirety of the support through the one and only one incision in the patient.

4. The method of claim 1, further comprising:
placing a separate anchor into tissue of a second obturator foramen, with the separate anchor attached to the base of the support by a separate suture having ends that are bonded together to form a separate continuous suture loop that is looped through an eyelet of the separate anchor and engaged through the base of the support; and breaking the separate continuous suture loop, tying a knot in the separate suture, and fixating the base of the support in the patient by suspending the base of the support to the second obturator foramen with the separate suture.

5. The method of claim 1, comprising inserting the second anchor into a bore of a cannula;
inserting the cannula into the one and only one incision and along a cannula path into the periosteum tissue;
ejecting the second anchor out of the bore of the cannula and into the periosteum tissue; and
pulling on the second suture in a direction away from the patient, and rotating the second anchor to position a length of the second anchor transverse to the cannula path.

6. The method of claim 1, comprising ejecting the first anchor out of a bore of a cannula, moving the first anchor up a ramp formed by the cannula, rotating the first anchor away from the cannula, and placing the first anchor into the tissue of the obturator foramen.

7. The method of claim 1, comprising ejecting the second anchor out of a bore of a cannula, moving the second anchor up a ramp formed by the cannula, rotating the second anchor away from the cannula, and placing the second anchor into the periosteum tissue lateral to the pubic symphysis.

8. The method of claim 1, wherein the first anchor includes an eyelet formed in a fin that is integrated to a leading end portion of the first anchor, the method comprising:
placing the first anchor along a pathway into the tissue of the obturator foramen; and
rotating the first anchor to position a length of the first anchor transverse to the pathway and pulling the fin into engagement with the tissue of the obturator foramen.

9. The method of claim 1, wherein the second anchor includes an eyelet formed in a fin that is integrated to a leading end portion of the second anchor, the method comprising:
placing the second anchor along a pathway into the periosteum tissue; and
rotating the second anchor to position a length of the second anchor transverse to the pathway and pulling the fin into engagement with the periosteum tissue.

* * * * *